United States Patent [19]

Ikeda et al.

[11] Patent Number: 5,616,594
[45] Date of Patent: Apr. 1, 1997

[54] TRIAZOLE DERIVATIVES, INSECTICIDE, ACARICIDE AND METHODS THEREOF

[75] Inventors: Atsuhiko Ikeda; Masami Ozaki; Reijiro Honami; Takashi Yumita, all of Iwata-gun; Hiroyuki Yano, Ogasa-gun; Yuki Nakano, Ogasa-gun; Yutaka Kurihara, Ogasa-gun; Tadayoshi Hirano, Kakegawa, all of Japan

[73] Assignees: Ihara Chemical Industry Co. Ltd.; Kumiai Chemical Industrial Co., Ltd., both of Tokyo, Japan

[21] Appl. No.: 338,446
[22] PCT Filed: Apr. 15, 1994
[86] PCT No.: PCT/JP94/00629
  § 371 Date: Nov. 18, 1994
  § 102(e) Date: Nov. 18, 1994
[87] PCT Pub. No.: WO94/24110
  PCT Pub. Date: Oct. 27, 1994

[30] Foreign Application Priority Data

Apr. 16, 1993 [JP] Japan ................... 5-113802

[51] Int. Cl.$^6$ ............... A01N 43/653; C07D 401/12; C07D 401/10
[52] U.S. Cl. ............... 514/340; 514/333; 546/256; 546/272.4
[58] Field of Search ............... 546/256, 276, 546/272.4; 514/333, 340

[56] References Cited

U.S. PATENT DOCUMENTS

| | | |
|---|---|---|
| 4,151,169 | 4/1979 | Sale et al. . |
| 4,414,221 | 11/1983 | Parsons et al. . |
| 4,788,210 | 11/1988 | Luthy et al. . |
| 5,318,959 | 6/1994 | Ozaki et al. ............... 514/63 |

FOREIGN PATENT DOCUMENTS

| | | |
|---|---|---|
| 0572142 | 12/1993 | European Pat. Off. . |
| 5310712 | 11/1993 | Japan . |

OTHER PUBLICATIONS

Research Disclosure vol. 278, pp. 356–357 (Jun. 1987).
Chemical Abstracts vol. 80, No. 15, 15 Apr. 1974, #82270b.

*Primary Examiner*—Patricia L. Morris
*Attorney, Agent, or Firm*—Watson Cole Stevens Davis, P.L.L.C.

[57] ABSTRACT

The invention provides a triazole derivative represented by a general formula

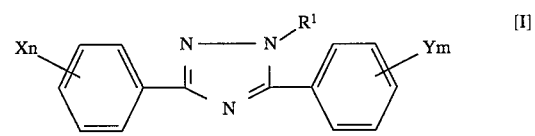

(wherein $R^1$ is an alkyl group, X is a hydrogen atom, a halogen atom or an alkyl group, n is an integer of 1–5, Y is a halogen atom, a nitro group or an alkyl group, and m is an integer of 2–5) as well as insecticide and acaricide containing the same as an active ingredient.

The triazole derivatives according to the invention exhibit an excellent effectiveness against harmful pests, particularly aphids and mites.

5 Claims, No Drawings

TRIAZOLE DERIVATIVES, INSECTICIDE, ACARICIDE AND METHODS THEREOF

TECHNICAL FIELD

This invention relates to triazole derivatives, insecticides and acaricides containing them as an active ingredient, and methods thereof.

BACKGROUND ART

As a prior art including compounds similar to the compound according to the invention in the chemical structure, there have hitherto been known the specification of JP-A-56-154464 and technical report RD 278004. They disclose that the compounds have insecticidal and acaricidal activities. However, it can not be said that the compounds described in the above opened specification and technical report are sufficient in the insecticidal and acaricidal activities.

DISCLOSURE OF INVENTION

The inventors have synthesized various triazole derivatives in order to develop novel and useful insecticide and acraricide and made various studies with respect to physiological activity thereof. As a result, it has been found that the compounds according to the invention have very excellent insecticidal and acaricidal activities against harmful insects and harmful mites as compared with the compounds concretely described in the specification of JP-A-56-154464 and technical report RD 278004. Particularly, it has been found that they are characterized by having plural substituent groups on a benzene ring substituted in 5-position of a triazole ring and have a very excellent insecticidal activity against mites such as two-spotted spider mite, Kanzawa spider mite, citrus red mite and the like; aphids such as cotton aphid and the like; and lepidoptera pests such as diamond-back moth and the like, and as a result the invention has been accomplished.

The invention lies in a triazole derivative represented by a general formula [I]

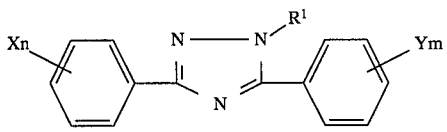

(wherein $R^1$ is an alkyl group, X is a hydrogen atom, a halogen atom, an alkyl group, an alkoxy group, an alkylthio group, a nitro group, a cyano group or a trifluoromethyl group, n is an integer of 1–5, provided that when n is 2 or more, X may optionally be same or different combination, Y is a halogen atom, a nitro group, an alkyl group, an alkoxy group, an alkoxyalkyl group, an alkoxyalkoxy group, an alkylthio group, an alkylsulfinyl group, an alkylsulfonyl group, an alkylthioalkyl group, an alkylsulfinylalkyl group, an alkylsulfonylalkyl group, a cycloalkyl group, a cycloalkylalkyl group, a cycloalkylalkenyl group, a cycloalkylalkynyl group, a haloalkyl group, a haloalkoxy group, a trialkylsilylalkyl group, a trialkylsilylalkoxy group, an alkenyl group, an alkenyloxy group, an alkynyl group, an alkynyloxy group or a group represented by a general formula

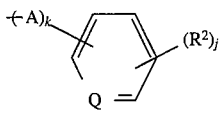

(wherein A is an oxygen atom, a sulfur atom, a lower alkylene group, a lower alkyleneoxy group, an oxy lower alkylene group, a lower alkyleneoxy lower alkylene group, a lower alkylenethio group, a thio lower alkylene group, a vinylene group or an ethynylene group, k is 0 or 1, Q is a methine group or a nitrogen atom, $R^2$ is a hydrogen atom, a halogen atom, an alkyl group, an alkoxy group, a trifluoromethyl group or a trifluoromethoxy group, j is an integer of 1–5, provided that when j is 2 or more, $R^2$ may optionally be same or different combination), m is an integer of 2–5 and Y may optionally be same or different combinations, and insecticides and acaricides containing the derivative as an active ingredient and methods thereof.

In this specification, the alkyl group means a straight or branched-chain alkyl group having a carbon number of 1–30 and includes, for example, methyl group, ethyl group, n-propyl group, isopropyl group, n-butyl group, isobutyl group, sec-butyl group, t-butyl group, n-pentyl group, isoamyl group, neopentyl group, n-hexyl group, isohexyl group, 3,3-dimethylbutyl group, n-heptyl group, 5-methylhexyl group, 4-methylhexyl group, 3-methylhexyl group, 4,4-dimethylpentyl group, n-octyl group, 6-methylheptyl group, n-nonyl group, 7-methyloctyl group, n-decyl group, 8-methylnonyl group, n-undecyl group, 9-methyldecyl group, n-dodecyl group, 10-methylundecyl group, n-tridecyl group, 11-methyldodecyl group, n-tetradecyl group, 12-methyltridecyl group, n-pentadecyl group, 13-methyltetradecyl group, n-hexadecyl group, n-heptadecyl group, n-octadecyl group, n-nonadecyl group, n-eicosyl group and the like.

The alkoxy group, alkylthio group, alkylsulfinyl group and alkylsulfonyl alkyl group are (alkyl)-O-group, (alkyl)-S-group, (alkyl)-SO-group and (alkyl)-SO$_2$-group, in which each alkyl portion has the same meaning as mentioned above. The alkylthioalkyl group, alkyl-sulfinylalkyl group and alkylsulfonyl group are (alkyl)-S-(alkyl)-group, (alkyl)-SO-(alkyl)-group and (alkyl)-SO$_2$-(alkyl)-group, in which each alkyl portion has the same meaning as mentioned above. The halogen atom includes fluorine, chlorine, bromine and iodine.

The alkenyl group means a straight or branched-chain alkenyl group having a carbon number of 2–20 and includes, for example, vinyl group, propenyl group, isopropenyl group, butenyl group, pentenyl group, hexenyl group, heptenyl group, octenyl group, 3-methyl-1-butenyl group, 4-methyl-1-pentenyl group and the like.

The alkynyl group means a straight or branched-chain alkynyl group having a carbon number of 2–20 and includes, for example, ethynyl group, propynyl group, butynyl group, pentynyl group, hexynyl group, 3,3-dimethyl-1-butynyl group, 4-methyl-1-pentynyl group, 3-methyl-1-pentynyl group, 5-methyl-1-hexynyl group, 4-methyl-1-hexynyl group, 3-methyl-1-hexynyl group, heptynyl group, octynyl group, nonynyl group, decynyl group, undecynyl group, dodecynyl group, tridecynyl group, tetradecynyl group, pentadecynyl group, hexadecynyl group and the like.

The cycloalkyl group means a cycloalkyl group having a carbon number of 3–12 and includes, for example, cyclopropyl group, cyclobutyl group, cyclopentyl group, cyclohexyl group, cycloheptyl group, cyclooctyl group and the like. The cycloalkylalkyl group means a cycloalkylalkyl group having a carbon number of 6–12 and includes, for example, cyclopentylmethyl group, cyclohexylmethyl group, cyclopentylethyl group, cyclohexylethyl group, cyclopentylpropyl group, cyclohexylpropyl group, cyclohexylpentyl group and the like.

The cycloalkylalkoxy group means (cycloalkylalkyl)-O-group in which the cycloalkylalkyl portion has the same meaning as mentioned above. The cycloalkylalkenyl group means a cycloalkylalkenyl group having a carbon number of 5–12 and includes, for example, cyclopentylvinyl group, cyclohexylvinyl group, 3-cyclopentyl-1-propenyl group, 3-cyclohexyl-1-propenyl group, 5-cyclohexyl-1-pentenyl group and the like. The cycloalkylalkynyl group means a cycloalkylalkynyl group having a carbon number of 5–12 and includes, for example, cyclopentylethynyl group, cyclohexylethynyl group, 3-cyclopentyl-1-propynyl group, 3-cyclohexyl-1-propynyl group and the like.

The haloalkyl group means an alkyl group substituted with a halogen atom and includes, for example, trifluoromethyl group, pentafluoroethyl group and the like. The haloalkoxy group is (haloalkyl)-O-group in which the haloalkyl portion has the same meaning as described above.

The trialkylsilylalkyl group is, for example, trimethylsilylmethyl group, dimethylethylsilylmethyl group, butyldimethylsilylmethyl group or the like. The trialkylsilylalkoxy group is (trialkylsilylalkyl)-O-group in which the trialkylsilylalkyl portion has the same meaning as described above.

The lower alkylene group includes, for example, methylene group, ethylene group, methylmethylene group, trimethylene group, 1-methylethylene group, dimethylmethylene group, tetramethylene group, 1-methyltrimethylene group, 2-methyltrimethylene group and the like. The lower alkyleneoxy group is -(lower alkylene)-O-group in which the lower alkylene portion has the same meaning as described above. The oxy lower alkylene group is -O-(lower alkylene)-group in which the lower alkylene portion has the same meaning as described above.

The lower alkyleneoxy lower alkylene group is (lower alkylene)-O-(lower alkylene)-group in which the lower alkylene portion has the same meaning as described above. The lower alkylenethio group is -(lower alkylene)-S-group in which the lower alkylene portion has the same meaning as described above. The thio lower alkylene group is -S-(lower alkylene)-group in which the lower alkylene portion has the same meaning as described above.

As a preferable compound group in the general formula [I], mention may be made of compounds in which $R^1$ is a straight or branched-chain alkyl group having a carbon number of 1–6, preferably methyl group, X is a hydrogen atom, a halogen atom, a straight or branched-chain alkyl group having a carbon number of 1–4, a nitro group, a cyano group or a trifluoromethyl group, n is an integer of 1–3 provided that when n is 2 or 3, X may optionally be same or different combination, Y is a halogen atom, a nitro group, a straight or branched-chain alkyl group having a carbon number of 1–20, a straight or branched-chain alkoxy group having a carbon number of 1–20, a cycloalkyl group having a carbon number of 3–12, a cycloalkylalkyl group having a carbon number of 6–12, a cycloalkylalkoxy group having a carbon number of 3–12, a straight or branched-chain alkylthio group having a carbon number of 1–20, an alkylsulfinyl group, an alkylsulfonyl group, a straight or branched-chain alkynyl group having a carbon number of 3–16, a cycloalkylalkynyl group having a carbon number of 5–12, tri(alkyl)silylalkyl group, tri(alkyl)silylalkoxy group or a group represented by the formula:

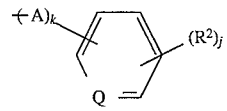

(wherein A is an oxygen atom, a sulfur atom, a lower alkylene group, a lower alkyleneoxy group, an oxy lower alkylene group or a lower alkyleneoxy lower alkylene group, k is 0 or 1, Q is methine group or a nitrogen atom, $R^2$ is a hydrogen atom, a halogen atom, an alkyl group, an alkoxy group, a trifluoromethyl group or a trifluoromethoxy group, j is an integer of 1–5 provided that when j is 2 or more, $R^2$ may optionally be same or different combination), m is an integer of 2–5 and Y may optionally be same or different combination.

The compounds of the general formula [I] according to the invention are exemplified in Tables 1–2. Moreover, compound number is referred in subsequent description.

TABLE 1

| Compound No. | $R^1$ | Xn | Ym | Melting point (°C.) or refractive index ($n_D^{20}$) |
|---|---|---|---|---|
| 1 | $CH_3$ | 2-Cl | 2-Cl, 3-$NO_2$ | 124.0–125.0 |
| 2 | $CH_3$ | 2-Cl, 6-F | 2-Cl, 3-$NO_2$ | 112.0–114.0 |
| 3 | $CH_3$ | 2-Cl | 2-Cl, 4-$NO_2$ | |
| 4 | $CH_3$ | 2-Cl, 6-F | 2-Cl, 4-$NO_2$ | 144.0–148.0 |
| 5 | $CH_3$ | 2-Cl | 2-Cl, 5-$NO_2$ | 129.0–130.0 |
| 6 | $CH_3$ | 2-Cl, 6-F | 2-Cl, 5-$NO_2$ | 121.0–124.0 |
| 7 | $CH_3$ | 2-Cl | 3-$NO_2$, 4-Cl | |
| 8 | $CH_3$ | 2-Cl, 6-F | 3-$NO_2$, 4-Cl | 124.0–126.5 |
| 9 | $CH_3$ | 2-Cl | 2,6-$Cl_2$, 3-$NO_2$ | 155.0–156.0 |
| 10 | $CH_3$ | 2-Cl, 6-F | 2,6-$Cl_2$, 3-$NO_2$ | 108.0–109.0 |
| 11 | $CH_3$ | 2-Cl | 2,6-$Cl_2$, 4-$NO_2$ | |
| 12 | $CH_3$ | 2-Cl, 6-F | 2,6-$Cl_2$, 4-$NO_2$ | 158.0–162.0 |
| 13 | $CH_3$ | 2-Cl | 2,4-$Cl_2$, 3,5-$(NO_2)_2$ | |
| 14 | $CH_3$ | 2-Cl, 6-F | 2,4-$Cl_2$, 3,5-$(NO_2)_2$ | |
| 15 | $CH_3$ | 2-Cl | 2-Cl, 4-$C_2H_5$ | 75.5–77.5 |
| 16 | $CH_3$ | 2-Cl, 6-F | 2-Cl, 4-$C_2H_5$ | 1.5930 |
| 17 | $CH_3$ | 2-Cl, 6-F | 3-Cl, 4-$C_2H_5$ | |

TABLE 1-continued

| Compound No. | $R^1$ | Xn | Ym | Melting point (°C.) or refractive index ($n_D^{20}$) |
|---|---|---|---|---|
| 18 | $CH_3$ | 2-Cl | 2-Cl, 4-$C_3H_7$ | 70.0–72.0 |
| 19 | $CH_3$ | 2-Cl, 6-F | 2-Cl, 4-$C_3H_7$ | 1.5868 |
| 20 | $C_2H_5$ | 2-Cl | 2-Cl, 4-$C_3H_7$ | |
| 21 | $C_2H_5$ | 2-Cl, 6-F | 2-Cl, 4-$C_3H_7$ | |
| 22 | $C_3H_7$-i | 2-Cl | 2-Cl, 4-$C_3H_7$ | |
| 23 | $C_3H_7$-i | 2-Cl, 6-F | 2-Cl, 4-$C_3H_7$ | |
| 24 | $CH_3$ | 2-Cl | 2-Cl, 4-$C_3H_7$-i | 90.0–92.0 |
| 25 | $CH_3$ | 2-Cl, 6-F | 2-Cl, 4-$C_3H_7$-i | |
| 26 | $CH_3$ | 2-Cl | 2,4,6-$(C_3H_7$-i$)_3$ | |
| 27 | $CH_3$ | 2-Cl, 6-F | 2,4,6-$(C_3H_7$-i$)_3$ | |
| 28 | $CH_3$ | 2-Cl | 2-Cl, 4-$C_4H_9$ | 1.5962 |
| 29 | $CH_3$ | 2-Cl, 6-F | 2-Cl, 4-$C_4H_9$ | 1.5667 |
| 30 | $CH_3$ | H | 2-Cl, 5-$C_4H_9$-t | |
| 31 | $CH_3$ | 2-Cl | 2-Cl, 5-$C_4H_9$-t | 1.5931 |
| 32 | $CH_3$ | 2-Cl, 6-F | 2-Cl, 5-$C_4H_9$-t | 1.5943 |
| 33 | $CH_3$ | 2,6-$F_2$ | 2-$OC_2H_5$, 4-$C_4H_9$-t | 146.0–148.0 |
| 34 | $CH_3$ | 2-Cl | 2-$OC_2H_5$, 4-$C_4H_9$-t | 1.5818 |
| 35 | $CH_3$ | 2-Cl, 6-F | 2-$OC_2H_5$, 4-$C_4H_9$-t | 108.0–111.0 |
| 36 | $CH_3$ | 2,6-$F_2$ | 2-Cl, 4-$C_5H_{11}$ | 1.5629 |
| 37 | $CH_3$ | 2-Cl | 2-Cl, 4-$C_5H_{11}$ | 1.5849 |
| 38 | $CH_3$ | 2-Cl, 6-F | 2-Cl, 4-$C_5H_{11}$ | 1.5710 |
| 39 | $CH_3$ | 2,6-$F_2$ | 2-Cl, 4-$C_6H_{13}$ | 1.5591 |
| 40 | $CH_3$ | 2-Cl | 2-Cl, 4-$C_6H_{13}$ | 1.5830 |
| 41 | $CH_3$ | 2-Cl, 6-F | 2-Cl, 4-$C_6H_{13}$ | 1.5638 |
| 42 | $CH_3$ | 2-Cl | 2-F, 5-$C_6H_{13}$ | 1.5779 |
| 43 | $CH_3$ | 2-Cl, 6-F | 2-F, 5-$C_6H_{13}$ | 1.5608 |
| 44 | $CH_3$ | 2-Cl | 2-Cl, 4-$C_7H_{15}$ | 1.5824 |
| 45 | $CH_3$ | 2-Cl, 6-F | 2-Cl, 4-$C_7H_{15}$ | |
| 46 | $CH_3$ | 2,6-$F_2$ | 2-F, 5-$C_{11}H_{23}$ | 70.0–73.0 |
| 47 | $CH_3$ | 2-Cl | 2-F, 5-$C_{11}H_{23}$ | 35.0–37.0 |
| 48 | $CH_3$ | 2-Cl, 6-F | 2-F, 5-$C_{11}H_{23}$ | 1.5419 |
| 49 | $CH_3$ | 2,6-$F_2$ | 2-Cl, 4-$C_{12}H_{25}$ | |
| 50 | $CH_3$ | 2-Cl | 2-Cl, 4-$C_{12}H_{25}$ | 76.0–77.0 |
| 51 | $CH_3$ | 2-Cl, 6-F | 2-Cl, 4-$C_{12}H_{25}$ | 1.5490 |
| 52 | $CH_3$ | 2-Cl, 6-F | 3-Cl, 4-$C_{15}H_{31}$ | |
| 53 | $CH_3$ | H | 3,5-$(OC_2H_5)_2$ | |
| 54 | $CH_3$ | 2-$CH_3$ | 3,5-$(OC_2H_5)_2$ | |
| 55 | $CH_3$ | 2-$OCH_3$ | 3,5-$(OC_2H_5)_2$ | |
| 56 | $CH_3$ | 2-$SCH_3$ | 3,5-$(OC_2H_5)_2$ | |
| 57 | $CH_3$ | 2-$NO_2$ | 3,5-$(OC_2H_5)_2$ | |
| 58 | $CH_3$ | 2-CN | 3,5-$(OC_2H_5)_2$ | |
| 59 | $CH_3$ | 2-$CF_3$ | 3,5-$(OC_2H_5)_2$ | |
| 60 | $CH_3$ | 2-Cl | 2-$OC_2H_5$, 4,5-$Cl_2$ | |
| 61 | $CH_3$ | 2-Cl, 6-F | 2-$OC_2H_5$, 4,5-$Cl_2$ | 115.0–117.0 |
| 62 | $CH_3$ | 2-Cl | 2-$OC_2H_5$, 4,5-$F_2$ | |
| 63 | $CH_3$ | 2-Cl, 6-F | 2-$OC_2H_5$, 4,5-$F_2$ | 1.5590 |
| 64 | $CH_3$ | 2-Cl | 2-Cl, 4-$OC_4H_9$ | 60.0–62.0 |
| 65 | $CH_3$ | 2-Cl, 6-F | 2-Cl, 4-$OC_4H_9$ | 1.5631 |
| 66 | $CH_3$ | 2-Cl | 2-Cl, 4-$OC_5H_{11}$ | 71.0–73.0 |
| 67 | $CH_3$ | 2-Cl, 6-F | 2-Cl, 4-$OC_5H_{11}$ | |
| 68 | $CH_3$ | 2-Cl, 6-F | 3-$OC_5H_{11}$, 4-Cl | not measurable |
| 69 | $CH_3$ | 2-Cl, 6-F | 3-$OC_5H_{11}$-i, 4-Cl | |
| 70 | $CH_3$ | 2-Cl | 3,5-$(OC_5H_{11})_2$ | |
| 71 | $CH_3$ | 2-Cl, 6-F | 3,5-$(OC_5H_{11})_2$ | |
| 72 | $CH_3$ | 2,6-$Cl_2$ | 2-Cl, 4-$OC_8H_{17}$ | 1.5728 |
| 73 | $CH_3$ | 2-Cl | 2-Cl, 4-$OC_8H_{17}$ | 51.0–54.0 |
| 74 | $CH_3$ | 2-Cl, 6-F | 2-Cl, 4-$OC_8H_{17}$ | 1.5641 |
| 75 | $CH_3$ | 2-Cl | 3-Cl, 4-$OC_8H_{17}$ | 47.0–49.0 |
| 76 | $CH_3$ | 2-Cl, 6-F | 3-Cl, 4-$OC_8H_{17}$ | 1.5658 |
| 77 | $CH_3$ | 2-Cl | 3-$OC_8H_{17}$, 4-Cl | not measurable |
| 78 | $CH_3$ | 2-Cl, 6-F | 3-$OC_8H_{17}$, 4-Cl | 1.5658 |
| 79 | $CH_3$ | 2-Cl | 3,5-$(OC_8H_{17})_2$ | |
| 80 | $CH_3$ | 2-Cl, 6-F | 3,5-$(OC_8H_{17})_2$ | |
| 81 | $CH_3$ | 2-$NO_2$ | 3-Cl, 4-$OC_{12}H_{25}$ | |
| 82 | $CH_3$ | 2-$SCH_3$ | 3-Cl, 4-$OC_{12}H_{25}$ | |
| 83 | $CH_3$ | 2-Cl | 3-Cl, 4-$OC_{15}H_{31}$ | |
| 84 | $CH_3$ | 2-Cl, 6-F | 3-Cl, 4-$OC_{15}H_{31}$ | |
| 85 | $CH_3$ | 2-Cl, 6-F | 3-Cl, 4-$CH_2OCH_3$ | |

TABLE 1-continued

[Structure: Xn-phenyl-C(=N-)-N(-N(R¹))-C(=N)-phenyl-Ym diagram]

| Compound No. | R¹ | Xn | Ym | Melting point (°C.) or refractive index ($n_D^{20}$) |
|---|---|---|---|---|
| 86 | $CH_3$ | 2-Cl, 6-F | 3-Cl, 4-$(CH_2)_3OC_3H_7$ | |
| 87 | $CH_3$ | 2-Cl | 2-Cl, 4-$OC_2H_4OCH_3$ | 1.5946 |
| 88 | $CH_3$ | 2-Cl, 6-F | 2-Cl, 4-$OC_2H_4OCH_3$ | |
| 89 | $CH_3$ | 2-Cl, 6-F | 3-$SCH_3$, 4-Cl | |
| 90 | $CH_3$ | 2-Cl, 6-F | 3-$SC_3H_7$, 4-Cl | |
| 91 | $CH_3$ | 2-Cl, 6-F | 3-$SC_6H_{13}$, 4-Cl | |
| 92 | $CH_3$ | 2-Cl, 6-F | 3-$SOCH_3$, 4-Cl | |
| 93 | $CH_3$ | 2-Cl, 6-F | 3-$SOC_3H_7$, 4-Cl | |
| 94 | $CH_3$ | 2-Cl, 6-F | 3-$SOC_6H_{13}$, 4-Cl | |
| 95 | $CH_3$ | 2-Cl, 6-F | 3-$SO_2CH_3$, 4-Cl | |
| 96 | $CH_3$ | 2-Cl, 6-F | 3-$SO_2C_3H_7$, 4-Cl | |
| 97 | $CH_3$ | 2-Cl, 6-F | 3-$SO_2C_6H_{13}$, 4-Cl | |
| 98 | $CH_3$ | 2-Cl, 6-F | 3-$CH_2SCH_3$, 4-$C_2H_5$ | |
| 99 | $CH_3$ | 2-Cl, 6-F | 3-$CH_2SC_3H_7$, 4-$C_2H_5$ | |
| 100 | $CH_3$ | 2-Cl | 3-Br, 4-$CH_2SC_5H_{11}$ | |
| 101 | $CH_3$ | 2-Cl, 6-F | 3-Br, 4-$CH_2SC_5H_{11}$ | |
| 102 | $CH_3$ | 2-Cl, 6-F | 3-$CH_2SC_6H_{13}$, 4-$C_2H_5$ | |
| 103 | $CH_3$ | 2-Cl, 6-F | 3-$CH_2SOCH_3$, 4-$C_2H_5$ | |
| 104 | $CH_3$ | 2-Cl, 6-F | 3-$CH_2SOC_3H_7$, 4-$C_2H_5$ | |
| 105 | $CH_3$ | 2-Cl | 3-Br, 4-$CH_2SOC_5H_{11}$ | |
| 106 | $CH_3$ | 2-Cl, 6-F | 3-Br, 4-$CH_2SOC_5H_{11}$ | |
| 107 | $CH_3$ | 2-Cl, 6-F | 3-$CH_2SOC_6H_{13}$, 4-$C_2H_5$ | |
| 108 | $CH_3$ | 2-Cl | 3-Br, 4-$CH_2SO_2C_5H_{11}$ | |
| 109 | $CH_3$ | 2-Cl, 6-F | 3-Br, 4-$CH_2SO_2C_5H_{11}$ | |
| 110 | $CH_3$ | 2-Cl, 6-F | 3-$CH_2SO_2CH_3$, 4-$C_2H_5$ | |
| 111 | $CH_3$ | 2-Cl, 6-F | 3-$CH_2SO_2C_3H_7$, 4-$C_2H_5$ | |
| 112 | $CH_3$ | 2-Cl, 6-F | 3-$CH_2SO_2C_6H_{13}$, 4-$C_2H_5$ | |
| 113 | $CH_3$ | 2-Cl | 2-Cl, 5-$C_2F_5$ | |
| 114 | $CH_3$ | 2-Cl, 6-F | 2-Cl, 5-$C_2F_5$ | |
| 115 | $CH_3$ | 2-Cl | 2-Cl, 5-$C_4F_9$ | |
| 116 | $CH_3$ | 2-Cl, 6-F | 2-Cl, 5-$C_4F_9$ | 1.5110 |
| 117 | $CH_3$ | 2-Cl | 3-$C_4F_9$, 4-Cl | |
| 118 | $CH_3$ | 2-Cl, 6-F | 3-$C_4F_9$, 4-Cl | 1.5392 |
| 119 | $CH_3$ | 2-Cl | 2-Cl, 5-$C_6F_{13}$ | 70.0–76.0 |
| 120 | $CH_3$ | 2-Cl, 6-F | 2-Cl, 5-$C_6F_{13}$ | 78.0–82.0 |
| 121 | $CH_3$ | 2-Cl, 6-F | 2-F, 5-$C_4F_9$ | 1.5090 |
| 122 | $CH_3$ | 2-Cl | 3,5-$Cl_2$, 5-$C_8F_{17}$ | |
| 123 | $CH_3$ | 2-Cl, 6-F | 3,5-$Cl_2$, 5-$O(CF_2)_2H$ | 96.0–101.0 |
| 124 | $CH_3$ | 2-Cl, 6-F | 3-Cl, 4-$(CH_2)_2C_4F_9$ | |
| 125 | $CH_3$ | 2-Cl | 2-Cl, 5-$OC_2F_5$ | |
| 126 | $CH_3$ | 2-Cl, 6-F | 2-Cl, 5-$OC_2F_5$ | |
| 127 | $CH_3$ | 2-Cl | 3-Cl, 4-$O(CH_2)_2C_4F_9$ | |
| 128 | $CH_3$ | 2-Cl, 6-F | 3-Cl, 4-$O(CH_2)_2C_4F_9$ | |
| 129 | $CH_3$ | 2-Cl | 3-Br, 4-$CH_2Si(CH_3)_3$ | |
| 130 | $CH_3$ | 2-Cl, 6-F | 3-Br, 4-$CH_2Si(CH_3)_3$ | |
| 131 | $CH_3$ | 2-Cl | 3-Br, 4-$OCH_2Si(CH_3)_3$ | |
| 132 | $CH_3$ | 2-Cl, 6-F | 3-Br, 4-$OCH_2Si(CH_3)_3$ | |
| 133 | $CH_3$ | 2-Cl, 6-F | 3-CH=$CH_2$, 4-Cl | |
| 134 | $CH_3$ | 2-Cl | 3-Br, 4-CH=$CHCH_3$ | |
| 135 | $CH_3$ | 2-Cl, 6-F | 3-Br, 4-CH=$CHCH_3$ | |
| 136 | $CH_3$ | 2-Cl, 6-F | 3-$CH_2$CH=$CHC_3H_7$, 4-Cl | |
| 137 | $CH_3$ | 2-Cl, 6-F | 3-OCH=$CH_2$, 4-Cl | |
| 138 | $CH_3$ | 2-Cl | 2-Cl, 4-$OCH_2$CH=$CH_2$ | 1.6083 |
| 139 | $CH_3$ | 2-Cl, 6-F | 2-Cl, 4-$OCH_2$CH=$CH_2$ | |
| 140 | $CH_3$ | 2-Cl, 6-F | 3-$OCH_2$CH=$CHC_3H_7$, 4-Cl | |
| 141 | $CH_3$ | 2-Cl, 6-F | 3-Cl, 4-C≡CH | |
| 142 | $CH_3$ | 2-Cl, 6-F | 3-Cl, 4-C≡$CC_4H_9$ | |
| 143 | $CH_3$ | 2-Cl, 6-F | 3-Cl, 4-OC≡CH | |
| 144 | $CH_3$ | 2-Cl, 6-F | 3-Cl, 4-OC≡$CC_4H_9$ | |
| 145 | $CH_3$ | 2-Cl | 2-Cl, 4-$OCH_2$C≡CH | 103.5–105.0 |
| 146 | $CH_3$ | 2-Cl, 6-F | 2-Cl, 4-$OCH_2$C≡CH | |

TABLE 1-continued

[Structure: Xn-phenyl-C(=N-N(R¹))-N=C-phenyl-Ym triazole-type structure]

| Compound No. | R¹ | Xn | Ym | Melting point (°C.) or refractive index ($n_D^{20}$) |
|---|---|---|---|---|
| 147 | CH₃ | 2-Cl | 2-Cl, 4-cyclohexyl | |
| 148 | CH₃ | 2-Cl, 6-F | 2-Cl, 4-cyclohexyl | |
| 149 | CH₃ | 2-Cl | 3-Br, 4-C₂H₄-cyclohexyl | |
| 150 | CH₃ | 2-Cl, 6-F | 3-Br, 4-C₂H₄-cyclohexyl | |
| 151 | CH₃ | 2-Cl | 3-Br, 4-CH=CH-cyclohexyl | |
| 152 | CH₃ | 2-Cl, 6-F | 3-Br, 4-CH=CH-cyclohexyl | |
| 153 | CH₃ | 2-Cl | 3-Br, 4-CH≡CH-cyclohexyl | |
| 154 | CH₃ | 2-Cl, 6-F | 3-Br, 4-CH≡CH-cyclohexyl | |

TABLE 2

[Structure: Xn-phenyl-C(=N-N(R¹))-N=C-R⁴]

| Compound No. | R¹ | Xn | R⁴ | Melting point (°C.) of refractive index ($n_D^{20}$) |
|---|---|---|---|---|
| 155 | CH₃ | 2-Cl | 4-Cl-phenyl-(4-OCF₃-phenyl) | |

TABLE 2-continued

Structure: Xn-phenyl-C(=N-N(R¹)-N=C-R⁴ (triazole)

| Compound No. | R¹ | Xn | R⁴ | Melting point (°C.) of refractive index ($n_D^{20}$) |
|---|---|---|---|---|
| 156 | CH₃ | 2-Cl, 6-F | 3-Cl-phenyl-(4-OCF₃-phenyl) | |
| 157 | CH₃ | 2-Cl, 6-F | 2-F-phenyl-(3-OCF₃-phenyl) | 117.0–119.0 |
| 158 | CH₃ | 2-Cl, 6-F | 3-Cl-phenyl-(4-OCF₃-phenyl) | 1.5925 |
| 159 | CH₃ | 2-Cl, 6-F | 2-Br-phenyl-CH=CH-phenyl | |
| 160 | CH₃ | 2-Cl, 6-F | 2-Br-phenyl-C≡C-phenyl | |
| 161 | CH₃ | 2-Cl, 6-F | 2-Cl-phenyl-CH₂-(3,4-Cl₂-phenyl) | 179.0–185.0 |
| 162 | CH₃ | 2-Cl, 6-F | 2-Br-phenyl-CH₂CH₂-phenyl | |
| 163 | CH₃ | 2,6-F₂ | 3-Cl-phenyl-CH₂O-(2,6-Cl₂-4-CF₃-phenyl) | |

TABLE 2-continued

[Structure: Xn-phenyl-triazole with R¹ and R⁴ substituents]

| Compound No. | R¹ | Xn | R⁴ | Melting point (°C.) or refractive index ($n_D^{20}$) |
|---|---|---|---|---|
| 164 | CH₃ | 2-Cl, 6-F | 3-Cl-4-(2,6-Cl₂-4-CF₃-phenoxymethyl)phenyl | |
| 165 | CH₃ | 2,6-F₂ | 3-Cl-4-(2-Cl-4-CF₃-phenoxymethyl)phenyl | |
| 166 | CH₃ | 2-Cl, 6-F | 3-Cl-4-(2-Cl-4-CF₃-phenoxymethyl)phenyl | |
| 167 | CH₃ | 2,6-F₂ | 3-Cl-4-(2-F-4-CF₃-phenoxymethyl)phenyl | |
| 168 | CH₃ | 2-Cl, 6-F | 3-Cl-4-(2-F-4-CF₃-phenoxymethyl)phenyl | |
| 169 | CH₃ | 2,6-F₂ | 3-Cl-4-(4-CF₃-phenoxymethyl)phenyl | |
| 170 | CH₃ | 2-Cl, 6-F | 3-Cl-4-(4-CF₃-phenoxymethyl)phenyl | |
| 171 | CH₃ | 2,6-F₂ | 3-Cl-4-(4-OCF₃-phenoxymethyl)phenyl | |
| 172 | CH₃ | 2-Cl, 6-F | 3-Cl-4-(4-OCF₃-phenoxymethyl)phenyl | |

TABLE 2-continued $$\text{Xn} - \text{C}_6\text{H}_4 - \underset{\underset{N}{\parallel}}{C} - N - N(R^1) - CH = R^4$$

| Compound No. | R¹ | Xn | R⁴ | Melting point (°C.) or refractive index ($n_D^{20}$) |
|---|---|---|---|---|
| 173 | CH₃ | 2,6-F₂ | 3-F-C₆H₃-CH₂O-(2,6-Cl₂-4-CF₃-C₆H₂)- | |
| 174 | CH₃ | 2-Cl, 6-F | 3-F-C₆H₃-CH₂O-(2,6-Cl₂-4-CF₃-C₆H₂)- | |
| 175 | CH₃ | 2,6-F₂ | 3-F-C₆H₃-CH₂O-(2-Cl-4-CF₃-C₆H₃)- | |
| 176 | CH₃ | 2-Cl, 6-F | 3-F-C₆H₃-CH₂O-(2-Cl-4-CF₃-C₆H₃)- | |
| 177 | CH₃ | 2,6-F₂ | 3-F-C₆H₃-CH₂O-(2-F-4-CF₃-C₆H₃)- | |
| 178 | CH₃ | 2-Cl, 6-F | 3-F-C₆H₃-CH₂O-(2-F-4-CF₃-C₆H₃)- | |
| 179 | CH₃ | 2,6-F₂ | 3-F-C₆H₃-CH₂O-(4-CF₃-C₆H₄)- | |
| 180 | CH₃ | 2-Cl, 6-F | 3-F-C₆H₃-CH₂O-(4-CF₃-C₆H₄)- | |
| 181 | CH₃ | 2,6-F₂ | 3-F-C₆H₃-CH₂O-(4-OCF₃-C₆H₄)- | |

TABLE 2-continued

Structure: Xn-phenyl-C(=N-N(R¹)-C(R⁴)=N) (1,2,4-triazole with Xn-phenyl and R⁴ substituents, R¹ on N)

| Compound No. | R¹ | Xn | R⁴ | Melting point (°C.) of refractive index ($n_D^{20}$) |
|---|---|---|---|---|
| 182 | $CH_3$ | 2-Cl, 6-F | 2-F-4-(4-$OCF_3$-phenoxymethyl)phenyl | |
| 183 | $CH_3$ | 2,6-$F_2$ | 2,6-di-Cl-4-[(2,6-di-Cl-4-$CF_3$-phenoxy)methyl]phenyl | |
| 184 | $CH_3$ | 2-Cl, 6-F | 2,6-di-Cl-4-[(2,6-di-Cl-4-$CF_3$-phenoxy)methyl]phenyl | |
| 185 | $CH_3$ | 2,6-$F_2$ | 2,6-di-Cl-4-[(2-Cl-4-$CF_3$-phenoxy)methyl]phenyl | |
| 186 | $CH_3$ | 2-Cl, 6-F | 2,6-di-Cl-4-[(2-Cl-4-$CF_3$-phenoxy)methyl]phenyl | |
| 187 | $CH_3$ | 2,6-$F_2$ | 2,6-di-Cl-4-[(4-$CF_3$-phenoxy)methyl]phenyl | |
| 188 | $CH_3$ | 2-Cl, 6-F | 2,6-di-Cl-4-[(4-$CF_3$-phenoxy)methyl]phenyl | |
| 189 | $CH_3$ | 2,6-$F_2$ | 2,6-di-Cl-4-[(4-$OCF_3$-phenoxy)methyl]phenyl | |

TABLE 2-continued

Structure: Xn-C6H4-C(=N-N(R1)-)-N=C(-R4)- (1,2,4-triazole with Xn-phenyl at one position and R4 at another, R1 on N)

| Compound No. | R¹ | Xn | R⁴ | Melting point (°C.) of refractive index ($n_D^{20}$) |
|---|---|---|---|---|
| 190 | CH₃ | 2-Cl, 6-F | 2,6-dichloro-phenyl-CH₂O-(4-OCF₃-phenyl) | |
| 191 | CH₃ | 2-Cl | 2-bromo-phenyl-CH₂O-(4-CH₃-phenyl) | |
| 192 | CH₃ | 2-Cl, 6-F | 2-bromo-phenyl-CH₂O-(4-CH₃-phenyl) | |
| 193 | CH₃ | 2,6-F₂ | 2-chloro-phenyl-CH₂O-(2,6-dichloro-4-CF₃-phenyl) | |
| 194 | CH₃ | 2-Cl, 6-F | 2-chloro-phenyl-CH₂O-(2,6-dichloro-4-CF₃-phenyl) | |
| 195 | CH₃ | 2,6-F₂ | 2-chloro-phenyl-CH₂O-(2-chloro-4-CF₃-phenyl) | |
| 196 | CH₃ | 2-Cl, 6-F | 2-chloro-phenyl-CH₂O-(2-chloro-4-CF₃-phenyl) | 113.0–114.0 |
| 197 | CH₃ | 2-Cl, 6-F | 2-chloro-phenyl-CH₂O-(2-fluoro-4-CF₃-phenyl) | 1.6010 |

TABLE 2-continued

Structure: Xn-phenyl-C(=N-)-N=N-R¹ triazole with R⁴ substituent

| Compound No. | R¹ | Xn | R⁴ | Melting point (°C.) of refractive index ($n_D^{20}$) |
|---|---|---|---|---|
| 198 | CH₃ | 2,6-F₂ | 2-Cl-4-(CH₂O-C₆H₄-4-CF₃)phenyl | |
| 199 | CH₃ | 2-Cl, 6-F | 2-Cl-4-(CH₂O-C₆H₄-4-CF₃)phenyl | 1.5961 |
| 200 | CH₃ | 2,6-F₂ | 2-Cl-4-(CH₂O-C₆H₄-4-OCF₃)phenyl | |
| 201 | CH₃ | 2-Cl, 6-F | 2-Cl-4-(CH₂O-C₆H₄-4-OCF₃)phenyl | 1.5701 |
| 202 | CH₃ | 2-Cl, 6-F | 2-Br-4-(CH₂OCH₂-C₆H₅)phenyl | |
| 203 | CH₃ | 2,6-F₂ | 3-Cl-4-(CH₂S-(2,6-Cl₂-4-CF₃-C₆H₂))phenyl | |
| 204 | CH₃ | 2-Cl, 6-F | 3-Cl-4-(CH₂S-(2,6-Cl₂-4-CF₃-C₆H₂))phenyl | |
| 205 | CH₃ | 2,6-F₂ | 3-Cl-4-(CH₂S-(2-Cl-4-CF₃-C₆H₃))phenyl | |
| 206 | CH₃ | 2-Cl, 6-F | 3-Cl-4-(CH₂S-(2-Cl-4-CF₃-C₆H₃))phenyl | |

TABLE 2-continued

Xn—[phenyl]—C(=N)—N(R¹)—N=C(R⁴)—N (1,2,4-triazole core)

| Compound No. | R¹ | Xn | R⁴ | Melting point (°C.) of refractive index (n_D^20) |
|---|---|---|---|---|
| 207 | CH₃ | 2,6-F₂ | 3-Cl-4-(2-F-4-CF₃-phenyl-CH₂S)-phenyl | |
| 208 | CH₃ | 2-Cl, 6-F | 3-Cl-4-(2-F-4-CF₃-phenyl-CH₂S)-phenyl | |
| 209 | CH₃ | 2,6-F₂ | 3-Cl-4-(4-CF₃-phenyl-CH₂S)-phenyl | |
| 210 | CH₃ | 2-Cl, 6-F | 3-Cl-4-(4-CF₃-phenyl-CH₂S)-phenyl | |
| 211 | CH₃ | 2-Cl, 6-F | 3-Cl-4-(4-Cl-phenyl-CH₂S)-phenyl | |
| 212 | CH₃ | 2,6-F₂ | 3-Cl-4-(4-OCF₃-phenyl-CH₂S)-phenyl | |
| 213 | CH₃ | 2-Cl, 6-F | 3-Cl-4-(4-OCF₃-phenyl-CH₂S)-phenyl | |
| 214 | CH₃ | 2,6-F₂ | 3-F-4-(2,6-Cl₂-4-CF₃-phenyl-CH₂S)-phenyl | |
| 215 | CH₃ | 2-Cl, 6-F | 3-F-4-(2,6-Cl₂-4-CF₃-phenyl-CH₂S)-phenyl | |

TABLE 2-continued
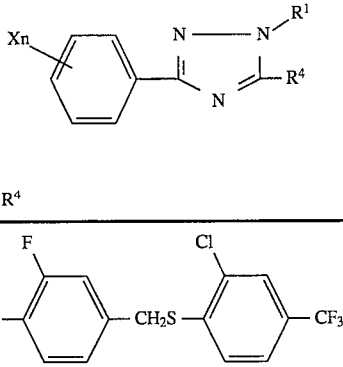
| Compound No. | R¹ | Xn | R⁴ | Melting point (°C.) of refractive index ($n_D^{20}$) |
|---|---|---|---|---|
| 216 | CH₃ | 2,6-F₂ | 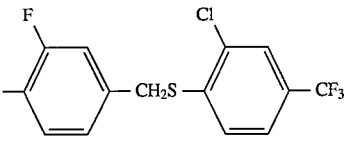 | |
| 217 | CH₃ | 2-Cl, 6-F | 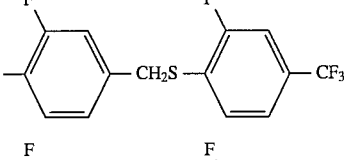 | |
| 218 | CH₃ | 2,6-F₂ | 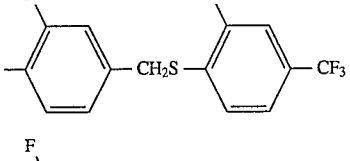 | |
| 219 | CH₃ | 2-Cl, 6-F | 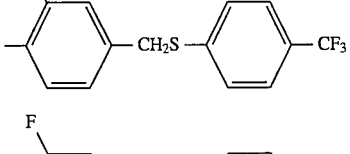 | |
| 220 | CH₃ | 2,6-F₂ | 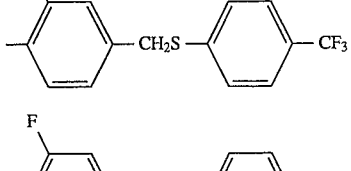 | |
| 221 | CH₃ | 2-Cl, 6-F | 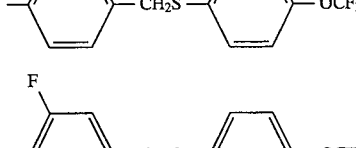 | |
| 222 | CH₃ | 2,6-F₂ | 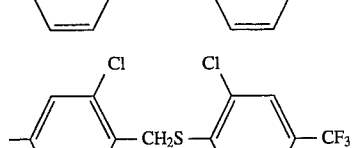 | |
| 223 | CH₃ | 2-Cl, 6-F | 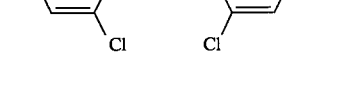 | |
| 224 | CH₃ | 2,6-F₂ | | |

TABLE 2-continued

Structure:
Xn-(phenyl)-C(=N-N(R¹)-N=C-R⁴) (triazole ring system with Xn-phenyl substituent, R¹ on one N, R⁴ on carbon)

| Compound No. | R¹ | Xn | R⁴ | Melting point (°C.) of refractive index ($n_D^{20}$) |
|---|---|---|---|---|
| 225 | CH₃ | 2-Cl, 6-F | 2,6-dichloro-phenyl-CH₂S-(2,6-dichloro-4-CF₃-phenyl) | |
| 226 | CH₃ | 2,6-F₂ | 2,6-dichloro-phenyl-CH₂S-(2-Cl-4-CF₃-phenyl) | |
| 227 | CH₃ | 2-Cl, 6-F | 2,6-dichloro-phenyl-CH₂S-(2-Cl-4-CF₃-phenyl) | |
| 228 | CH₃ | 2,6-F₂ | 2,6-dichloro-phenyl-CH₂S-(4-CF₃-phenyl) | |
| 229 | CH₃ | 2-Cl, 6-F | 2,6-dichloro-phenyl-CH₂S-(4-CF₃-phenyl) | |
| 230 | CH₃ | 2,6-F₂ | 2,6-dichloro-phenyl-CH₂S-(4-OCF₃-phenyl) | |
| 231 | CH₃ | 2-Cl, 6-F | 2,6-dichloro-phenyl-CH₂S-(4-OCF₃-phenyl) | |

TABLE 2-continued

[Structure: Xn-phenyl-triazole with R¹ on N and R⁴ on C, as shown in header]

| Compound No. | R¹ | Xn | R⁴ | Melting point (°C.) or refractive index ($n_D^{20}$) |
|---|---|---|---|---|
| 232 | CH₃ | 2,6-F₂ | 3-Cl-4-(2,6-Cl₂-4-CF₃-phenoxy)phenyl | |
| 233 | CH₃ | 2-Cl, 6-F | 3-Cl-4-(2,6-Cl₂-4-CF₃-phenoxy)phenyl | |
| 234 | CH₃ | 2,6-F₂ | 3-Cl-4-(2-Cl-4-OCF₃-phenoxy)phenyl | |
| 235 | CH₃ | 2-Cl, 6-F | 3-Cl-4-(2-Cl-4-OCF₃-phenoxy)phenyl | |
| 236 | CH₃ | 2,6-F₂ | 3-Cl-4-(4-CF₃-phenoxy)phenyl | |
| 237 | CH₃ | 2-Cl, 6-F | 3-Cl-4-(4-CF₃-phenoxy)phenyl | |
| 238 | CH₃ | 2-Cl, 6-F | 3-Cl-4-(4-Cl-phenoxy)phenyl | |
| 239 | CH₃ | 2,6-F₂ | 3-Cl-4-(4-OCF₃-phenoxy)phenyl | |
| 240 | CH₃ | 2-Cl, 6-F | 3-Cl-4-(4-OCF₃-phenoxy)phenyl | |

TABLE 2-continued
[Structure at top of table: Xn-phenyl-C(=N-)(N-N(R¹)-) with =N-R⁴ group]
| Compound No. | R¹ | Xn | R⁴ | Melting point (°C.) of refractive index ($n_D^{20}$) |
|---|---|---|---|---|
| 241 | CH₃ | 2-Cl, 6-F | 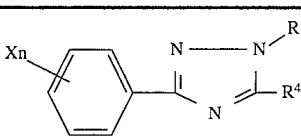 | 135.0–140.0 |
| 242 | CH₃ | 2,6-F₂ | 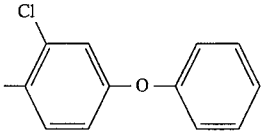 | |
| 243 | CH₃ | 2-Cl, 6-F | 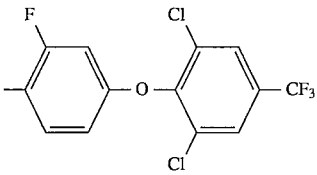 | |
| 244 | CH₃ | 2,6-F₂ | 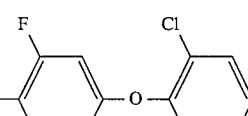 | |
| 245 | CH₃ | 2-Cl, 6-F | 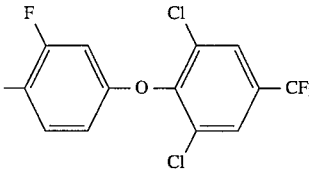 | |
| 246 | CH₃ | 2,6-F₂ | 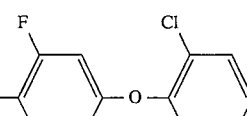 | |
| 247 | CH₃ | 2-Cl, 6-F | 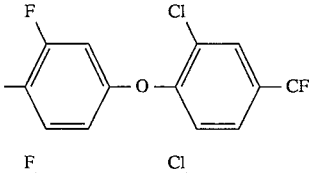 | |
| 248 | CH₃ | 2,6-F₂ | 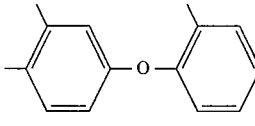 | |
| 249 | CH₃ | 2-Cl, 6-F | 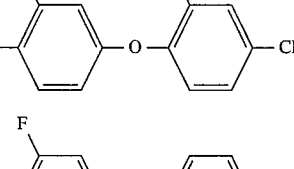 | |

TABLE 2-continued
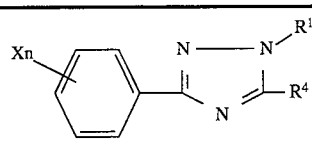
| Compound No. | $R^1$ | Xn | $R^4$ | Melting point (°C.) of refractive index ($n_D^{20}$) |
|---|---|---|---|---|
| 250 | $CH_3$ | 2,6-$F_2$ | 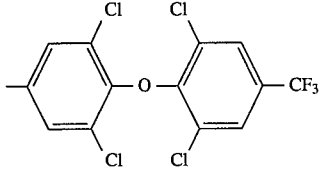 | |
| 251 | $CH_3$ | 2-Cl, 6-F | 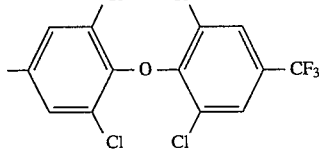 | |
| 252 | $CH_3$ | 2,6-$F_2$ | 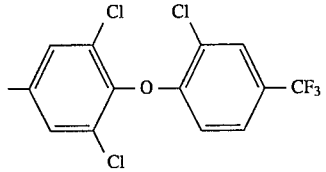 | |
| 253 | $CH_3$ | 2-Cl, 6-F | 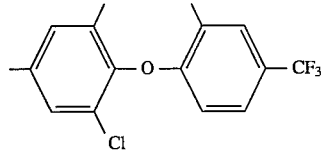 | |
| 254 | $CH_3$ | 2,6-$F_2$ | 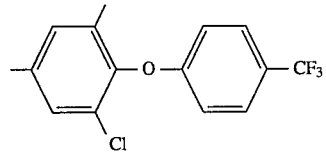 | |
| 255 | $CH_3$ | 2-Cl, 6-F | 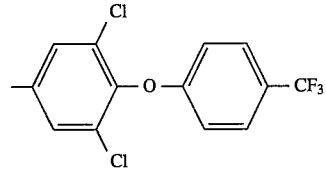 | |
| 256 | $CH_3$ | 2,6-$F_2$ | 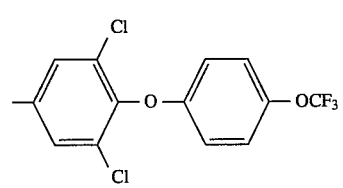 | |

TABLE 2-continued

[Structure: Xn-phenyl-triazole with N-R¹ and =N-R⁴ substituents]

| Compound No. | R¹ | Xn | R⁴ | Melting point (°C.) of refractive index (n_D^20) |
|---|---|---|---|---|
| 257 | CH₃ | 2-Cl, 6-F | 2,6-dichloro-phenyl-O-(4-OCF₃-phenyl) | |
| 258 | CH₃ | 2,6-F₂ | (2-Cl-phenyl)-O-(2,6-diCl-4-CF₃-phenyl) | |
| 259 | CH₃ | 2-Cl, 6-F | (2-Cl-phenyl)-O-(2,6-diCl-4-CF₃-phenyl) | 67.0–72.0 |
| 260 | CH₃ | 2,6-F₂ | (2-Cl-phenyl)-O-(2-Cl-4-CF₃-phenyl) | |
| 261 | CH₃ | 2-Cl, 6-F | (2-Cl-phenyl)-O-(2-Cl-4-CF₃-phenyl) | |
| 262 | CH₃ | 2,6-F₂ | (2-Cl-phenyl)-O-(4-CF₃-phenyl) | |
| 263 | CH₃ | 2-Cl, 6-F | (2-Cl-phenyl)-O-(4-CF₃-phenyl) | |
| 264 | CH₃ | 2,6-F₂ | (2-Cl-phenyl)-O-(4-OCF₃-phenyl) | |
| 265 | CH₃ | 2-Cl, 6-F | (2-Cl-phenyl)-O-(4-OCF₃-phenyl) | |

TABLE 2-continued

[Structure: Xn-phenyl-triazole with N-N-R¹, N, and R⁴ substituents]

| Compound No. | R¹ | Xn | R⁴ | Melting point (°C.) of refractive index ($n_D^{20}$) |
|---|---|---|---|---|
| 266 | CH₃ | 2-Cl, 6-F | [2-Cl-phenyl-OCH₂-4-CH₃-phenyl] | |
| 267 | CH₃ | 2-Cl, 6-F | [2,6-diCl-phenyl-OCH₂-2-Cl-4-CF₃-phenyl] | 101.0–107.0 |
| 268 | CH₃ | 2-Cl, 6-F | [2,6-diCl-phenyl-OCH₂-4-CF₃-phenyl] | 115.0–120.0 |
| 269 | CH₃ | 2-Cl, 6-F | [2,6-diCl-phenyl-OCH₂-4-OCF₃-phenyl] | 74.0–77.0 |
| 270 | CH₃ | 2-Cl | [2-Cl-phenyl-OCH₂-pentafluorophenyl] | |
| 271 | CH₃ | 2-Cl, 6-F | [2-Cl-phenyl-OCH₂-pentafluorophenyl] | |
| 272 | CH₃ | 2-Cl, 6-F | [2-Cl-phenyl-OCH₂-2,4,6-triCl-phenyl] | |
| 273 | CH₃ | 2-Cl, 6-F | [2-Cl-phenyl-OCH₂-2-Cl-4-CF₃-phenyl] | 156.0–159.0 |

TABLE 2-continued

Structure: Xn-phenyl-C(=N-)-N(R1)-N=CH-R4 (triazole-type), with N in ring

| Compound No. | R¹ | Xn | R⁴ | Melting point (°C.) of refractive index ($n_D^{20}$) |
|---|---|---|---|---|
| 274 | CH₃ | 2-Cl, 6-F | 2-Cl-6-(2-F-4-CF₃-phenyl-methoxy)phenyl (-C₆H₃(Cl)-OCH₂-C₆H₃(F)(CF₃)) | 109.0–111.0 |
| 275 | CH₃ | 2-Cl, 6-F | 2-Cl-(4-CF₃-phenyl-methoxy)phenyl (-C₆H₃(Cl)-OCH₂-C₆H₄-CF₃) | 43.0–47.0 |
| 276 | CH₃ | 2,6-F₂ | 2-Cl-(4-CF₃-phenyl-methoxy)phenyl | 171.0–177.0 |
| 277 | CH₃ | 2-Cl, 6-F | 2-Cl-(4-OCF₃-phenyl-methoxy)phenyl | 1.5680 |
| 278 | CH₃ | 2,6-F₂ | 2-Cl-(4-OCF₃-phenyl-methoxy)phenyl | 132.0–136.0 |
| 279 | CH₃ | 2-Cl, 6-F | 2-F-(4-OCH₃-phenyl-methoxy)phenyl | |
| 280 | CH₃ | 2-Cl | 2-Cl-4-(phenylthio)phenyl | |
| 281 | CH₃ | 2-Cl, 6-F | 2-Cl-4-(4-Cl-phenyl-methylthio)phenyl | |
| 282 | CH₃ | 2-Cl | 2-Cl-4-(pyridin-4-yloxy)phenyl | |

TABLE 2-continued

Structure: Xn-phenyl-triazole with R¹ on N, R⁴ substituent

| Compound No. | R¹ | Xn | R⁴ | Melting point (°C.) of refractive index ($n_D^{20}$) |
|---|---|---|---|---|
| 283 | CH₃ | 2-Cl, 6-F | 3-chloro-4-(pyridin-4-yloxy)phenyl | |
| 284 | CH₃ | 2-Cl | 2-bromo-4-[(E)-2-(pyridin-3-yl)vinyl]phenyl | |
| 285 | CH₃ | 2-Cl, 6-F | 2-bromo-4-[(E)-2-(pyridin-3-yl)vinyl]phenyl | |
| 286 | CH₃ | 2,6-F₂ | 3-chloro-4-[(6-chloropyridin-3-yl)oxymethyl]phenyl | |
| 287 | CH₃ | 2-Cl, 6-F | 3-chloro-4-[(6-chloropyridin-3-yl)oxymethyl]phenyl | |
| 288 | CH₃ | 2,6-F₂ | 3-fluoro-4-[(6-chloropyridin-3-yl)methoxy]phenyl | |
| 289 | CH₃ | 2-Cl, 6-F | 3-fluoro-4-[(6-chloropyridin-3-yl)methoxy]phenyl | |
| 290 | CH₃ | 2,6-F₂ | 3,5-dichloro-4-[(6-chloropyridin-3-yl)methoxy]phenyl | |
| 291 | CH₃ | 2-Cl, 6-F | 3,5-dichloro-4-[(6-chloropyridin-3-yl)methoxy]phenyl | |

TABLE 2-continued

Structure: Xn-phenyl-C(=N-N(R¹)-N=C-R⁴) (1,2,4-triazole with Xn-aryl and R⁴ substituents; R¹ on N)

| Compound No. | R¹ | Xn | R⁴ | Melting point (°C.) of refractive index ($n_D^{20}$) |
|---|---|---|---|---|
| 292 | CH₃ | 2,6-F₂ | 2-Cl-phenyl-OCH₂-(6-Cl-pyridin-3-yl) | |
| 293 | CH₃ | 2-Cl, 6-F | 2-Cl-phenyl-OCH₂-(6-Cl-pyridin-3-yl) | |
| 294 | CH₃ | 2,6-F₂ | 2-F-phenyl-OCH₂-(6-Cl-pyridin-3-yl) | |
| 295 | CH₃ | 2-Cl, 6-F | 2-F-phenyl-OCH₂-(6-Cl-pyridin-3-yl) | |
| 296 | CH₃ | 2-Cl | 2-Cl-phenyl-SCH₂-(6-Cl-pyridin-3-yl) | |
| 297 | CH₃ | 2-Cl, 6-F | 2-Cl-phenyl-SCH₂-(6-Cl-pyridin-3-yl) | |
| 298 | CH₃ | 2,6-F₂ | 2-Cl-phenyl-SCH₂-(6-Cl-pyridin-3-yl) | |
| 299 | CH₃ | 2-Cl, 6-F | 2-Cl-phenyl-SCH₂-(6-Cl-pyridin-3-yl) | |
| 300 | CH₃ | 2,6-F₂ | 2,6-di-Cl-phenyl-SCH₂-(6-Cl-pyridin-3-yl) | |

TABLE 2-continued

[Structure: Xn-phenyl-triazole with R¹ and R⁴ substituents]

| Compound No. | R¹ | Xn | R⁴ | Melting point (°C.) of refractive index ($n_D^{20}$) |
|---|---|---|---|---|
| 301 | CH₃ | 2-Cl, 6-F | 2,6-dichlorophenyl-SCH₂-(6-chloropyridin-3-yl) | |
| 302 | CH₃ | 2,6-F₂ | 2,6-dichlorophenyl-CH₂CH₂O-(5-trifluoromethylpyridin-2-yl) | |
| 303 | CH₃ | 2-Cl, 6-F | 2-chlorophenyl-CH₂CH₂O-(5-trifluoromethylpyridin-2-yl) | |
| 304 | CH₃ | 2,6-F₂ | 2-chlorophenyl-CH₂CH₂O-(3-chloro-5-trifluoromethylpyridin-2-yl) | |
| 305 | CH₃ | 2-Cl, 6-F | 2-chlorophenyl-CH₂CH₂O-(3-chloro-5-trifluoromethylpyridin-2-yl) | |
| 306 | CH₃ | 2,6-F₂ | 2-chlorophenyl-CH₂CH₂O-(3,5-bis(trifluoromethyl)pyridin-2-yl) | |
| 307 | CH₃ | 2-Cl, 6-F | 2-chlorophenyl-CH₂CH₂O-(3,5-bis(trifluoromethyl)pyridin-2-yl) | |
| 308 | CH₃ | 2,6-F₂ | 2-chlorophenyl-CH₂O-(3,5-bis(trifluoromethyl)pyridin-2-yl) | |
| 309 | CH₃ | 2-Cl, 6-F | 2-chlorophenyl-CH₂O-(3,5-bis(trifluoromethyl)pyridin-2-yl) | |

TABLE 2-continued

[Structure: Xn-phenyl-triazole with N-R¹ and =CH-R⁴ substituents]

| Compound No. | R¹ | Xn | R⁴ | Melting point (°C.) of refractive index ($n_D^{20}$) |
|---|---|---|---|---|
| 310 | CH₃ | 2,6-F₂ | 4-Cl-benzyl-O-(3-Cl-5-CF₃-pyridin-2-yl) | |
| 311 | CH₃ | 2-Cl, 6-F | 4-Cl-benzyl-O-(3-Cl-5-CF₃-pyridin-2-yl) | 135.0–139.0 |
| 312 | CH₃ | 2,6-F₂ | 4-Cl-benzyl-O-(5-CF₃-pyridin-2-yl) | |
| 313 | CH₃ | 2-Cl, 6-F | 4-Cl-benzyl-O-(5-CF₃-pyridin-2-yl) | 109.0–112.0 |
| 314 | CH₃ | 2,6-F₂ | 3-Cl-benzyl-O-(3-CF₃-5-CF₃-pyridin-2-yl) | |
| 315 | CH₃ | 2-Cl, 6-F | 3-Cl-benzyl-O-(3-CF₃-5-CF₃-pyridin-2-yl) | |
| 316 | CH₃ | 2,6-F₂ | 3-Cl-benzyl-O-(3-Cl-5-CF₃-pyridin-2-yl) | |
| 317 | CH₃ | 2-Cl, 6-F | 3-Cl-benzyl-O-(3-Cl-5-CF₃-pyridin-2-yl) | not measurable |
| 318 | CH₃ | 2,6-F₂ | 3-Cl-benzyl-O-(5-CF₃-pyridin-2-yl) | |

TABLE 2-continued

[Structure: Xn-phenyl-C(=N-N(R¹)-)-N=C-R⁴ (triazole ring)]

| Compound No. | R¹ | Xn | R⁴ | Melting point (°C.) of refractive index ($n_D^{20}$) |
|---|---|---|---|---|
| 319 | $CH_3$ | 2-Cl, 6-F | 5-chloro-2-[(5-trifluoromethylpyridin-2-yl)oxymethyl]phenyl (Cl ortho, CH₂O-pyridine-CF₃) | 1.5698 |
| 320 | $CH_3$ | 2-Cl, 6-F | 4-fluoro-2-[(3-chloro-5-chloropyridin-2-yl)oxymethyl]phenyl | 123.5–126.0 |
| 321 | $CH_3$ | 2-Cl, 6-F | 4-fluoro-2-[(3-chloro-5-trifluoromethylpyridin-2-yl)oxymethyl]phenyl | 1.5638 |
| 322 | $CH_3$ | 2-Cl, 6-F | 4-fluoro-2-[(5-trifluoromethylpyridin-2-yl)oxymethyl]phenyl | 137.0–141.0 |
| 323 | $CH_3$ | 2,6-$F_2$ | 2,6-dichloro-[(3-chloro-5-trifluoromethylpyridin-2-yl)oxymethyl]phenyl | |
| 324 | $CH_3$ | 2-Cl, 6-F | 2,6-dichloro-[(3-chloro-5-trifluoromethylpyridin-2-yl)oxymethyl]phenyl | |
| 325 | $CH_3$ | 2,6-$F_2$ | 2,6-dichloro-[(5-trifluoromethylpyridin-2-yl)oxymethyl]phenyl | |
| 326 | $CH_3$ | 2-Cl, 6-F | 2,6-dichloro-[(5-trifluoromethylpyridin-2-yl)oxymethyl]phenyl | |

TABLE 2-continued

[Structure: Xn-phenyl-C(=N-)-N=N(R¹)-C(=)-R⁴ triazole system]

| Compound No. | R¹ | Xn | R⁴ | Melting point (°C.) of refractive index ($n_D^{20}$) |
|---|---|---|---|---|
| 327 | CH₃ | 2-Cl, 6-F | 2-Br, 3-Cl-5-CF₃-pyridin-2-yloxymethyl-phenyl | |
| 328 | CH₃ | 2,6-F₂ | 2-Cl, 3-CF₃-5-CF₃-pyridin-2-yloxymethyl-phenyl | |
| 329 | CH₃ | 2-Cl, 6-F | 2-Cl, 3-CF₃-5-CF₃-pyridin-2-yloxymethyl-phenyl | |
| 330 | CH₃ | 2-Cl, 6-F | 2-Cl, 3-Cl-5-Cl-pyridin-2-yloxymethyl-phenyl | 153.0–155.0 |
| 331 | CH₃ | 2,6-F₂ | 2-Cl, 3-Cl-5-CF₃-pyridin-2-yloxymethyl-phenyl | |
| 332 | CH₃ | 2-Cl, 6-F | 2-Cl, 3-Cl-5-CF₃-pyridin-2-yloxymethyl-phenyl | 47.0–49.0 |
| 333 | CH₃ | 2,6-F₂ | 2-Cl, 5-CF₃-pyridin-2-yloxymethyl-phenyl | |
| 334 | CH₃ | 2-Cl, 6-F | 2-Cl, 5-CF₃-pyridin-2-yloxymethyl-phenyl | 1.5879 |
| 335 | CH₃ | 2,6-F₂ | 2-F, 3-CF₃-5-CF₃-pyridin-2-yloxymethyl-phenyl | |

TABLE 2-continued

Structure: Xn-phenyl-triazole with N-R¹ and R⁴ substituents

| Compound No. | R¹ | Xn | R⁴ | Melting point (°C.) of refractive index ($n_D^{20}$) |
|---|---|---|---|---|
| 336 | CH₃ | 2-Cl, 6-F | 2-F-phenyl-CH₂O-(3-CF₃, 5-CF₃-pyridin-2-yl) | |
| 337 | CH₃ | 2,6-F₂ | 2-F-phenyl-CH₂O-(3-Cl, 5-CF₃-pyridin-2-yl) | |
| 338 | CH₃ | 2-Cl, 6-F | 2-F-phenyl-CH₂O-(3-Cl, 5-CF₃-pyridin-2-yl) | 88.0–90.0 |
| 339 | CH₃ | 2,6-F₂ | 2-F-phenyl-CH₂O-(5-CF₃-pyridin-2-yl) | |
| 340 | CH₃ | 2-Cl, 6-F | 2-F-phenyl-CH₂O-(5-CF₃-pyridin-2-yl) | |
| 341 | CH₃ | 2-Cl | 2-Br-phenyl-CH₂OCH₂-phenyl | |
| 342 | CH₃ | 2-Cl, 6-F | 2-Br-phenyl-CH₂OCH₂-phenyl | |
| 343 | CH₃ | 2-Cl | 2-Br-phenyl-CH₂OCH₂-(5-Cl-pyridin-2-yl) | |
| 344 | CH₃ | 2-Cl, 6-F | 2-Br-phenyl-CH₂OCH₂-(5-Cl-pyridin-2-yl) | |

TABLE 2-continued

[Structure: Xn-phenyl-triazole with N-R¹ and =R⁴ substituents]

| Compound No. | R¹ | Xn | R⁴ | Melting point (°C.) of refractive index (n_D^20) |
|---|---|---|---|---|
| 345 | CH₃ | 2-Cl, 6-F | 2-Cl-phenyl-CH₂OCH₂-(3-Cl,5-CF₃-pyridin-2-yl) | 109.5–112.0 |
| 346 | CH₃ | 2-Cl, 6-F | 2-F-phenyl-CH₂OCH₂-(3-Cl,5-CF₃-pyridin-2-yl) | |
| 347 | CH₃ | 2,6-F₂ | 3-Cl-phenyl-CH₂S-(3-Cl,5-CF₃-pyridin-2-yl) | |
| 348 | CH₃ | 2-Cl, 6-F | 3-Cl-phenyl-CH₂S-(3-Cl,5-CF₃-pyridin-2-yl) | |
| 349 | CH₃ | 2,6-F₂ | 3-Cl-phenyl-CH₂S-(5-CF₃-pyridin-2-yl) | |
| 350 | CH₃ | 2-Cl, 6-F | 3-Cl-phenyl-CH₂S-(5-CF₃-pyridin-2-yl) | |
| 351 | CH₃ | 2-Cl | 3-Cl-phenyl-CH₂S-(5-Cl-pyridin-2-yl) | |
| 352 | CH₃ | 2-Cl, 6-F | 3-Cl-phenyl-CH₂S-(5-Cl-pyridin-2-yl) | |
| 353 | CH₃ | 2,6-F₂ | 3-F-phenyl-CH₂S-(3-Cl,5-CF₃-pyridin-2-yl) | |

TABLE 2-continued

[Structure: Xn-phenyl-triazole with R¹ on N and R⁴ substituent]

| Compound No. | R¹ | Xn | R⁴ | Melting point (°C.) or refractive index ($n_D^{20}$) |
|---|---|---|---|---|
| 354 | CH₃ | 2-Cl, 6-F | 3-F-phenyl-CH₂S-(3-Cl, 5-CF₃-pyridin-2-yl) | |
| 355 | CH₃ | 2,6-F₂ | 3-F-phenyl-CH₂S-(5-CF₃-pyridin-2-yl) | |
| 356 | CH₃ | 2-Cl, 6-F | 3-F-phenyl-CH₂S-(5-CF₃-pyridin-2-yl) | |
| 357 | CH₃ | 2,6-F₂ | 2,6-Cl₂-phenyl-CH₂S-(3-Cl, 5-CF₃-pyridin-2-yl) | |
| 358 | CH₃ | 2-Cl, 6-F | 2,6-Cl₂-phenyl-CH₂S-(3-Cl, 5-CF₃-pyridin-2-yl) | |
| 359 | CH₃ | 2,6-F₂ | 2,6-Cl₂-phenyl-CH₂S-(5-CF₃-pyridin-2-yl) | |
| 360 | CH₃ | 2-Cl, 6-F | 2,6-Cl₂-phenyl-CH₂S-(5-CF₃-pyridin-2-yl) | |
| 361 | CH₃ | 2,6-F₂ | 2-Cl-phenyl-CH₂S-(3-CF₃, 5-CF₃-pyridin-2-yl) | |

TABLE 2-continued

Structure: Xn-phenyl-triazole with N-R¹, N, and R⁴ substituents

| Compound No. | R¹ | Xn | R⁴ | Melting point (°C.) or refractive index ($n_D^{20}$) |
|---|---|---|---|---|
| 362 | CH₃ | 2-Cl, 6-F | -C₆H₃(Cl)-CH₂S-pyridyl(CF₃)(CF₃) | |
| 363 | CH₃ | 2,6-F₂ | -C₆H₃(Cl)-CH₂S-pyridyl(Cl)(CF₃) | |
| 364 | CH₃ | 2-Cl, 6-F | -C₆H₃(Cl)-CH₂S-pyridyl(Cl)(CF₃) | |
| 365 | CH₃ | 2,6-F₂ | -C₆H₃(Cl)-CH₂S-pyridyl(CF₃) | |
| 366 | CH₃ | 2-Cl, 6-F | -C₆H₃(Cl)-CH₂S-pyridyl(CF₃) | |
| 367 | CH₃ | 2,6-F₂ | -C₆H₃(F)-CH₂S-pyridyl(CF₃)(CF₃) | |
| 368 | CH₃ | 2-Cl, 6-F | -C₆H₃(F)-CH₂S-pyridyl(CF₃)(CF₃) | |
| 369 | CH₃ | 2,6-F₂ | -C₆H₃(F)-CH₂S-pyridyl(Cl)(CF₃) | |
| 370 | CH₃ | 2-Cl, 6-F | -C₆H₃(F)-CH₂S-pyridyl(Cl)(CF₃) | |

TABLE 2-continued

Structure: Xn-phenyl-triazole with N-R¹, =N-R⁴ substituents

| Compound No. | R¹ | Xn | R⁴ | Melting point (°C.) or refractive index ($n_D^{20}$) |
|---|---|---|---|---|
| 371 | CH₃ | 2,6-F₂ | 2-F-4-(CH₂S-(5-CF₃-pyridin-2-yl))phenyl | |
| 372 | CH₃ | 2-Cl, 6-F | 2-F-4-(CH₂S-(5-CF₃-pyridin-2-yl))phenyl | |
| 373 | CH₃ | 2-Cl, 6-F | 4-F-phenyl-O-(3,5-bis(CF₃)-pyridin-2-yl) ether | 1.5391 |
| 374 | CH₃ | 2-Cl, 6-F | 4-F-phenyl-O-(5-CH₃-pyridin-2-yl) ether | 108.0–111.0 |
| 375 | CH₃ | 2,6-F₂ | 2-Cl-phenyl-O-(3-Cl-5-CF₃-pyridin-2-yl) ether | |
| 376 | CH₃ | 2-Cl, 6-F | 2-Cl-phenyl-O-(3-Cl-5-CF₃-pyridin-2-yl) ether | 58.0–62.0 |
| 377 | CH₃ | 2,6-F₂ | 2-Cl-phenyl-O-(5-CF₃-pyridin-2-yl) ether | not measurable |
| 378 | CH₃ | 2-Cl, 6-F | 2-Cl-phenyl-O-(5-CF₃-pyridin-2-yl) ether | not measurable |

TABLE 2-continued

[Structure: Xn-phenyl-triazole with R¹ on N and R⁴]

| Compound No. | R¹ | Xn | R⁴ | Melting point (°C.) of refractive index ($n_D^{20}$) |
|---|---|---|---|---|
| 379 | CH₃ | 2,6-F₂ | 3-OC₂H₅-phenyl-O-(3-Cl-5-CF₃-pyridin-2-yl) | |
| 380 | CH₃ | 2-Cl, 6-F | 3-OC₂H₅-phenyl-O-(3-Cl-5-CF₃-pyridin-2-yl) | |
| 381 | CH₃ | 2,6-F₂ | 3-OC₂H₅-phenyl-O-(5-CF₃-pyridin-2-yl) | |
| 382 | CH₃ | 2-Cl, 6-F | 3-OC₂H₅-phenyl-O-(5-CF₃-pyridin-2-yl) | |
| 383 | CH₃ | 2,6-F₂ | 3-Cl-phenyl-O-(3-CF₃-5-CF₃-pyridin-2-yl) | |
| 384 | CH₃ | 2-Cl, 6-F | 3-Cl-phenyl-O-(3-CF₃-5-CF₃-pyridin-2-yl) | |
| 385 | CH₃ | 2,6-F₂ | 3-Cl-phenyl-O-(3-Cl-5-Cl-pyridin-2-yl) | |
| 386 | CH₃ | 2-Cl, 6-F | 3-Cl-phenyl-O-(3-Cl-5-Cl-pyridin-2-yl) | |

TABLE 2-continued $$\text{Xn} \underset{}{\overset{}{\diagdown}} \text{—} \underset{N}{\overset{N-N}{\diagdown}} \overset{R^1}{\underset{R^4}{\diagdown}}$$

| Compound No. | R¹ | Xn | R⁴ | Melting point (°C.) of refractive index ($n_D^{20}$) |
|---|---|---|---|---|
| 387 | $CH_3$ | 2,6-$F_2$ | [3-Cl-4-yl phenoxy-(3-Cl-5-CF₃-pyridin-2-yl)] | |
| 388 | $CH_3$ | 2-Cl, 6-F | [3-Cl-4-yl phenoxy-(3-Cl-5-CF₃-pyridin-2-yl)] | |
| 389 | $CH_3$ | 2-Cl | [3-Cl-4-yl phenoxy-(5-CF₃-pyridin-2-yl)] | 104.0–108.0 |
| 390 | $CH_3$ | 2-Cl, 6-F | [3-Cl-4-yl phenoxy-(5-CF₃-pyridin-2-yl)] | 139.0–141.0 |
| 391 | $CH_3$ | 2-Cl, 6-F | [3-F-4-yl phenoxy-(5-CF₃-pyridin-2-yl)] | 110.0–112.0 |
| 392 | $CH_3$ | 2,6-$F_2$ | [3-F-4-yl phenoxy-(3-CF₃-5-CF₃-pyridin-2-yl)] | |
| 393 | $CH_3$ | 2-Cl, 6-F | [3-F-4-yl phenoxy-(3-CF₃-5-CF₃-pyridin-2-yl)] | |
| 394 | $CH_3$ | 2,6-$F_2$ | [3-F-4-yl phenoxy-(3-Cl-5-CF₃-pyridin-2-yl)] | |
| 395 | $CH_3$ | 2-Cl, 6-F | [3-F-4-yl phenoxy-(3-Cl-5-CF₃-pyridin-2-yl)] | 127.0–132.0 |

TABLE 2-continued

Structure: Xn-phenyl-C(=N-N(R¹)-N=CR⁴)-... (triazole-type with phenyl bearing Xn substituents and R⁴ group)

| Compound No. | R¹ | Xn | R⁴ | Melting point (°C.) of refractive index ($n_D^{20}$) |
|---|---|---|---|---|
| 396 | CH₃ | 2,6-F₂ | 2,6-dichloro-phenoxy-(3-CF₃, 5-CF₃)-pyridin-2-yl | |
| 397 | CH₃ | 2-Cl, 6-F | 2,6-dichloro-phenoxy-(3-CF₃, 5-CF₃)-pyridin-2-yl | |
| 398 | CH₃ | 2,6-F₂ | 2,6-dichloro-phenoxy-(3-Cl, 5-Cl)-pyridin-2-yl | |
| 399 | CH₃ | 2-Cl, 6-F | 2,6-dichloro-phenoxy-(3-Cl, 5-Cl)-pyridin-2-yl | |
| 400 | CH₃ | 2,6-F₂ | 2,6-dichloro-phenoxy-(3-Cl, 5-CF₃)-pyridin-2-yl | 129.0–130.0 |
| 401 | CH₃ | 2-Cl, 6-F | 2,6-dichloro-phenoxy-(3-Cl, 5-CF₃)-pyridin-2-yl | not measurable |
| 402 | CH₃ | 2,6-F₂ | 2,6-dichloro-phenoxy-(5-CF₃)-pyridin-2-yl | |

TABLE 2-continued

[Structure: Xn-phenyl-triazole with N-R¹ and R⁴ substituents]

| Compound No. | R¹ | Xn | R⁴ | Melting point (°C.) of refractive index (n_D^20) |
|---|---|---|---|---|
| 403 | CH₃ | 2-Cl | 2,6-dichlorophenoxy-5-(trifluoromethyl)pyridine | 150.0–152.0 |
| 404 | CH₃ | 2-Cl, 6-F | 2,6-dichlorophenoxy-5-(trifluoromethyl)pyridine | 149.0–151.5 |
| 405 | CH₃ | 2,6-F₂ | 2-bromophenoxy-5-(trifluoromethyl)pyridine | |
| 406 | CH₃ | 2-Cl, 6-F | 2-bromophenoxy-5-(trifluoromethyl)pyridine | 140.0–144.0 |
| 407 | CH₃ | 2,6-F₂ | 2-chlorophenoxy-3-(trifluoromethyl)-5-(trifluoromethyl)pyridine | |
| 408 | CH₃ | 2-Cl, 6-F | 2-chlorophenoxy-3-(trifluoromethyl)-5-(trifluoromethyl)pyridine | |
| 409 | CH₃ | 2,6-F₂ | 2-chlorophenoxy-3-chloro-5-(trifluoromethyl)pyridine | not measurable |
| 410 | CH₃ | 2-Cl, 6-F | 2-chlorophenoxy-3-chloro-5-(trifluoromethyl)pyridine | not measurable |
| 411 | CH₃ | 2,3,4,5,6-F₅ | 2-chlorophenoxy-5-(trifluoromethyl)pyridine | |

TABLE 2-continued
$$\underset{Xn}{\diagdown}\hspace{-0.3em}\text{Ar}\hspace{-0.3em}-\hspace{-0.3em}\overset{N-N}{\underset{N}{\diagdown}}\hspace{-0.3em}\overset{R^1}{\diagdown}R^4$$
| Compound No. | R$^1$ | Xn | R$^4$ | Melting point (°C.) of refractive index (n$_D^{20}$) |
|---|---|---|---|---|
| 412 | CH$_3$ | 2,6-F$_2$ | 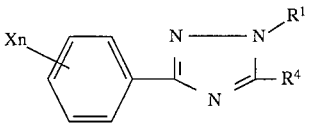 | not measurable |
| 413 | CH$_3$ | 2-Cl, 6-F | 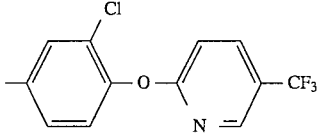 | 116.0–117.0 |
| 414 | CH$_3$ | 2,6-F$_2$ | 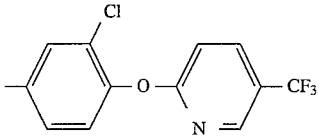 | |
| 415 | CH$_3$ | 2-Cl, 6-F | 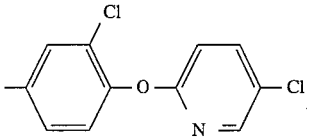 | |
| 416 | CH$_3$ | 2,6-F$_2$ | 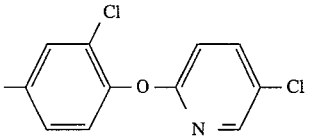 | |
| 417 | CH$_3$ | 2-Cl, 6-F | 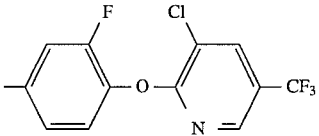 | |
| 418 | CH$_3$ | 2,6-F$_2$ | 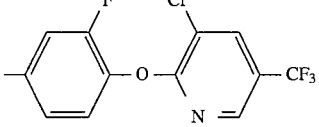 | |
| 419 | CH$_3$ | 2-Cl, 6-F | 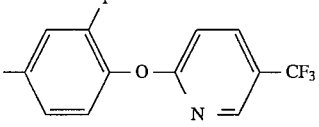 | 120.0–123.0 |
| 420 | CH$_3$ | 2-Cl | 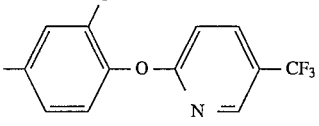 | |

TABLE 2-continued

[Structure: Xn-phenyl-triazole with N-N-R¹ and R⁴ substituents]

| Compound No. | R¹ | Xn | R⁴ | Melting point (°C.) of refractive index ($n_D^{20}$) |
|---|---|---|---|---|
| 421 | CH₃ | 2-Cl, 6-F | 3-F-phenyl-OCH₂-(3-Cl-5-CF₃-pyridin-2-yl) | |
| 422 | CH₃ | 2-Cl | 3-Cl-phenyl-OCH₂-(5-Cl-pyridin-2-yl) | |
| 423 | CH₃ | 2-Cl, 6-F | 3-Cl-phenyl-OCH₂-(5-Cl-pyridin-2-yl) | |
| 424 | CH₃ | 2-Cl | 3-Br-phenyl-OCH₂-(5-CF₃-pyridin-2-yl) | |
| 425 | CH₃ | 2-Cl, 6-F | 3-Br-phenyl-OCH₂-(5-CF₃-pyridin-2-yl) | |
| 426 | CH₃ | 2-Cl, 6-F | 3-Cl-phenyl-OCH₂-(3-Cl-5-CF₃-pyridin-2-yl) | |
| 427 | CH₃ | 2-Cl, 6-F | 3-F-phenyl-OCH₂-(3-Cl-5-C₂H₅-pyridin-2-yl) | |
| 428 | CH₃ | 2-Cl, 6-F | 3-F-phenyl-OCH₂-(3-Cl-5-C₃H₇-pyridin-2-yl) | |
| 429 | CH₃ | 2-Cl, 6-F | 3-F-phenyl-OCH₂-(3-Cl-5-CF₃-pyridin-2-yl) | |

TABLE 2-continued
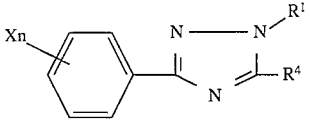
| Compound No. | R¹ | Xn | R⁴ | Melting point (°C.) of refractive index ($n_D^{20}$) |
|---|---|---|---|---|
| 430 | CH₃ | 2,6-F₂ | 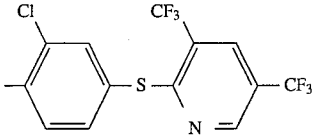 | |
| 431 | CH₃ | 2-Cl, 6-F | 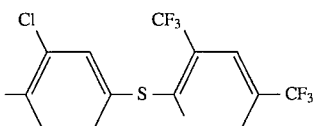 | |
| 432 | CH₃ | 2,6-F₂ | 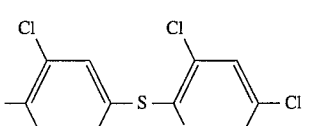 | |
| 433 | CH₃ | 2-Cl, 6-F | 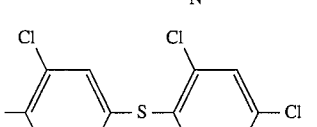 | |
| 434 | CH₃ | 2,6-F₂ | 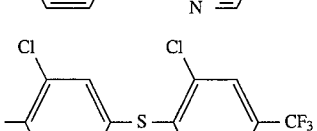 | |
| 435 | CH₃ | 2-Cl, 6-F | 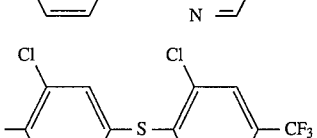 | |
| 436 | CH₃ | 2,6-F₂ | 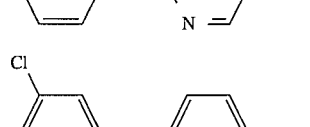 | |
| 437 | CH₃ | 2-Cl, 6-F | 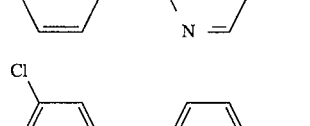 | |
| 438 | CH₃ | 2,6-F₂ | 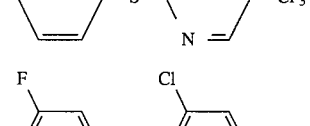 | |

TABLE 2-continued
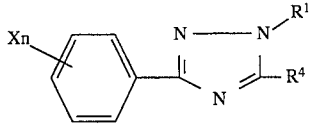
| Compound No. | R¹ | Xn | R⁴ | Melting point (°C.) of refractive index ($n_D^{20}$) |
|---|---|---|---|---|
| 439 | CH₃ | 2-Cl, 6-F | 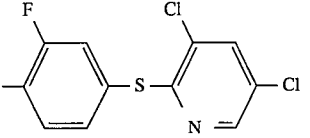 | |
| 440 | CH₃ | 2,6-F₂ | 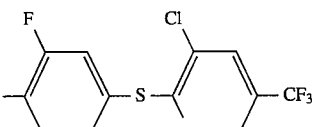 | |
| 441 | CH₃ | 2-Cl, 6-F | 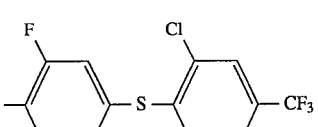 | |
| 442 | CH₃ | 2,6-F₂ | 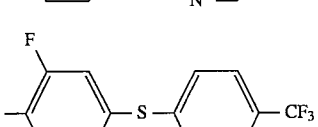 | |
| 443 | CH₃ | 2-Cl, 6-F | 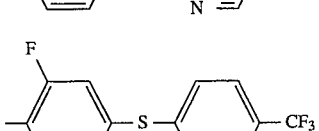 | |
| 444 | CH₃ | 2,6-F₂ | 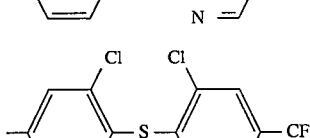 | |
| 445 | CH₃ | 2-Cl, 6-F | 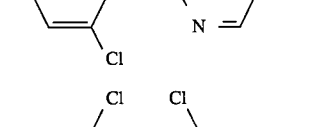 | |
| 446 | CH₃ | 2,6-F₂ | 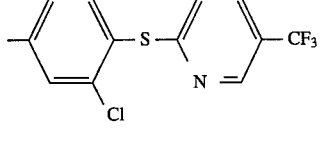 | |

TABLE 2-continued

[Structure: Xn-phenyl-triazole with N-R¹ and =N-R⁴ substituents]

| Compound No. | R¹ | Xn | R⁴ | Melting point (°C.) of refractive index ($n_D^{20}$) |
|---|---|---|---|---|
| 447 | CH₃ | 2-Cl, 6-F | 2,6-dichlorophenyl-S-(5-CF₃-pyridin-2-yl) | |
| 448 | CH₃ | 2,6-F₂ | 2-Cl-phenyl-S-(3-Cl-5-CF₃-pyridin-2-yl) | |
| 449 | CH₃ | 2-Cl, 6-F | 2-Cl-phenyl-S-(3-Cl-5-CF₃-pyridin-2-yl) | |
| 450 | CH₃ | 2,6-F₂ | 2-C₄F₉-phenyl-CH₂O-(3-Cl-5-CF₃-pyridin-2-yl) | |
| 451 | CH₃ | 2-Cl, 6-F | 2-C₄F₉-phenyl-CH₂O-(3-Cl-5-CF₃-pyridin-2-yl) | 123.0–127.0 |
| 452 | CH₃ | 2,6-F₂ | 2-C₄F₉-phenyl-CH₂O-(5-CF₃-pyridin-2-yl) | |
| 453 | CH₃ | 2-Cl, 6-F | 2-C₄F₉-phenyl-CH₂O-(5-CF₃-pyridin-2-yl) | 1.5020 |
| 454 | CH₃ | 2,6-F₂ | 2-CH₂CF₃-phenyl-CH₂O-(3-Cl-5-CF₃-pyridin-2-yl) | |
| 455 | CH₃ | 2-Cl, 6-F | 2-CH₂CF₃-phenyl-CH₂O-(3-Cl-5-CF₃-pyridin-2-yl) | |

TABLE 2-continued

[Structure: Xn-phenyl-triazole with N-N-R¹ and N=C-R⁴]

| Compound No. | R¹ | Xn | R⁴ | Melting point (°C.) of refractive index ($n_D^{20}$) |
|---|---|---|---|---|
| 456 | CH₃ | 2-Cl, 6-F | [3-CH₃-4'-OCF₃-biphenyl] | 78.0–83.0 |
| 457 | CH₃ | 2-Cl, 6-F | [2-CH₃-4'-OCF₃-biphenyl] | 117.0–122.0 |
| 458 | CH₃ | 2-Cl, 6-F | [2-CH₃-phenyl with C≡C-phenyl] | |
| 459 | CH₃ | 2,6-F₂ | [2-OCH₃-phenyl-CH₂O-4-CF₃-phenyl] | |
| 460 | CH₃ | 2-Cl, 6-F | [2-OCH₃-phenyl-CH₂O-4-CF₃-phenyl] | |
| 461 | CH₃ | 2,6-F₂ | [2-OCH₃-phenyl-CH₂O-4-OCF₃-phenyl] | |
| 462 | CH₃ | 2-Cl, 6-F | [2-OCH₃-phenyl-CH₂O-4-OCF₃-phenyl] | |
| 463 | CH₃ | 2,6-F₂ | [2-OCH₃-phenyl-CH₂O-2-Cl-4-CF₃-phenyl] | |
| 464 | CH₃ | 2-Cl, 6-F | [2-OCH₃-phenyl-CH₂O-2-Cl-4-CF₃-phenyl] | |

TABLE 2-continued
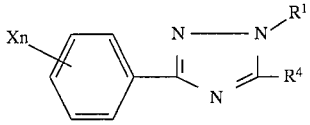
| Compound No. | R¹ | Xn | R⁴ | Melting point (°C.) of refractive index ($n_D^{20}$) |
|---|---|---|---|---|
| 465 | $CH_3$ | 2,6-$F_2$ | 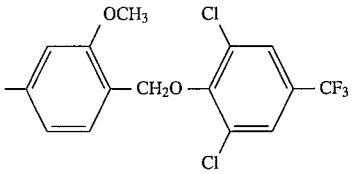 | |
| 466 | $CH_3$ | 2-Cl, 6-F | 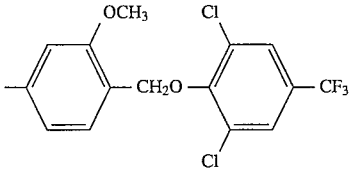 | |
| 467 | $CH_3$ | 2,6-$F_2$ | 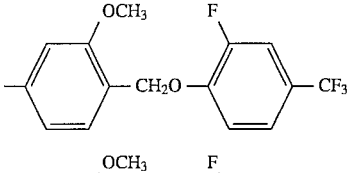 | |
| 468 | $CH_3$ | 2-Cl, 6-F | 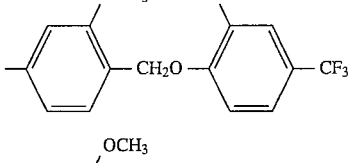 | |
| 469 | $CH_3$ | 2,6-$F_2$ | 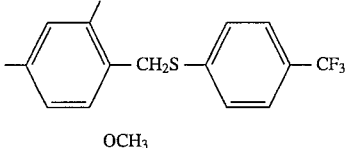 | |
| 470 | $CH_3$ | 2-Cl, 6-F | 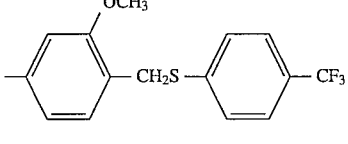 | |
| 471 | $CH_3$ | 2,6-$F_2$ | 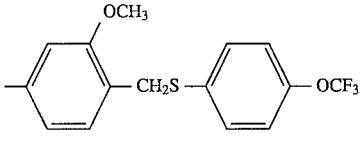 | |
| 472 | $CH_3$ | 2-Cl, 6-F | 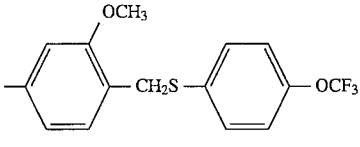 | |
| 473 | $CH_3$ | 2,6-$F_2$ | 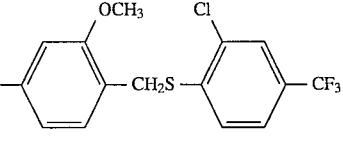 | |

TABLE 2-continued
| Compound No. | R¹ | Xn | R⁴ | Melting point (°C.) of refractive index ($n_D^{20}$) |
|---|---|---|---|---|
| 474 | CH₃ | 2-Cl, 6-F | 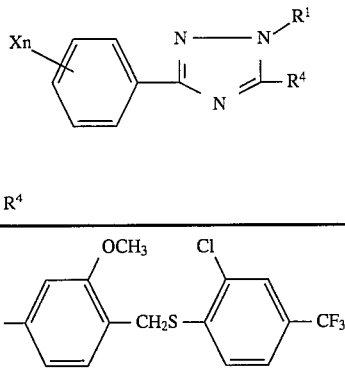 2-OCH₃-phenyl-CH₂S-(2-Cl,4-CF₃-phenyl) | |
| 475 | CH₃ | 2,6-F₂ | 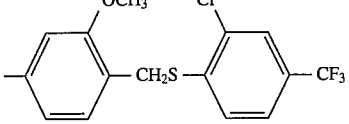 2-OCH₃-phenyl-CH₂S-(2,6-Cl₂,4-CF₃-phenyl) | |
| 476 | CH₃ | 2-Cl, 6-F | 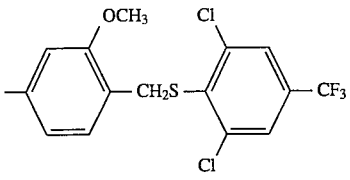 2-OCH₃-phenyl-CH₂S-(2,6-Cl₂,4-CF₃-phenyl) | |
| 477 | CH₃ | 2,6-F₂ | 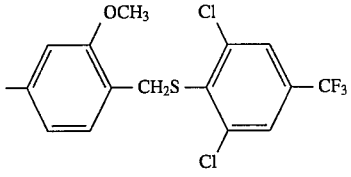 2-OCH₃-phenyl-CH₂S-(2-F,4-CF₃-phenyl) | |
| 478 | CH₃ | 2-Cl, 6-F | 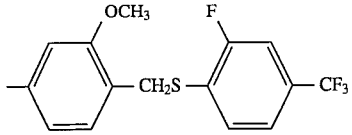 2-OCH₃-phenyl-CH₂S-(2-F,4-CF₃-phenyl) | |
| 479 | CH₃ | 2-Cl | 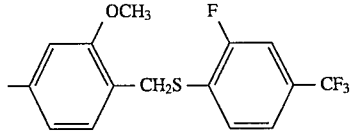 2-CH₃-phenyl-O-(2-Cl,4-CF₃-phenyl) | |
| 480 | CH₃ | 2-Cl, 6-F | 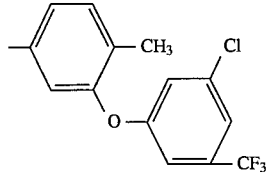 2-CH₃-phenyl-O-phenyl | 116.0–119.0 |
| 481 | CH₃ | 2,6-F₂ | 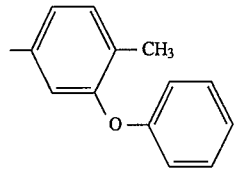 2-OCH₃-phenyl-O-(4-CF₃-phenyl) | |

TABLE 2-continued
| Compound No. | R¹ | Xn | R⁴ | Melting point (°C.) of refractive index ($n_D^{20}$) |
|---|---|---|---|---|
| 482 | $CH_3$ | 2-Cl, 6-F | 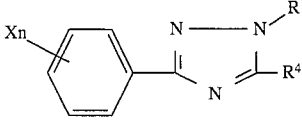 | |
| 483 | $CH_3$ | 2,6-$F_2$ | 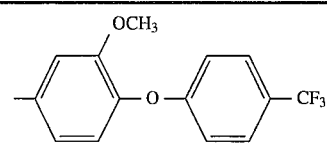 | |
| 484 | $CH_3$ | 2-Cl, 6-F | 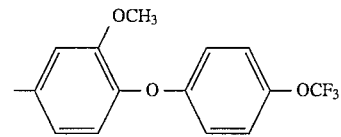 | |
| 485 | $CH_3$ | 2,6-$F_2$ | 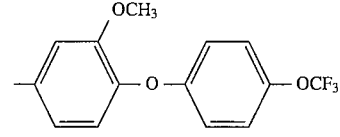 | |
| 486 | $CH_3$ | 2-Cl, 6-F | 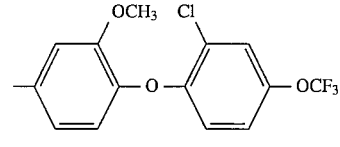 | |
| 487 | $CH_3$ | 2,6-$F_2$ | 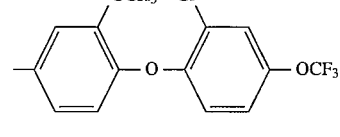 | |
| 488 | $CH_3$ | 2-Cl, 6-F | 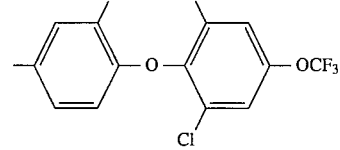 | |
| 489 | $CH_3$ | 2-Cl, 6-F | 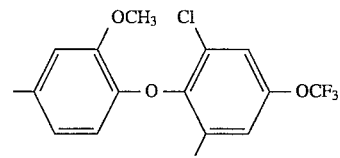 | 129.0–131.0 |
| 490 | $CH_3$ | 2,6-$F_2$ | 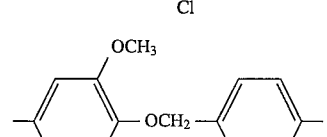 | |

TABLE 2-continued

| Compound No. | R¹ | Xn | R⁴ | Melting point (°C.) of refractive index ($n_D^{20}$) |
|---|---|---|---|---|
| 491 | $CH_3$ | 2-Cl, 6-F | 2-methoxy-phenyl-OCH₂-(6-chloropyridin-3-yl) | |
| 492 | $CH_3$ | 2,6-$F_2$ | 2-methoxy-phenyl-SCH₂-(6-chloropyridin-3-yl) | |
| 493 | $CH_3$ | 2-Cl, 6-F | 2-methoxy-phenyl-SCH₂-(6-chloropyridin-3-yl) | |
| 494 | $CH_3$ | 2-Cl | 2-methyl-phenyl-C≡C-(pyridin-2-yl) | |
| 495 | $CH_3$ | 2-Cl, 6-F | 2-methyl-phenyl-C≡C-(pyridin-2-yl) | |
| 496 | $CH_3$ | 2-Cl, 6-F | 2-methoxy-phenyl-CH₂O-(3-chloro-5-trifluoromethylpyridin-2-yl) | 97.0–102.0 |
| 497 | $CH_3$ | 2-Cl, 6-F | 2-methoxy-phenyl-CH₂O-(5-trifluoromethylpyridin-2-yl) | 74.0–79.0 |
| 498 | $CH_3$ | 2-Cl, 6-F | 2-methoxy-phenyl-CH₂O-(3,5-dichloropyridin-2-yl) | 129.0–134.0 |
| 499 | $CH_3$ | 2-Cl | 2-trifluoromethoxy-phenyl-CH₂O-(5-trifluoromethylpyridin-2-yl) | |

TABLE 2-continued
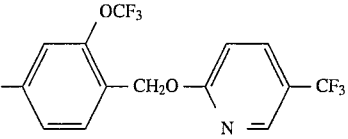
| Compound No. | R¹ | Xn | R⁴ | Melting point (°C.) of refractive index ($n_D^{20}$) |
|---|---|---|---|---|
| 500 | CH₃ | 2-Cl, 6-F | 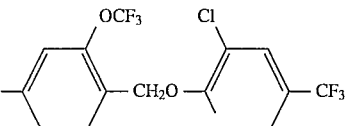 | |
| 501 | CH₃ | 2-Cl | 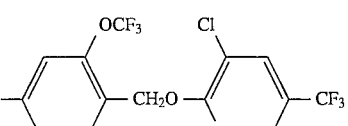 | |
| 502 | CH₃ | 2-Cl, 6-F | 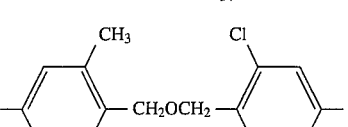 | |
| 503 | CH₃ | 2-Cl, 6-F | 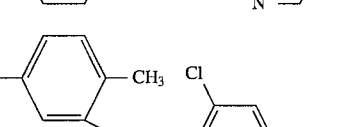 | |
| 504 | CH₃ | 2-Cl, 6-F | 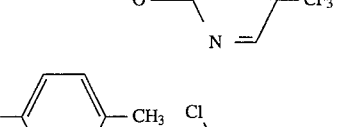 | |
| 505 | CH₃ | 2,6-F₂ | 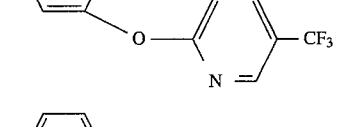 | |
| 506 | CH₃ | 2-Cl | 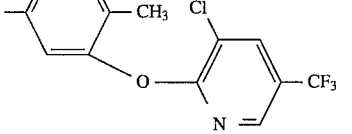 | |
| 507 | CH₃ | 2-Cl | | |

TABLE 2-continued

[Structure: Xn-phenyl-triazole with N-R¹ and R⁴ substituents]

| Compound No. | R¹ | Xn | R⁴ | Melting point (°C.) of refractive index ($n_D^{20}$) |
|---|---|---|---|---|
| 508 | CH₃ | 2-Cl, 6-F | 2-methyl-phenoxy linked to 3-CF₃, 5-Cl-pyridin-2-yl | 142.0–144.0 |
| 509 | CH₃ | 2-Cl | 2-methyl-phenoxy linked to 4-CF₃-pyridin-2-yl | not measurable |
| 510 | CH₃ | 2-Cl, 6-F | 2-methyl-phenoxy linked to 4-CF₃-pyridin-2-yl | not measurable |
| 511 | CH₃ | 2-Cl, 6-F | 2-methyl-phenoxy linked to 5-Cl-pyridin-2-yl | 1.6087 |
| 512 | CH₃ | 2-Cl | 2-methyl-phenoxy linked to 5-Cl-pyridin-2-yl | |
| 513 | CH₃ | 2,6-F₂ | 2-methyl-phenoxy linked to 5-Cl-pyridin-2-yl | 105.0–109.0 |
| 514 | CH₃ | 2-Cl, 6-F | 2-methyl-phenoxy linked to 4-CF₃, 6-CF₃-pyridin-2-yl | 155.0–157.0 |

TABLE 2-continued

[Structure: Xn-phenyl-triazole with N-R¹ and R⁴ substituents]

| Compound No. | R¹ | Xn | R⁴ | Melting point (°C.) of refractive index ($n_D^{20}$) |
|---|---|---|---|---|
| 515 | CH₃ | 2-Cl | [2-methoxy-phenyl-O-(5-trifluoromethylpyridin-2-yl)] | |
| 516 | CH₃ | 2-Cl, 6-F | [2-methoxy-phenyl-O-(5-trifluoromethylpyridin-2-yl)] | not measurable |
| 517 | CH₃ | 2,6-F₂ | [2-methoxy-phenyl-O-(5-trifluoromethylpyridin-2-yl)] | not measurable |
| 518 | CH₃ | 2,6-F₂ | [2-methoxy-phenyl-O-(3-chloro-5-trifluoromethylpyridin-2-yl)] | |
| 519 | CH₃ | 2-Cl, 6-F | [2-methoxy-phenyl-O-(3-chloro-5-trifluoromethylpyridin-2-yl)] | |
| 520 | CH₃ | 2,6-F₂ | [3-methoxy-phenyl-O-(5-trifluoromethylpyridin-2-yl)] | |
| 521 | CH₃ | 2-Cl, 6-F | [3-methoxy-phenyl-O-(5-trifluoromethylpyridin-2-yl)] | |

TABLE 2-continued

[Structure: Xn-phenyl-triazole with R¹ on N, R⁴ substituent, core structure as shown]

| Compound No. | R¹ | Xn | R⁴ | Melting point (°C.) of refractive index ($n_D^{20}$) |
|---|---|---|---|---|
| 522 | CH₃ | 2,6-F₂ | [3-Cl-5-CF₃-pyridin-2-yloxy-phenyl with OCH₃] | 140.0–143.0 |
| 523 | CH₃ | 2-Cl, 6-F | [3-Cl-5-CF₃-pyridin-2-yloxy-phenyl with OCH₃] | not measurable |
| 524 | CH₃ | 2-Cl, 6-F | [5-CF₃-pyridin-2-yloxy-phenyl with OCH₃] | not measurable |
| 525 | CH₃ | 2,6-F₂ | [3-Cl-5-CF₃-pyridin-2-yloxy-phenyl with OCH₃] | |
| 526 | CH₃ | 2-Cl, 6-F | [3-Cl-5-CF₃-pyridin-2-yloxy-phenyl with OCH₃] | not measurable |
| 527 | CH₃ | 2,6-F₂ | [3,5-bis-CF₃-pyridin-2-yloxy-phenyl with OCH₃] | |
| 528 | CH₃ | 2-Cl, 6-F | [3,5-bis-CF₃-pyridin-2-yloxy-phenyl with OCH₃] | |
| 529 | CH₃ | 2,6-F₂ | [3-Cl-5-CF₃-6-Cl-pyridin-2-yloxy-phenyl with OCH₃] | |

TABLE 2-continued

[structure: Xn-phenyl-triazole with N-R¹ and R⁴ substituents]

| Compound No. | R¹ | Xn | R⁴ | Melting point (°C.) of refractive index ($n_D^{20}$) |
|---|---|---|---|---|
| 530 | CH₃ | 2-Cl, 6-F | [OCH₃-phenyl-O-pyridyl(Cl,Cl,CF₃)] | |
| 531 | CH₃ | 2-Cl, 6-F | [CH₃-phenyl-OCH₂-pyridyl(Cl,CF₃)] | 102.0–104.0 |
| 532 | CH₃ | 2,6-F₂ | [OCH₃-phenyl-S-pyridyl(CF₃)] | |
| 533 | CH₃ | 2-Cl, 6-F | [OCH₃-phenyl-S-pyridyl(CF₃)] | |
| 534 | CH₃ | 2,6-F₂ | [OCH₃-phenyl-S-pyridyl(Cl,CF₃)] | |
| 535 | CH₃ | 2-Cl, 6-F | [OCH₃-phenyl-O-pyridyl(Cl,CF₃)] | |

The compounds according to the invention can be produced according to the following methods.

Production Method 1-1

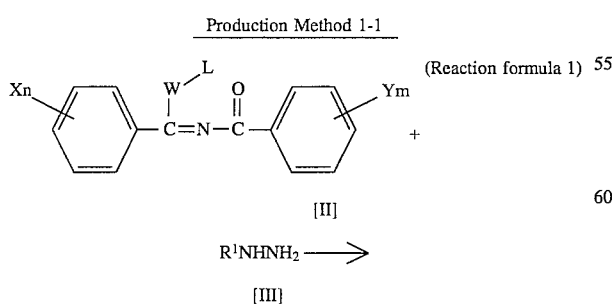

(Reaction formula 1)

[II]

R¹NHNH₂ ⟶

[III]

-continued
Production Method 1-1

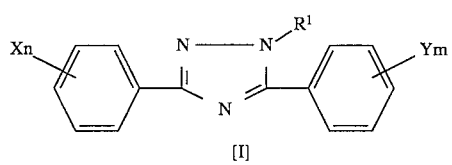

[I]

(wherein W is a sulfur atom or an oxygen atom, L is an alkyl group having a carbon number of 1–4, and R¹, X, n, Y and m are the same as mentioned above).

That is, the compound according to the invention represented by the general formula [I] can be obtained by reacting an N-acylimidate derivative or N-acylthioimidate derivative represented by a general formula [II] with a hydrazine derivative represented by a general formula [III] in an inert solvent.

As the solvent, any solvents not obstructing the reaction can be used, which include, for example, alcohols such as methanol, ethanol and so on; ethers such as diethyl ether, tetrahydrofuran, dioxane, 1,2-dimethoxyethane, diglyme and so on; aromatic hydrocarbons such as benzene, toluene, chlorobenzene, dichlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; nitriles such as acetonitrile and so on; aprotic polar solvents such as dimethylformamide, dimethylacetamide, dimethylsulfoxide and so on; water and a mixed solvent comprised of a combination of solvents selected from the above. Furthermore, the amount of the starting material used is usually 1.0–5.0 moles of the compound shown by the general formula [III] per 1 mole of the compound shown by the general formula [II].

The reaction temperature is within a range of from 0° C. to a boiling point of the solvent. The reaction time is different in accordance with the compound, but the object can usually be attained for 1 hour–72 hours. A concrete example of this reaction is described, for example, in Synthesis, page 483 (1983).

The starting compound shown by the general formula [II] can be produced by the following method.

Production Method 1-2

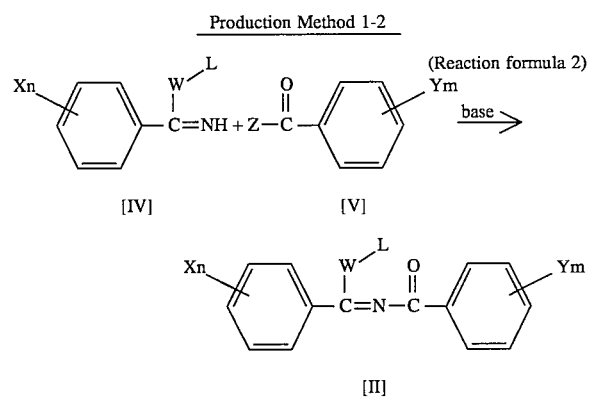

(wherein Z is a halogen atom, and L, W, X, n, Y and m are the same as mentioned above).

That is, the compound shown by the general formula [II] can be obtained by reacting a compound of a general formula [IV] with a compound of a general formula [V] in the presence of a base in an inert solvent. The compound of the general formula [IV] may be an acid addition salt such as a salt with boron tetrafluoride, hydrogen chloride, hydrogen bromide, hydrogen iodide or the like.

As the base, use may be made of inorganic bases such as sodium carbonate, potassium carbonate, sodium hydrogen carbonate, potassium hydrogen carbonate, sodium hydroxide, potassium hydroxide and the like; and organic bases such as diethylamine, triethylamine, pyridine, 4-(N,N-dimethylamino) pyridine and the like.

As the solvent, use may be made of ketones such as acetone, methyl ethyl ketone and so on; ethers such as diethyl ether, tetrahydrofuran, dioxane, 1,2-dimethoxyethane, diglyme and so on; aromatic hydrocarbons such as benzene, toluene, chlorobenzene, dichlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; nitriles such as acetonitrile and so on; aprotic polar solvents such as dimethylformamide, dimethylacetamide, dimethylsulfoxide and so on; and a mixed solvent comprised of a combination of solvents selected from the above.

The amount of the reactant used is usually 0.8–1.3 moles of the compound shown by the general formula [V] per 1 mole of the compound shown by the general formula [IV]. The amount of the base used is 1.0–2.0 moles per 1 mole of the compound shown by the general formula [IV]. The reaction temperature is within a range of from 0° C. to a boiling point of the solvent. The reaction time is different in accordance with the compound, but the object can usually be attained for 1 hour–24 hours.

Production Method 2

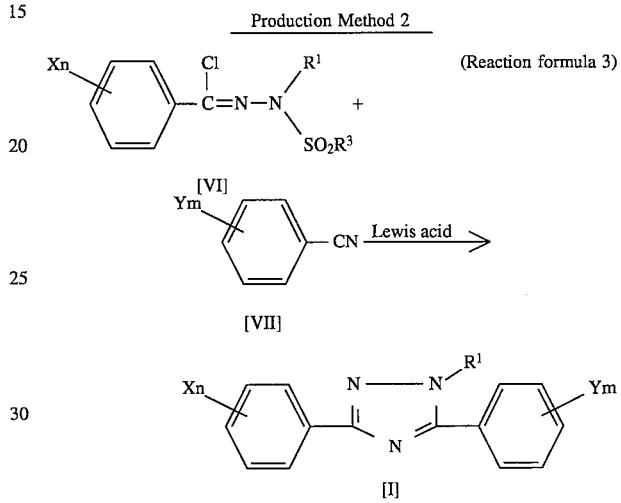

(wherein $R^1$, X, n, Y and m are the same as mentioned above, and $R^3$ is a phenyl group, which may be substituted with an alkyl group having a carbon number of 1–4, or an alkyl group having a carbon number of 1–4).

That is, the compound of the general formula [I] according to the invention can be obtained by reacting a benzohydrazonoyl chloride derivative represented by a general formula [VI] with a benzonitrile derivative represented by a general formula [VII] in the presence of a Lewis acid in an inert solvent.

As the solvent, any solvents not obstructing the reaction can be used, which include, for example, ethers such as diethyl ether, tetrahydrofuran, dioxane, 1,2-dimethoxyethane, diglyme, 1,2-dimethoxyethane and so on; aromatic hydrocarbons such as benzene, toluene, chlorobenzene, dichlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; aprotic polar solvents such as nitrobenzene, dimethylformamide, dimethylacetamide, dimethylsulfoxide and so on; a mixed solvent comprised of a combination of solvents selected from the above.

As the Lewis acid, use may be made of aluminum bromide, aluminum chloride, iron (III) chloride, boron trifluoride, titanium tetrachloride and so on. Furthermore, the amounts of the starting material and the like used are usually 1.0–2.0 moles of the compound shown by the general formula [VII] and 1.0–2.0 moles of the Lewis acid per 1 mole of the compound shown by the general formula [VI]. The reaction temperature is within a range of from 0° C. to a boiling point of the solvent. The reaction time is different in accordance with the compound, but the object can usually

Production Method 3-1

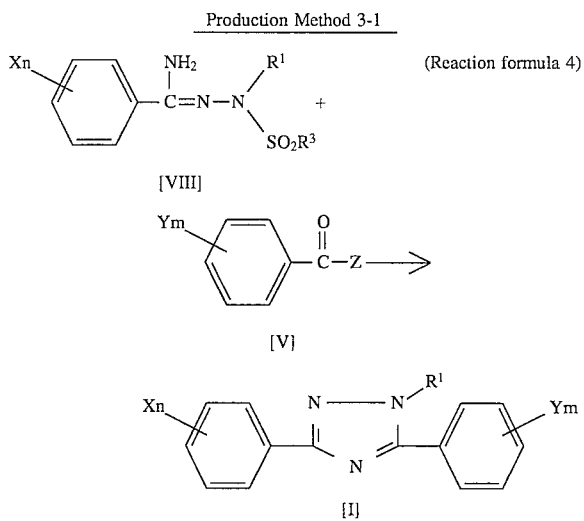

(Reaction formula 4)

(wherein $R^1$, $R^3$, X, n, Y, m and Z are the same as mentioned above).

That is, the compound of the general formula [I] according to the invention can be obtained by reacting a benzamidrazone derivative of a general formula [VIII] with a benzoylhalide derivative of a general formula [V] in the absence of a solvent or in an inert solvent.

As the solvent, any solvents not obstructing the reaction can be used, which include, for example, ethers such as diethyl ether, tetrahydrofuran, dioxane, 1,2-dimethoxyethane, diglyme and so on; aromatic hydrocarbons such as benzene, toluene, chlorobenzene, dichlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; aprotic polar solvents such as dimethylformamide, dimethylacetamide, dimethylsulfoxide, 1-methyl-2-pyrolidinone and so on; and a mixed solvent comprised of a combination of solvents selected from the above.

The amount of the starting material used is usually 1.0–2.0 moles of the compound shown by the general formula [V] per 1 mole of the compound shown by the general formula [VIII]. The reaction temperature is within a range of from 0° C. to a boiling point of the solvent. The reaction time is different in accordance with the compound, but the object can usually be attained for 30 minutes–5 hours. A concrete example of this reaction is described, for example, in Bulltein of the Chemical Society of Japan (Bull. Chem. Soc. Jpn), vol. 56, page 545 (1983).

Moreover, the compound of the general formula [VIII] as a starting material can be produced by the following method.

Production Method 3-2

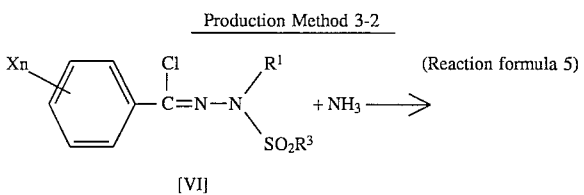

(Reaction formula 5)

Production Method 3-2 -continued

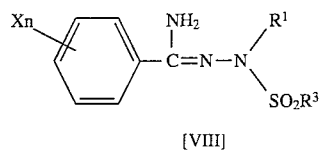

(wherein $R^1$, $R^3$, X and n are the same as mentioned above).

The compound of the general formula [VIII] can be obtained by reacting a compound of a general formula [VI] with an ammonia gas in an inert solvent.

As the solvent, any solvents not obstructing the reaction can be used, which include, for example, ethers such as diethyl ether, tetrahydrofuran, dioxane, 1,2-dimethoxyethane, diglyme and so on; aromatic hydrocarbons such as benzene, toluene, chlorobenzene, dichlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; aprotic polar solvents such as dimethylformamide, dimethylacetamide, dimethylsulfoxide and so on; and a mixed solvent comprised of a combination of solvents selected from the above.

The amount of the starting material used is usually 5.0–10.0 moles of ammonia per 1 mole of the compound shown by the general formula [VI]. The reaction temperature is within a range of from 0° C. to a boiling point of the solvent. The reaction time is different in accordance with the compound, but the object can usually be attained for 1 hour–24 hours. A concrete example of this reaction is described, for example, in Bulltein of the Chemical Society of Japan (Bull. Chem. Soc. Jpn), vol. 56, page 545 (1983).

Production Method 4-1

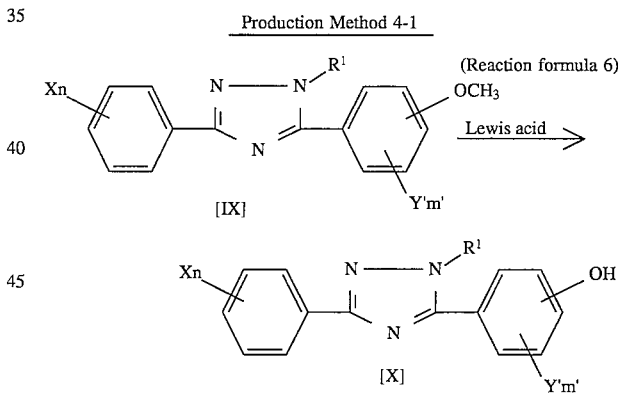

(Reaction formula 6)

(wherein X, $R^1$, Y', n and m' are the same as mentioned above).

A compound of a general formula [X] can be obtained by reacting a compound of a general formula [IX] in the presence of a Lewis acid in an inert solvent.

As the Lewis acid, use may be made of aluminum bromide, aluminum chloride, iron (III) chloride, boron trifluoride, titanium tetrachloride and so on.

As the solvent, any solvents not obstructing the reaction can be used, which include, for example, ethers such as diethyl ether, tetrahydrofuran, dioxane, 1,2-dimethoxyethane, diglyme and so on; aromatic hydrocarbons such as benzene, toluene, chlorobenzene, dichlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; aprotic polar solvents such as nitrobenzene, dimethylformamide, dimethylacetamide, dimethylsulfoxide and so on; and a mixed solvent comprised of a combination of solvents selected from the above.

The amount of the reactant used is usually 1.0–5.0 moles of the Lewis acid per 1 mole of the compound shown by the general formula [IX]. The reaction temperature is within a range of from −20° C. to a boiling point of the solvent. The reaction time is different in accordance with the compound, but the object can usually be attained for 1 hour–24 hours.

Production Method 4-2

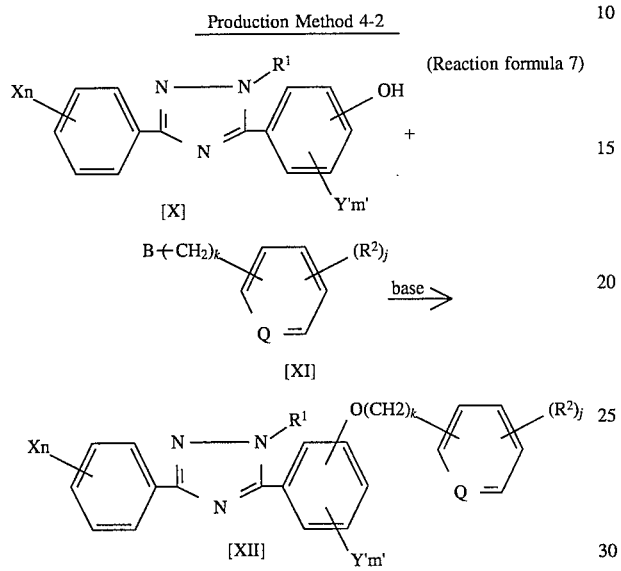

[wherein B is a halogen atom, $R^4\text{-SO}_2$-group or $R^4\text{-SO}_3$- group ($R^4$ is an alkyl group having a carbon number of 1–4 or a phenyl group which may be substituted), k is 0 or 1, and X, Y', $R^1$, $R^2$, Q, m' and n are the same as mentioned above).

The compound of a general formula [XII] according to the invention can be obtained by reacting a compound of a general formula [X] with a compound of a general formula [XI] in the presence of a base in an inert solvent.

As the base, use may be made of inorganic bases such as sodium carbonate, potassium carbonate, sodium hydrogen carbonate, potassium hydrogen carbonate, sodium hydroxide, potassium hydroxide and the like; metal hydrides such as sodium hydride, poptassium hydride and the like; and organic bases such as triethylamine, pyridine and the like.

As the solvent, use may be made of ketones such as acetone, methyl ethyl ketone and the like; ethers such as diethyl ether, tetrahydrofuran, dioxane, 1,2-dimethoxyethane, diglyme and so on; aromatic hydrocarbons such as benzene, toluene, chlorobenzene, dichlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; nitriles such as acetonitrile and the like; aprotic polar solvents such as dimethylformamide, dimethylacetamide, dimethylsulfoxide and so on; and a mixed solvent comprised of a combination of solvents selected from the above.

The amount of the reactant used is usually 1.0–2.0 moles of the compound shown by the general formula [XI] per 1 mole of the compound shown by the general formula [X]. The amount of the base used is 1.0–2.0 moles per 1 mole of the compound shown by the general formula [X]. The reaction temperature is within a range of from −20° C. to a boiling point of the solvent. The reaction time is different in accordance with the compound, but the object can usually be attained for 1–24 hours.

Production Method 5-1

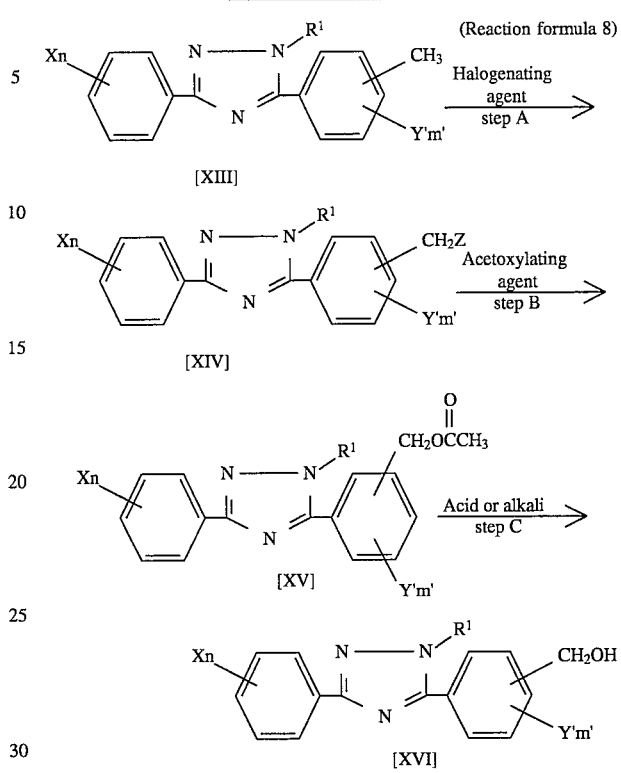

(wherein X, $R^1$, Z, Y', n and m' are the same as mentioned above).

A compound of a general formula [XIV] can be obtained from a triazole derivative of a general formula [XIII] with a halogenating agent. This compound can be reacted with an acetoxylating agent to obtain a compound of a general formula [XV]. Then, the compound of the general formula [XV] can be reacted with an acid or alkali to obtain a compound of a general formula [XVI].

As the halogenating agent used in the step A, use may be made of, for example, N-chlorosuccinimide, N-bromosuccinimide, N-bromophthalimide and so on.

As the solvent used, mention may be made of aliphatic halogenated hydrocarbons such as dichloromethane, dichloroethane, chloroform, carbon tetrachloride and so on. Furthermore, it is required to use a catalytic amount of benzoyl peroxide, azobisisobutyronitrile or the like as a radical initiator in this reaction.

The amount of the halogenating agent used is usually 0.8–1.5 moles per 1 mole of the compound shown by the general formula [XIII]. The reaction temperature is within a range of from 0° C. to a boiling point of the solvent. The reaction time is different in accordance with the compound, but the object can usually be attained for 30 minutes–12 hours.

As the acetoxylating agent used in the step B, use may be made of lithium acetate, sodium acetate, potassium acetate, calcium acetate and so on.

As the solvent, use may be made of ketones such as acetone, methyl ethyl ketone and so on; ethers such as diethyl ether, tetrahydrofuran, dioxane, 1,2-dimethoxyethane, diglyme and so on; aromatic hydrocarbons such as benzene, toluene, chlorobenzene, dichlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; nitriles such as acetonitrile and so on; aprotic polar solvents such as dimethylformamide, dimethylacetamide, dimethylsulfoxide and so on; and a mixed solvent comprised of a combination of solvents selected from the above.

The amount of the acetoxylating agent used is usually 1.0–4.0 moles per 1 mole of the compound shown by the general formula [XIV]. The reaction temperature is within a range of from 0° C. to a boiling point of the solvent. The reaction time is different in accordance with the compound, but the object can usually be attained for 1–24 hours.

As the acid used in the step C, use may be made of mineral acids such as hydrochloric acid, sulfuric acid and so on; and Lewis acids such as aluminum bromide, aluminum chloride and so on. In this case, as the solvent, use may be made of carboxylic acids such as acetic acid, formic acid and so on; ketones such as acetone, methyl ethyl ketone and so on; ethers such as diethyl ether, tetrahydrofuran, dioxane, dimethoxyethane and so on; aromatic hydrocarbons such as benzene, toluene and so on; aliphatic hydrocarbons such as pentane, hexane, petroleum ether and so on; aliphatic halogenated hydrocarbons such as dichloromethane, dichloroethane, carbon tetrachloride and so on; water and a mixed solvent comprised of a combination of solvents selected from the above.

The amount of the acid used is usually a catalytic amount—4.0 moles per 1 mole of the compound shown by the general formula [XV]. The reaction temperature is within a range of from 0° C. to a boiling point of the solvent. The reaction time is different in accordance with the compound, but the object can usually be attained for 30 minutes–24 hours.

As the alkali used in the step C, use may be made of aqueous solutions of sodium hydroxide, potassium hydroxide, potassium carbonate, sodium carbonate and so on. In this case, as the solvent, use may be made of alcohols such as methanol, ethanol, ethylene glycol and so on; ketones such as acetone, methyl ethyl ketone and so on; ethers such as tetrahydrofuran, dioxane, 1,2-dimethoxyethane and so on; water and a mixed solvent comprised of a combination of solvents selected from the above.

The amount of the alkali used is usually 0.5–4.0 moles per 1 mole of the compound shown by the general formula [XV]. The reaction temperature is within a range of from 0° C. to a boiling point of the solvent. The reaction time is different in accordance with the compound, but the object can usually be attained for 30 minutes–24 hours.

Production Method 5-2

(Reaction formula 9)

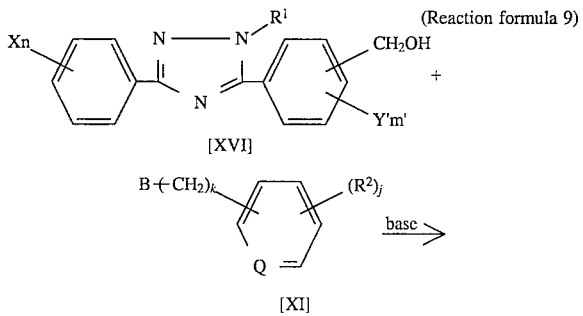

-continued
Production Method 5-2

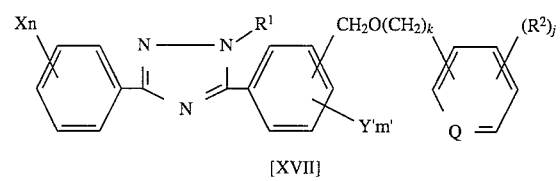

(wherein X, Y', B, Q, $R^1$, $R^2$, j, k, m' and n are the same as mentioned above).

The compound shown by the general formula [XVII] according to the invention can be obtained by reacting a compound of a general formula [XVI] with a compound of a general formula [XI] in the presence of a base in an inert solvent.

As the base, use may be made of inorganic bases such as sodium carbonate, potassium carbonate, sodium hydrogen carbonate, potassium hydrogen carbonate, sodium hydroxide, potassium hydroxide and the like; metal hydrides such as sodium hydride, potassium hydride and the like; and organic bases such as triethylamine, pyridine and the like.

As the solvent, use may be made of ketones such as acetone, methyl ethyl ketone and so on; ethers such as diethyl ether, tetrahydrofuran, dioxane, 1,2-dimethoxyethane, diglyme and so on; aromatic hydrocarbons such as benzene, toluene, chlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; nitriles such as acetonitrile and so on; aprotic polar solvents such as dimethylformamide, dimethylacetamide, dimethylsulfoxide and so on; and a mixed solvent comprised of a combination of solvents selected from the above.

The amount of the reactant used is usually 1.0–2.0 moles of the compound shown by the general formula [XI] per 1 mole of the compound shown by the general formula [XVI]. The amount of the base used is 1.0–2.0 moles per 1 mole of the compound shown by the general formula [XVI]. The reaction temperature is within a range of from −20° C. to a boiling point of the solvent. The reaction time is different in accordance with the compound, but the object can usually be attained for 1–24 hours.

Production Method 5-3

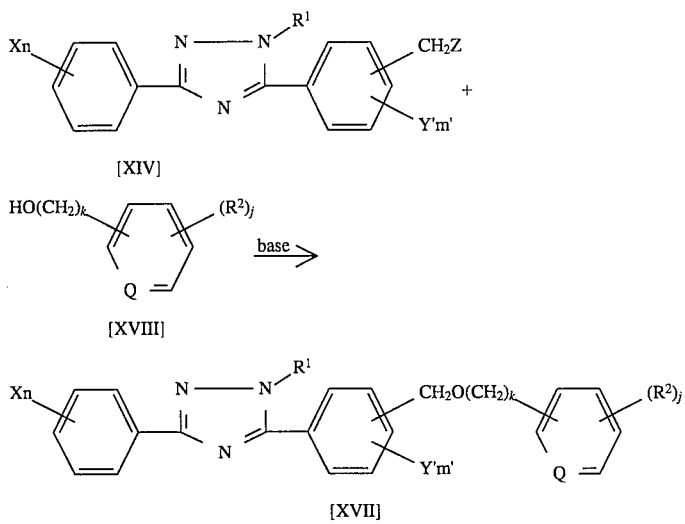

(wherein X, Y', Q, R¹, R², Z j, k m' and n are the same as mentioned above).

The compound shown by the general formula [XVII] according to the invention can be obtained by reacting a compound of the general formula [XIV] with a compound of the general formula [XVIII] in the presence of a base in an inert solvent.

As the base, use may be made of inorganic bases such as sodium carbonate, potassium carbonate, sodium hydrogen carbonate, potassium hydrogen carbonate, sodium hydroxide, potassium hydroxide and the like; metal hydrides such as sodium hydride, potassium hydride and the like; and organic bases such as triethylamine, pyridine and the like.

As the solvent, use may be made of ketones such as acetone, methyl ethyl ketone and so on; ethers such as diethyl ether, tetrahydrofuran, dioxane, 1,2-dimethoxyethane, diglyme and so on; aromatic hydrocarbons such as benzene, toluene, chlorobenzene and so on; aliphatic hydrocarbons such as pentane, hexane, petroleum ether and so on; aliphatic halogenated hydrocarbons such as dichloromethane, dichloroethane, chloroform, carbon tetrachloride and so on; nitriles such as acetonitrile and so on; aprotic polar solvents such as dimethylformamide, dimethylacetamide, dimethylsulfoxide and so on; and a mixed solvent comprised of a combination of solvents selected from the above.

The amount of the reactant used is usually 1.0–2.0 moles of the compound shown by the general formula [XVIII] per 1 mole of the compound shown by the general formula [XIV]. The amount of the base used is 1.0–2.0 moles per 1 mole of the compound shown by the general formula [XIV]. The reaction temperature is within a range of from −20° C. to a boiling point of the solvent. The reaction time is different in accordance with the compound, but the object can usually be attained for 1–24 hours.

BEST MODE FOR CARRYING OUT THE INVENTION

The preparation method of the compounds according to the invention, formulation method and applications will concretely be described with reference to the following examples.

(Reaction formula 10)

Example 1

Preparation of 3-(2-chlorophenyl)-5-(2-chloro-3-nitrophenyl) 1-methyl-1H-1,2,4-triazole (Compound No. 1)

A mixture of N-methyl-N-(benzenesulfonyl)-2-chlorobenzohydrazonoyl chloride (1.72 g), 2-chloro-3-nitrobenzonitrile (1.00 g), anhydrous aluminum chloride (0.70 g) and o-dichlorobenzene (20 ml) is stirred at an oil bath temperature of 140° C. for 30 minutes. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexane-ethyl acetate as eluent to give 1.12 g of desired compound (melting point: 124.0°–125.0° C.).

NMR data (60 MHz, CDCl₃ solvent, δ value: ppm)
3.83 (3H, s)
7.16–8.10 (7H, m)

Example 2

Preparation of 3-(2-chloro-6-fluorophenyl)-5-(2-chloro-3-nitrophenyl) 1-methyl-1H-1,2,4-triazole (Compound No. 2)

A mixture of N-methyl-N-(p-toluenesulfonyl)-2-chloro-6-fluorobenzohydrazonoyl chloride (1.90 g), 2-chloro-3-nitrobenzonitrile (1.19 g), anhydrous aluminum chloride (0.70 g) and o-dichlorobenzene (20 ml) is stirred at an oil bath temperature of 140° C. for 30 minutes. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexaneethyl acetate as eluent to give 1.19 g of desired compound (melting point: 112.0°–114.0° C.).

NMR data (60 MHz, CDCl$_3$ solvent, δ value: ppm)
3.90 (3H, s)
6.90–8.10 (6H, m)

Example 3

Preparation of
3-(2-chloro-6-fluorophenyl)-5-(2-chloro-4-nitrophenyl) 1-methyl-1H-1,2,4-triazole (Compound No. 4)

A mixture of N-methyl-N-(p-toluenesulfonyl)-2-chloro-6-fluorobenzohydrazonoyl chloride (1.90 g), 2-chloro-4-nitrobenzonitrile (1.80 g), anhydrous iron (III) chloride (1.60 g) and o-dichlorobenzene (5 ml) is stirred at an oil bath temperature of 140° C. for 1 hour. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexane-ethyl acetate as eluent to give 2.20 g of desired compound (melting point: 144.0°–148.0° C.).

NMR data (60 MHz, CDCl$_3$ solvent, δ value: ppm)
3.88 (3H, s)
6.90–8.46 (6H, m)

Example 4

Preparation of
5-(2-chloro-4-ethylphenyl)-3-(2-chlorophenyl) 1-methyl-1H-1,2,4-triazole (Compound No. 15)

Ethyl 2-chlorobenzimidate (2.75 g) and triethylamine (1.60 g) are dissolved in toluene (30 ml) and 2-chloro-4-ethylbenzoyl chloride (2.64 g) is added dropwise thereto within a range of 5° C.–15° C. with stirring, which is stirred at room temperature for 1 hour and further heated under reflux for 3 hours. After cooling to room temperature, the reaction mixture is added with toluene (200 ml) and washed with dilute hydrochloric acid and saline, and the organic layer is dried over anhydrous magnesium sulfate. The organic layer is added with monomethyl hydrazine (1.00 g) and stirred at room temperature for 16 hours. On completion of the reaction, the reaction mixture is washed with dilute hydrochloric acid and saline, dried over anhydrous magnesium sulfate and concentrated under reduced pressure. The concentrate is purified by silica gel column chromatography using mixed solution of hexane-ethyl acetate as eluent to give 2.10 g of desired compound (melting point: 75.5°–77.5° C.).

NMR data (60 MHz, CDCl$_3$ solvent, δ value: ppm)
1.27 (3H, t)
2.70 (2H, q)
3.83 (3H, s)
7.10–7.60 (6H, m)
7.90–8.10 (1H, m)

Example 5

Preparation of
5-(2-chloro-4-ethylphenyl)-3-(2-chloro-6-fluorophenyl) 1-methyl-1H-1,2,4-triazole (Compound No. 16)

Ethyl 2-chloro-6-fluorobenzimidate (3.02 g) and triethylamine (1.60 g) are dissolved in toluene (30 ml) and 2-chloro-4-ethylbenzoyl chloride (2.64 g) is added dropwise thereto within a range of 5° C.–15° C. with stirring, which is stirred at room temperature for 1 hour and further heated under reflux for 3 hours. After cooling to room temperature, the reaction solution is added with toluene (200 ml) and washed with dilute hydrochloric acid and saline, and the organic layer is dried over anhydrous magnesium sulfate. The organic layer is added with monomethyl hydrazine (2.00 g) and heated under reflux for 2 hours. On completion of the reaction, the reaction mixture is washed with dilute hydrochloric acid and saline, dried over anhydrous magnesium sulfate and concentrated under reduced pressure. The concentrate is purified by silica gel column chromatography using mixed solution of hexaneethyl acetate as eluent to give 2.63 g of desired compound (refractive index: 1.5930).

NMR data (60 MHz, CDCl$_3$ solvent, δ value: ppm)
1.26 (3H, t)
2.69 (2H, q)
3.83 (3H, s)
6.90–7.50 (6H, m)

Example 6

Preparation of
3-(2-chlorophenyl)-5-(2-chloro-4-propylphenyl) 1-methyl-1H-1,2,4-triazole (Compound No. 18)

Ethyl 2-chlorobenzimidate (2.75 g) and triethylamine (1.80 g) are dissolved in toluene (30 ml) and 2-chloro-4-propylbenzoyl chloride (3.30 g) is added dropwise thereto within a range of 5° C.–15° C. with stirring, which is stirred at room temperature for 1 hour and further heated under reflux for 1 hour. After cooling to room temperature, the reaction solution is added with toluene (200 ml) and washed with dilute hydrochloric acid and saline, and the organic layer is dried over anhydrous magnesium sulfate. The organic layer is added with monomethyl hydrazine (0.80 g) and stirred at room temperature for 18 hours. On completion of the reaction, the reaction mixture is washed with dilute hydrochloric acid and saline, dried over anhydrous magnesium sulfate and concentrated under reduced pressure. The concentrate is purified by silica gel column chromatography using mixed solution of hexane-ethyl acetate as eluent to give 2.78 g of desired compound (melting point: 70.0°–72.0° C.).

NMR data (60 MHz, CDCl$_3$ solvent, δ value: ppm)
0.95 (3H, t)
1.66 (2H, m)
2.63 (2H, t)
3.83 (3H, s)
6.90–7.10 (1H, m)
7.10–7.50 (6H, m)

Example 7

Preparation of 3-(2-chloro-6-fluorophenyl)-5-(2-chloro-4-propylphenyl) 1-methyl-1H-1,2,4-triazole (Compound No. 19)

Ethyl 2-chloro-6-fluorobenzimidate (3.02 g) and triethylamine (1.80 g) are dissolved in toluene (30 ml) and 2-chloro-4-propylbenzoyl chloride (3.30 g) is added dropwise thereto within a range of 5° C.–15° C. with stirring, which is stirred at room temperature for 1 hour and further heated under reflux for 1 hour. After cooling to room temperature, the reaction solution is added with toluene (200 ml) and washed with dilute hydrochloric acid and saline, and the organic layer is dried over anhydrous magnesium sulfate. The organic layer is added with monomethyl hydrazine (1.80 g) and heated under reflux for 4 hours. On completion of the reaction, the reaction mixture is washed with dilute hydrochloric acid and saline, dried over anhydrous magnesium sulfate and concentrated under reduced pressure. The concentrate is purified by silica gel column chromatography using mixed solution of hexaneethyl acetate as eluent to give 0.41 g of desired compound (refractive index: 1.5868).

NMR data (60 MHz, CDCl$_3$ solvent, δ value: ppm)

0.95 (3H, t)

1.65 (2H, m)

2.62 (2H, t)

3.83 (3H, s)

6.80–7.50 (6H, m)

Example 8

Preparation of 5-(4-butyl-2-chlorophenyl)-3-(2-chloro-6-fluorophenyl) 1-methyl-1H-1,2,4-triazole (Compound No. 29)

N-methyl-N-(phenylsulfonyl)-2-chloro-6-fluorobenzohydrazonoyl chloride (1.10 g), 4-butyl-2-chlorobenzonitrile (0.60 g) and anhydrous aluminum chloride (0.50 g) are added to o-dichlorobenzene (10 ml) and stirred at 120° C. for 1 hour. On completion of the reaction, chloroform (100 ml) is added and washed with dilute hydrochloric acid. After washing with water, the organic layer is dried over anhydrous magnesium sulfate and concentrated under reduced pressure. The concentrate is purified by silica gel column chromatography using mixed solution of hexane-ethyl acetate as eluent to give 0.70 g of compound (refractive index: 1.5667).

NMR data (60 MHz, CDCl$_3$ solvent, δ value: ppm)

0.75–1.12 (3H, m)

1.15–2.00 (4H, m)

2.65 (2H, t)

3.85 (3H, s)

6.83–7.60 (6H, m)

Example 9

Preparation of 5-(4-t-butyl-2-ethoxyphenyl)-3-(2-chloro-6-fluorophenyl) 1-methyl-1H-1,2,4-triazole (Compound No. 35)

A mixture of N-methyl-N-(benzenesulfonyl)-2-chloro-6-fluorobenzohydrazonoyl chloride (1.60 g), 4-t-butyl-2-ethoxybenzonitrile (1.00 g), anhydrous aluminum chloride (0.60 g) and o-dichlorobenzene (5 ml) is stirred at an oil bath temperature of 140° C. for 30 minutes. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexane-ethyl acetate as eluent to give 0.20 g of desired compound (melting point: 108.0°–111.0° C.).

NMR data (60 MHz, CDCl$_3$ solvent, δ value: ppm)

1.15 (9H, s)

1.36 (3H, t)

3.87 (3H, s)

4.10 (2H, q)

6.83–7.58 (6H, m)

Example 10

Preparation of 3-(2-chlorophenyl)-5-(2-fluoro-5-hexylphenyl) 1-methyl-1H-1,2,4-triazole (Compound No. 42)

A mixture of N-methyl-N-(benzenesulfonyl)-2-chlorobenzohydrazonoyl chloride (2.06 g), 2-fluoro-5-hexylbenzonitrile (1.23 g), anhydrous aluminum chloride (0.88 g) and o-dichlorobenzene (5 ml) is stirred at an oil bath temperature of 140° C. for 30 minutes. After cooling, the reaction mixture is dissolved in chloroform (200 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexane-ethyl acetate as eluent to give 1.60 g of desired compound (refractive index: 1.5779).

NMR data (60 MHz, CDCl$_3$ solvent, δ value: ppm)

0.87 (3H, t)

1.00–1.90 (8H, m)

2.62 (2H, t)

3.87 (3H, d)

6.90–8.00 (7H, m)

Example 11

Preparation of 3-(2-chloro-6-fluorophenyl)-5-(2-fluoro-5-hexylphenyl) 1-methyl-1H-1,2,4-triazole (Compound No. 43)

A mixture of N-methyl-N-(benzenesulfonyl)-2-chloro-6-fluorobenzohydrazonoyl chloride (2.17 g), 2-fluoro-5-hexylbenzonitrile (1.23 g), anhydrous aluminum chloride (0.88 g) and o-dichlorobenzene (10 ml) is stirred at an oil bath temperature of 140° C. for 30 minutes. After cooling, the reaction mixture is dissolved in chloroform (200 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexane-ethyl acetate as eluent to give 1.11 g of desired compound (refractive index: 1.5608).

NMR data (60 MHz, CDCl$_3$ solvent, δ value: ppm)

0.87 (3H, t)

1.00–1.80 (8H, m)

2.61 (2H, t)

3.89 (3H, d)

6.80–7.40 (6H, m)

Example 12

Preparation of 3-(2,6-difluorophenyl)-5-(2-fluoro-5-undecylphenyl) 1-methyl-1H-1,2,4-triazole (Compound No. 46)

A mixture of N-methyl-N-(benzenesulfonyl)-2,6-difluorobenzohydrazonoyl chloride (1.28 g), 2-fluoro-5-undecylbenzonitrile (1.09 g), anhydrous aluminum chloride (0.55 g) and o-dichlorobenzene (10 ml) is stirred at an oil bath temperature of 140° C. for 30 minutes. After cooling, the reaction mixture is dissolved in chloroform (200 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexane-ethyl acetate as eluent to give 1.08 g of desired compound (melting point: 70.0°–73.0° C.).

NMR data (60 MHz, CDCl$_3$ solvent, δ value: ppm)

0.88 ( 3H, t )

1.10–1.80 ( 18H, m)

2.63 (2H, t)

3.93 (3H, d)

6.90–7.60 (6H, m)

Example 13

Preparation of 3-(2-chlorophenyl)-5-(2-fluoro-5-undecylphenyl) 1-methyl-1H-1,2,4-triazole (Compound No. 47)

A mixture of N-methyl-N-(benzenesulfonyl)-2-chlorobenzohydrazonoyl chloride (1.27 g), 2-fluoro-5-undecylbenzonitrile (1.09 g), anhydrous aluminum chloride (0.55 g) and o-dichlorobenzene (5 ml) is stirred at an oil bath temperature of 140° C. for 30 minutes. After cooling, the reaction mixture is dissolved in chloroform (200 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexaneethyl acetate as eluent to give 0.85 g of desired compound (melting point: 35.0°–37.0° C.).

NMR data (60 MHz, CDCl$_3$ solvent, δ value: ppm)

0.88 (3H, t)

1.10–1.70 (18H, m)

2.66 (2H, t)

3.93 (3H, d)

6.90–7.60 (6H, m)

7.90–8.00 (1H, m)

Example 14

Preparation of 3-(2-chloro-6-fluorophenyl)-5-(2-fluoro-5-undecylphenyl) 1-methyl-1H-1,2,4-triazol (Compound No. 48)

A mixture of N-methyl-N-(benzenesulfonyl)-2-chloro-6-fluorobenzohydrazonoyl chloride (1.34 g), 2-fluoro-5-undecylbenzonitrile (1.09 g), anhydrous aluminum chloride (0.55 g) and o-dichlorobenzene (10 ml) is stirred at an oil bath temperature of 140° C. for 30 minutes. After cooling, the reaction mixture is dissolved in chloroform (200 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexaneethyl acetate as eluent to give 1.04 g of desired compound (refractive index: 1.5419).

NMR data (60 MHz, CDCl$_3$ solvent, δ value: ppm)

0.87 (3H, t)

1.10–1.80 (18H, m)

2.63 (2H, t)

3.94 (3H, d)

6.90–7.60 (6H, m)

Example 15

Preparation of 3-(2-chloro-6-fluorophenyl)-5-(2-chloro-4-dodecylphenyl) 1-methyl-1H-1,2,4-triazol (Compound No. 51)

A mixture of N-methyl-N-(benzenesulfonyl)-2-chloro-6-fluorobenzohydrazonoyl chloride (1.50 g), 2-chloro-4-dodecylbenzonitrile (1.20 g), anhydrous aluminum chloride (0.60 g) and o-dichlorobenzene (5 ml) is stirred at an oil bath temperature of 140° C. for 30 minutes. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexaneethyl acetate as eluent to give 0.80 g of desired compound (refractive index: 1.5490).

NMR data (60 MHz, CDCl$_3$ solvent, δ value: ppm)

0.50–2.03 (23H, m)

2.65 (2H, t)

3.83 (3H, s)

6.82–7.52 (6H, m)

Example 16

Preparation of 5-(4-butoxy-2-chlorophenyl)-3-(2-chlorophenyl) 1-methyl-1H-1,2,4-triazole (Compound No. 64)

Ethyl 2-chlorobenzimidate (2.40 g) and triethylamine (1.20 g) are dissolved in toluene (100 ml) and 4-butoxy-2-chlorobenzoyl chloride (2.60 g) is added dropwise thereto below 10° C. with stirring. It is stirred at room temperature for 2 hours and further heated under reflux for 2 hours. On completion of the reaction, the reaction solution is washed with saline, further washed with water and the organic layer is dried over anhydrous magnesium sulfate. The toluene layer is added with monomethyl hydrazine (1.50 g) and reacted at room temperature for 24 hours. On completion of the reaction, it is washed with dilute hydrochloric acid, further washed with water and the organic layer is dried over anhydrous magnesium sulfate and concentrated under reduced pressure. The concentrate is purified by silica gel column chromatography using mixed solvent of hexaneethyl acetate as eluent to give 1.00 g of desired compound (melting point: 60.0°–62.0° C.).

NMR data (60 MHz, CDCl$_3$ solvent, δ value: ppm)

0.80–1.16 (3H, m)

1.20–2.10 (4H, m)

3.84 (3H, s)

4.02 (2H, t)

6.76–7.95 (6H, m)

7.83–8.12 (1H, m)

Example 17

Preparation of 3-(2-chloro-6-fluorophenyl)-5-(4-chloro-3-pentyloxyphenyl) 1-methyl-1H-1,2,4triazole (Compound No. 68)

A mixture of N-methyl-N-(p-toluenesulfonyl)-2-chloro-6-fluorobenzohydrazonoyl chloride (1.10 g), 4-chloro-3- pentyloxybenzonitrile (0.70 g), anhydrous iron (III) chloride (0.60 g) and o-dichlorobenzene (5 ml) is stirred at an oil bath temperature of 140° C. for 30 minutes. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexaneethyl acetate as eluent to give 0.50 g of desired compound.

NMR data (60 MHz, $CDCl_3$ solvent, $\delta$ value: ppm)

0.72–2.16 (9H, m)

4.06 (3H, s)

4.10 (2H, t)

6.85–7.60 (6H, m)

Example 18

Preparation of 5-(4-chloro-3-octyloxyphenyl)-3-(2-chlorophenyl) 1-methyl-1H-1,2,4-triazole (Compound No. 77)

A mixture of N-methyl-N-(benzenesulfonyl)-2-chlorobenzohydrazonoyl chloride (1.50 g), 4-chloro-3-octyloxybenzonitrile (1.30 g), anhydrous iron (III) chloride (0.80 g) and o-dichlorobenzene (5 ml) is stirred at an oil bath temperature of 140° C. for 30 minutes. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexaneethyl acetate as eluent to give 0.80 g of desired compound.

NMR data (60 MHz, $CDCl_3$ solvent, $\delta$ value: ppm)

0.65–2.13 (15H, m)

4.07 (3H, s)

4.13 (2H, t)

6.92–7.66 (7H, m)

Example 19

Preparation of 3-(2-chlorophenyl)-5-(2-chloro-4-methoxyethoxyphenyl) 1-methyl-1H-1,2,4-triazole (Compound No. 87)

Ethyl 2-chlorobenzimidate (4.00 g) and triethylamine (2.60 g) are dissolved in toluene (20 ml) and 2-chloro-4-methoxyethoxybenzoyl chloride (4.20 g) is added dropwise thereto within a range of 5° C.–10° C. with stirring. It is stirred at room temperature for 1 hour and further heated under reflux for 30 minutes. After cooling to room temperature, the reaction solution is added with toluene (20 ml) and washed with dilute sulfuric acid and saline and the organic layer is dried over anhydrous magnesium sulfate. The organic layer is added with monomethyl hydrazine (2.00 g) and stirred at room temperature for 4 hours. On completion of the reaction, the reaction mixture is washed with dilute sulfuric acid and saline, dried over anhydrous magnesium sulfate and concentrated under reduced pressure. The concentrate is purified by silica gel column chromatography using mixed solvent of hexane-ethyl acetate as eluent to give 0.70 g of desired compound (refractive index: 1.5946).

NMR data (60 MHz, $CDCl_3$ solvent, $\delta$ value: ppm)

3.45 (3H, s)

3.60–3.97 (4H, m)

4.00 (3H, s)

6.83–8.13 (7H, m)

Example 20

Preparation of 3-(2-chloro-6-fluorophenyl)-5-(2-chloro-5-perfluorobutylphenyl) 1-methyl-1H-1,2,4-triazole (Compound No. 116)

A mixture of N-methyl-N-(benzenesulfonyl)-2-chloro-6-fluorobenzohydrazonoyl chloride (1.70 g), 2-chloro-5-perfluorobutylbenzonitrile (1.75 g), anhydrous iron (III) chloride (0.73 g) and o-dichlorobenzene (10 ml) is stirred at an oil bath temperature of 130° C. for 2 hours. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexaneethyl acetate as eluent to give 0.68 g of desired compound (refractive index: 1.5110).

NMR data (60 MHz, $CDCl_3$ solvent, $\delta$ value: ppm)

3.87 (3H, s)

6.80–7.97 (6H, m)

Example 21

Preparation of 3-(2-chlorophenyl)-5-(2-chloro-5-perfluorohexylphenyl) 1-methyl-1H-1,2,4triazole (Compound No. 119)

A mixture of N-methyl-N-(p-toluenesulfonyl)-2-chlorobenzohydrazonoyl chloride (0.51 g), 2-chloro-5-perfluorohexylbenzonitrile (0.70 g), anhydrous aluminum chloride (0.20 g) and o-dichlorobenzene (5 ml) is stirred at an oil bath temperature of 140° C. for 1 hour. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexane-ethyl acetate as eluent to give 0.15 g of desired compound (melting point: 70.0°–76.0° C.).

NMR data (60 MHz, $CDCl_3$ solvent, $\delta$ value: ppm)

3.85 (3H, s)

7.13–8.06 (7H, m)

Example 22

Preparation of 3-(2-chloro-6-fluorophenyl)-5-(2-chloro-5-perfluorohexylphenyl) 1-methyl-1H-1,2,4-triazole (Compound No. 120)

A mixture of N-methyl-N-(p-toluenesulfonyl)-2-chloro-6-fluorobenzohydrazonoyl chloride (0.73 g), 2-chloro-5-perfluorohexylbenzonitrile (1.00 g), anhydrous iron (III) chloride (0.36 g) and o-dichlorobenzene (5 ml) is stirred at an oil bath temperature of 140° C. for 1 hour. After cooling, the reaction mixture is dissolved in chloroform (100 ml), washed with dilute hydrochloric acid, dilute aqueous solution of sodium hydroxide and saline in this order, dried over anhydrous magnesium sulfate and concentrated under reduced pressure. The concentrate is purified by silica gel column chromatography using mixed solvent of hexaneethyl acetate as eluent to give 0.15 g of desired compound (melting point: 78.0°–82.0° C.).

NMR data (60 MHz, CDCl$_3$ solvent, δ value: ppm)
3.86 (3H, s)
6.86–7.86 (6H, m)

Example 23

Preparation of 3-(2-chlorophenyl)-5-(2-chloro-4-allyloxyphenyl) 1-methyl-1H-1,2,4-triazole (Compound No. 138).

Ethyl 2-chlorobenzimidate (2.60 g) and triethylamine (1.10 g) are dissolved in toluene (20 ml) and 2-chloro-4-allyloxybenzoyl chloride (2.20 g) is added dropwise thereto within a range of 5° C.–10° C. with stirring, It is stirred at room temperature for 1 hour and further heated under reflux for 30 minutes. After cooling to room temperature, the reaction solution is added with toluene (20 ml) and washed with dilute sulfuric acid and saline and the organic layer is dried over anhydrous magnesium sulfate. The organic layer is added with monomethyl hydrazine (2.00 g) and stirred at room temperature for 5 hours. On completion of the reaction, the reaction mixture is washed with dilute sulfuric acid and saline, dried over anhydrous magnesium sulfate and concentrated under reduced pressure. The concentrate is purified by silica gel column chromatography using mixed solvent of hexane-ethyl acetate as eluent to give 0.60 g of desired compound (refractive index: 1.6083).

NMR data (60 MHz, CDCl$_3$ solvent, δ value: ppm)
3.85 (3H, s)
4.50–4.80 ( 2H, m)
5.25–5.62 (2H, m)
5.77–6.40 ( 1H, m)
6.82–8.16 (7H, m)

Example 24

Preparation of 3-(2-chlorophenyl)-5-(2-chloro-4-propargyroxyphenyl) 1-methyl-1H-1,2,4-triazole (Compound No. 145)

Ethyl 2-chlorobenzimidate (3.00 g) and triethylamine (1.50 g) are dissolved in toluene (20 ml) and 2-chloro-4-propargyroxybenzoyl chloride (2.30 g) is added dropwise thereto within a range of 5° C.–10° C. with stirring. It is stirred at room temperature for 1 hour and further heated under reflux for 30 minutes. After cooling to room temperature, the reaction solution is added with toluene (20 ml) and washed with dilute sulfuric acid and saline and the organic layer is dried over anhydrous magnesium sulfate. The organic layer is added with monomethyl hydrazine (2.00 g) and stirred at room temperature for 4 hours. On completion of the reaction, the reaction mixture is washed with dilute sulfuric acid and saline, dried over anhydrous magnesium sulfate and concentrated under reduced pressure. The concentrate is purified by silica gel column chromatography using mixed solvent of hexane-ethyl acetate as eluent to give 0.60 g of desired compound (melting point: 103.0–105.0).

NMR data (60 MHz, CDCl$_3$ solvent, δ value: ppm)
2.47–2.71 (1H, m)
3.83 (3H, s)
4.75 (2H, d)
6.83–8.20 (7H, m)

Example 25

Preparation of 3-(2-chloro-6-fluorophenyl)-5-[4-fluoro-3-(4-trifluoromethoxyphenyl)phenyl]1-methyl-1H-1,2,4-triazole (Compound No. 157)

A mixture of N-methyl-N-(methanesulfonyl)-2-chloro-6-fluorobenzohydrazonoyl chloride (1.50 g), 4-fluoro-3-(4-trifluoromethoxyphenyl)benzonitrile (1.43 g), anhydrous iron (III) chloride (0.90 g) and o-dichlorobenzene (5 ml) is stirred at an oil bath temperature of 140° C. for 30 minutes. After cooling, the reaction mixture is dissolved in ethylacetate (200 ml), washed with water, dried over anhydrous magnesium sulfate and concentrated under reduced pressure. The concentrate is purified by silica gel column chromatography using mixed solvent of hexane-ethyl acetate as eluent to give 1.90 g of desired compound (melting point: 117.0°–119.0° C.).

NMR data (60 MHz, CDCl$_3$ solvent, δ value: ppm)
4.10 (3H, s)
6.80–7.90 (10H, m)

Example 26

Preparation of 3-(2-chloro-6-fluorophenyl)-5-[2-chloro-4-(4-trifluoromethoxyphenyl)phenyl]1-methyl-1H-1,2,4-triazole (Compound No. 158)

A mixture of N-methyl-N-(methanesulfonyl)-2-chloro-6-fluorobenzohydrazonoyl chloride (1.50 g), 4-(4-trifluoromethoxyphenyl)benzonitrile (1.56 g), anhydrous iron (III) chloride (0.90 g) and chlorobenzene (20 ml) is stirred at an oil bath temperature of 140° C. for 1 hour. After cooling, the reaction mixture is dissolved in chloroform (300 ml), washed with dilute hydrochrolic acid, dilute aqueous solution of sodium hydroxide and saline in this order, dried over anhydrous magnesium sulfate and concentrated under reduced pressure. The concentrate is purified by silica gel column chromatography using mixed solvent of hexane-ethyl acetate as eluent to give 1.80 g of desired compound (refractive index: 1.5925).

NMR data (60 MHz, CDCl$_3$ solvent, δ value: ppm)
3.90 (3H, s)
6.90–7.70 (10H, m)

Example 27

Preparation of 5-[3-chloro-4-(3,4-dichlorobenzyl)phenyl]3-(2-chloro-6-fluorophenyl)-1-methyl-1H-1,2,4-triazole (Compound No. 161)

A mixture of N-methyl-N-(benzenesulfonyl)-2-chloro-6-fluorobenzohydrazonoyl chloride (1.00 g), 3-chloro-4-(3,4-dichlorobenzyl)benzonitrile (0.93 g), anhydrous iron (III) chloride (0.50 g) and o-dichtorobenzene (5 ml) is stirred at an oil bath temperature of 140° C. for 1 hour. After cooling, the reaction mixture is dissolved in chloroform (300 ml), washed with dilute hydrochrolic acid, dilute aqueous solution of sodium hydroxide and saline in this order, dried over anhydrous magnesium sulfate and concentrated under reduced pressure. The concentrate is purified by silica gel column chromatography using mixed solvent of hexaneethyl acetate as eluent to give 0.64 g of desired compound (melting point: 179.0°–185.0° C.).

NMR data (60 MHz, CDCl$_3$ solvent, δ value: ppm)
4.03 (3H, s)

4.23 (2H, s)

6.67–7.86 (9H, m)

Example 28

Preparation of 3-(2-chloro-6-fluorophenyl)-5-[3-chloro-4(2-chloro-4-trifluoromethylphenoxymethyl)phenyl]-1-methyl-1H-1,2,4-triazole (Compound No. 196)

To 30 ml of N,N-dimethylformamide are added 2-chloro-4-trifluoromethyl phenol (0.29 g) and potassium carbonate (0.25 g) and 5-(4-bromomethyl-3-chlorophenyl) 3-(2-chloro-6-fluorophenyl)-1-methyl-1H-1,2,4-triazole (0.60 g) is added thereto at room temperature with stirring, which is stirred at 120° C. for 1 hour. On completion of the reaction, the reaction solution is cooled to room temperature, poured into water and extracted with toluene. The organic layer is washed with water, dried over anhydrous magnesium sulfate and concentrated under reduced pressure. The concentrate is purified by silica gel column chromatography to give 0.61 g of desired compound (melting point: 113.0°–114.0° C.).

NMR data (60 MHz, CDCl$_3$ solvent, δ value: ppm)

4.10 (3H, s)

5.30 (2H, s)

6.87–8.10 (9H, m)

Example 29

Preparation of 3-(2-chloro-6-fluorophenyl)-5-[3-chloro-4(2-fluoro-4trifluoromethylphenoxymethyl)phenyl]-1-methyl-1H-1,2,4-triazole (Compound No. 197)

To 100 ml of N,N-dimethylformamide are added 5-(3-chloro-4-chloromethylphenyl)-3(2-chloro-6-fluorophenyl)-1-1H-1,2,4-triazole (1.60 g) and potassium carbonate (0.60 g) and 2-fluoro-4-trifluoromethyl phenol (0.80 g) is added thereto at room temperature with stirring, which is stirred at 70° C. for 3 hours. On completion of the reaction, the reaction solution is cooled to room temperature, poured into water and extracted with ethyl acetate. The organic layer is washed with water, dried over anhydrous magnesium sulfate and concentrated under reduced pressure. The concentrate is purified by silica gel column chromatography to give 1.62 g of desired compound (refractive index: 1.6010).

NMR data (60 MHz, CDCl$_3$ solvent, δ value: ppm)

4.10 (3H, s)

5.31 (2H, s)

6.75–8.00 (9H, m)

Example 30

Preparation of 3-(2-chloro-6-fluorophenyl)-5-[3-chloro-4(4-trifluoromethylphenoxymethyl)phenyl]-1-methyl-1H-1,2,4-triazole (Compound No. 199)

To 30 ml of N,N-dimethylformamide are added 4-trifluoromethyl phenol (0.77 g) and potassium carbonate (0.72 g) and 5-(4-bromomethyl-3-chlorophenyl)-3(2-chloro-6-fluorophenyl)-1-methyl-1H-1,2,4-triazole (1.60 g) is added thereto at room temperature with stirring, which is stirred at 120° C. for 1 hour. On completion of the reaction, the reaction solution is cooled to room temperature, poured into water and extracted with toluene. The organic layer is washed with water, dried over anhydrous magnesium sulfate and concentrated under reduced pressure. The concentrate is purified by silica gel column chromatography to give 1.50 g of desired compound (refractive index: 1.5961).

NMR data (60 MHz, CDCl$_3$ solvent, δ value: ppm)

4.08 (3H, s)

5.23 (2H, s)

6.87–7.47 (7H, m)

7.65 (2H, s)

7.83 (1H, s)

Example 31

Preparation of 3-(2-chloro-6-fluorophenyl)-5-[3-chloro-4(4-trifluoromethoxyphenoxymethyl)phenyl]-1-methyl-1H-1,2,4-triazole (Compound No. 201)

To 30 ml of N,N-dimethylformamide are added 4-trifluoromethoxy phenol (0.33 g) and potassium carbonate (0.25 g) and 5-(4-bromomethyl-3-chlorophenyl)-3(2-chloro-6-fluorophenyl)-1-methyl-1H-1,2,4-triazole (0.70 g) is added thereto at room temperature with stirring, which is stirred at 120° C. for 1 hour. On completion of the reaction, the reaction solution is cooled to room temperature, poured into water and extracted with toluene. The organic layer is washed with water, dried over anhydrous magnesium sulfate and concentrated under reduced pressure. The concentrate is purified by silica gel column chromatography to give 0.83 g of desired compound (refractive index: 1.5701).

NMR data (60 MHz, CDCl$_3$ solvent, δ value: ppm)

4.08 (3H, s)

5.19 (2H, s)

6.70–7.40 (7H, m)

7.65 (1H, s)

Example 32

Preparation of 3-(2-chloro-6-fluorophenyl)-5-(2-chloro-4-phenoxyphenyl) 1-methyl-1H-1,2,4-triazole (Compound No. 241)

A mixture of N-methyl-N-(p-toluenesulfonyl)-2-chloro-6-fluorobenzohydrazonoyl chloride (3.30 g), 2-chloro-4-phenoxybenzonitrile (2.30 g), anhydrous iron (III) chloride (1.60 g) and o-dichlorobenzene (10 ml) is stirred at an oil bath temperature of 140° C. for 1 hour. After cooling, the reaction mixture is dissolved in chloroform (100 ml), washed with dilute hydrochrolic acid, dilute aqueous solution of sodium hydroxide and saline in this order, dried over anhydrous magnesium sulfate and concentrated under reduced pressure. The concentrate is purified by silica gel column chromatography using mixed solvent of hexane-ethyl acetate as eluent to give 0.15 g of desired compound (melting point: 135.0°–140.0° C.).

NMR data (60 MHz, CDCl$_3$ solvent, δ value: ppm)

3.91 (3H, s)

6.90–8.06 (11H, m)

Example 33

Preparation of 3-(2-chloro-6-fluorophenyl)-5-[3-chloro-4(2,6-dichloro-4-trifluoromethylphenoxy)-phenyl]-1-methyl-1H-1,2,4-triazole (Compound No. 259)

Ethyl 2-chloro-6-fluorobenzimidate (1.80 g) and triethylamine (1.20 g) are dissolved in toluene (50 ml) and 3-chloro-4-(2,6-dichloro-4-trifluoromethylphenoxy)benzoyl chloride (3.70 g) is added dropwise thereto at room temperature with stirring, which is stirred at 100° C. for 3 hours. After cooling to room temperature, the reaction solution is added with toluene (50 ml) and washed with dilute hydrochloric acid and saline and the organic layer is dried over anhydrous magnesium sulfate. The reaction solution is added with monomethyl hydrazine (0.80 g) and stirred at 100° C. for 3 hours. On completion of the reaction, the reaction mixture is washed with dilute hydrochloric acid and saline, dried over anhydrous magnesium sulfate and concentrated under reduced pressure. The concentrate is purified by silica gel column chromatography using mixed solution of hexane-ethyl acetate as eluent to give 1.50 g of desired compound (melting point: 67.0–72.0).

NMR data (60 MHz, CDCl$_3$ solvent, δ value: ppm)
4.05 (3H, s)
6.40–7.95 (8H, m)

Example 34

Preparation of 3-(2-chloro-6-fluorophenyl)-5-[3-chloro-4(2-chloro-4-trifluoromethylbenzyloxy)-phenyl]-1-methyl-1H-1,2,4-triazole (Compound No. 273)

To 20 ml of N,N-dimethylformamide are added 3-(2-chloro-6-fluorophenyl)-5(3-chloro-4-hydroxyphenyl)-1-methyl-1H-1,2,4-triazole (0.70 g) and potassium carbonate (0.31 g) and 2-chloro-4-trifluoromethylbenzyl chloride (0.50 g) is added thereto at room temperature with stirring, which is stirred at 120° C. for 5 hours. On completion of the reaction, the reaction solution is cooled to room temperature, poured into water and extracted with ethyl acetate. The organic layer is washed with water, dried over anhydrous magnesium sulfate and concentrated under reduced pressure. The concentrate is purified by silica gel column chromatography to give 0.80 g of desired compound (melting point: 156.0°–159.0° C.).

NMR data (60 MHz, CDCl$_3$ solvent, δ value: ppm)
4.05 (3H, s)
5.30 (2H, S)
6.80–7.95 (9H, m)

Example 35

Preparation of 3-(2-chloro-6-fluorophenyl)-5-[3-chloro-4(2-fluoro-4-trifluoromethylbenzyloxy)-phenyl]-1-methyl-1H-1,2,4-triazole (Compound No. 274)

To 20 ml of N,N-dimethylformamide are added 3-(2-chloro-6-fluorophenyl) 5-[3-chloro-4-hydroxyphenyl)-1-methyl-1H-1,2,4-triazole (0.90 g) and potassium carbonate (0.40 g) and 2-fluoro-4-trifluoromethylbenzyl chloride (0.50 g) is added thereto at room temperature with stirring, which is stirred at 120° C. for 5 hours. On completion of the reaction, the reaction solution is cooled to room temperature, poured into water and extracted with ethyl acetate. The organic layer is washed with water, dried over anhydrous magnesium sulfate and concentrated under reduced pressure. The concentrate is purified by silica gel column chromatography to give 0.60 g of desired compound (melting point: 109.0°–111.0° C.).

NMR data (60 MHz, CDCl$_3$ solvent, δ value: ppm)
4.00 (3H, s)
5.25 (2H, s)
6.80–7.90 (9H, m)

Example 36

Preparation of 3-(2-chloro-6-fluorophenyl)-5-[3-chloro-4(4-trifluoromethylbenxyloxy)phenyl]-1-methyl-1H-1,2,4-triazole (Compound No. 275)

Ethyl 2-chloro-6-fluorobenzimidate (2.40 g) and triethylamine (1.20 g) are dissolved in toluene (50 ml) and 3-chloro-4-(4-trifluoromethylbenzyloxy)benzoyl chloride (3.50 g) is added dropwise thereto at room temperature with stirring, which is stirred at 100° C. for 3 hours. After cooling to room temperature, the reaction solution is added with toluene (50 ml) and washed with dilute hydrochloric acid and saline and the organic layer is dried over anhydrous magnesium sulfate. The organic layer is added with monomethyl hydrazine (0.90 g) and stirred at 100° C. for 3 hours. On completion of the reaction, the reaction mixture is washed with dilute hydrochloric acid and saline, dried over anhydrous magnesium sulfate and concentrated under reduced pressure. The concentrate is purified by silica gel column chromatography using mixed solution of hexane-ethyl acetate as eluent to give 2.20 g of desired compound (melting point: 43.0°–47.0° C.).

NMR data (60 MHz, CDCl$_3$ solvent, δ value: ppm)
4.05 (3H, s)
5.25 (2H, s)
6.90–7.95 (10H, m)

Example 37

Preparation of 5-[3-chloro-4-(4-trifluoromethylbenzyloxy)phenyl]3-(2,6-difluorophenyl)-1-methyl-1H-1,2,4-triazole (Compound No. 276)

Ethyl 2,6-difluorobenzimidate (2.20 g) and triethylamine (1.20 g) are dissolved in toluene (50 ml) and 3-chloro-4-(4-trifluoromethylbenzyloxy)benzoyl chloride (3.50 g) is added dropwise thereto at room temperature with stirring, which is stirred at 100° C. for 3 hours. After cooling to room temperature, the reaction solution is added with toluene (50 ml) and washed with dilute hydrochloric acid and saline and the organic layer is dried over anhydrous magnesium sulfate. The organic layer is added with monomethyl hydrazine (0.90 g) and stirred at 100° C. for 3 hours. On completion of the reaction, the reaction mixture is washed with dilute hydrochloric acid and saline, dried over anhydrous magnesium sulfate and concentrated under reduced pressure. The concentrate is purified by silica gel column chromatography using mixed solution of hexane-ethyl acetate as eluent to give 2.00 g of desired compound (melting point: 171.0°–177.0° C.).

NMR data (60 MHz, CDCl$_3$ solvent, δ value: ppm)
4.00 (3H, s)
5.20 (2H, s)
6.65–7.90 (10H, m)

Example 38

Preparation of 3-(2-chloro-6-fluorophenyl)-5-[3-chloro-4(4-trifluoromethoxybenzyloxy)phenyl]-1-methyl-1H-1,2,4-triazole (Compound No. 277)

Ethyl 2-chloro-6-fluorobenzimidate (2.40 g) and triethylamine (1.20 g) are dissolved in toluene (50 ml) and 3-chloro-4-(4-trifluoromethoxybenzyloxy)benzoyl chloride (3.70 g) is added dropwise thereto at room temperature with stirring, which is stirred at 100° C. for 3 hours. After cooling to room temperature, the reaction solution is added with toluene (50 ml) and washed with dilute hydrochloric acid and saline and the organic layer is dried over anhydrous magnesium sulfate. The organic layer is added with monomethyl hydrazine (0.90 g) and stirred at 100° C. for 3 hours. On completion of the reaction, the reaction mixture is washed with dilute hydrochloric acid and saline, dried over anhydrous magnesium sulfate and concentrated under reduced pressure. The concentrate is purified by silica gel column chromatography using mixed solution of hexane-ethyl acetate as eluent to give 2.50 g of desired compound (refractive index: 1.5680).

NMR data (60 MHz, $CDCl_3$ solvent, δ value: ppm)
4.00 (3H, s)
5.10 ( 2H, s )
6.85–7.90 ( 10H, m)

Example 39

Preparation of 5-[3-chloro-4-(4-trifluoromethoxybenzyloxy)phenyl]3-(2,6-difluorophenyl)-1-methyl-1H-1,2,4-triazole (Compound No. 278)

Ethyl 2,6-difluorobenzimidate (2.20 g) and triethylamine (1.20 g) are dissolved in toluene (50 ml) and 3-chloro-4-(4-trifluoromethoxybenzyloxy)benzoyl chloride (3.70 g) is added dropwise thereto at room temperature with stirring, which is stirred at 100° C. for 3 hours. After cooling to room temperature, the reaction solution is added with toluene (50 ml) and washed with dilute hydrochloric acid and saline and the organic layer is dried over anhydrous magnesium sulfate. The organic layer is added with monomethyl hydrazine (0.90 g) and stirred at 100° C. for 3 hours. On completion of the reaction, the reaction mixture is washed with dilute hydrochloric acid and saline, dried over anhydrous magnesium sulfate and concentrated under reduced pressure. The concentrate is purified by silica gel column chromatography using mixed solution of hexane-ethyl acetate as eluent to give 2.50 g of desired compound (melting point: 132.0°–136.0° C.).

NMR data (60 MHz, $CDCl_3$ solvent, δ value: ppm)
4.00 (3H, s)
5.10 (2H, s)
6.70–8.20 (10H, m)

Example 40

Preparation of 3-(2-chloro-6-fluorophenyl)-5-[2-chloro-4(3-chloro-5-trifluoromethylpyridine-2-yloxymethyl)phenyl]1-methyl-1H-1,2,4-triazole (Compound No. 317)

3-(2-chloro-6-fluorophenyl)-5-(2-chloro-4-hydroxymethylphenyl) 1-methyl-1H-1,2,4-triazole (0.50 g) is dissolved in 1,2-dimethoxyethane (20 ml) and cooled to 0° C., to which is added sodium hydride (60%, 0.07 g) and the reaction mixture is stirred for 15 minutes. Then, a solution of 2,3-dichloro-5-trifluoromethyl pyridine (0.34 g) in 1,2-dimethoxyethane (10 ml) is added dropwise and stirred for 3 hours. On completion of the reaction, the reaction solution is warmed to room temperature and poured into water and extracted with ether. The organic layer is washed with water, dried over anhydrous magnesium sulfate and concentrated under reduced pressure. The concentrate is purified by silica gel column chromatography to give 0.62 g of desired compound.

NMR data (60 MHz, $CDCl_3$ solvent, δ value: ppm)
3.83 (3H, s)
5.50 (2H, s)
6.83–8.37 (8H, m)

Example 41

Preparation of 5-[3-chloro-4-(3,5-dichloropyridine-2-yloxymethyl)phenyl]-3(2-chloro-6-fluorophenyl)-1-methyl-1H-1,2,4-triazole (Compound No. 330)

Sodium hydride (60%, 0.12 g) is added to 1,2-dimethoxyethane (50 ml) and a solution of 3-(2-chloro-6-fluorophenyl)-5-(3-chloro-4-hydroxymethylphenyl) 1-methyl-1H-1,2,4-triazole (1.00 g) in 1,2-dimethoxyethane (20 ml) is added dropwise thereto at −5° C. and stirred for 20 minutes. The reaction solution is added dropwise with a solution of 2,3,5-trichloropyridine (0.60 g) in 1,2-dimethoxyethane (20 ml) at −5° C. for 10 minutes with stirring. The reaction mixture is warmed to room temperature, poured into water and extracted with ethyl acetate. The organic layer is washed with water, dried over anhydrous magnesium sulfate and concentrated under reduced pressure. The concentrate is purified by silica gel column chromatography to give 0.40 g of desired compound (melting point: 153.0°–155.0° C.).

NMR data (60 MHz, $CDCl_3$ solvent, δ value: ppm)
4.06 (3H, s)
5.48 (2H, s)
6.75–7.30 (3H, m)
7.50–8.00 (5H, m)

Example 42

Preparation of 5-[3-chloro-4-(3-chloro-5-trifluoromethylpyridine-2-yloxymethyl)phenyl]-3(2-chloro-6-fluorophenyl)-1-methyl-1H-1,2,4-triazole (Compound No. 332)

Sodium hydride (60%, 0.16 g) is added to 1,2-dimethoxyethane (50 ml) and a solution of 3-(2-chloro-6-fluorophenyl)-5-(3-chloro 4-hydroxymethylphenyl)-1-methyl-1H-1,2,4-triazole (1.20 g) in 1,2-dimethoxyethane (20 ml) is added dropwise thereto at −5° C. with stirring. To the reaction solution is added dropwise a solution of 2,3-dichloro-5-trifluoromethyl pyridine (0.80 g) in 1,2-dimethoxyethane (20 ml) at −5° C. for 10 minutes, which is further stirred for 15 minutes. On completion of the reaction, the reaction solution is warmed to room temperature, poured into water and extracted with ethyl acetate. The organic layer is washed with water, dried over anhydrous magnesium sulfate and concentrated under reduced pressure. The concentrate is purified by silica gel column chromatography to give 1.10 g of desired compound (melting point: 47.0°–49.0° C.).

NMR data (60 MHz, $CDCl_3$ solvent, δ value: ppm)
4.06 (3H, s)
5.57 (2H, s)
6.84–7.50 (3H, m)
7.60–7.75 (4H, m)
8.30 (1H, s)

Example 43

Preparation of 5-[3-chloro-4-(5-trifluoromethylpyridine-2-yloxymethyl)phenyl]-3(2-chloro-6-fluorophenyl)-1-methyl-1H-1,2,4-triazole (Compound No. 334)

Sodium hydride (60%, 0.12 g) is added to 1,2-dimethoxyethane (50 ml) and a solution of 3-(2-chloro-6-fluorophenyl)-5-(3-chloro 4-hydroxymethylphenyl)-1-methyl-1H-1, 2,4-triazole (1.00 g) in 1,2-dimethoxyethane (20 ml) is added dropwise thereto at −5° C., which is stirred for 15 minutes. To the reaction solution is added dropwise a solution of 2-chloro-5-trifluoromethyl pyridine (0.60 g) in 1,2-dimethoxyethane (20 ml) at −5° C., which is stirred for 15 minutes. The reaction mixture is warmed to room temperature, poured into water and extracted with ethyl acetate. The organic layer is washed with water, dried over anhydrous magnesium sulfate and concentrated under reduced pressure. The concentrate is purified by silica gel column chromatography to give 0.80 g of desired compound (refractive index: 1.5879).

NMR data (60 MHz, CDCl$_3$ solvent, δ value: ppm)
4.06 (3H, s)
5.57 (2H, s)
6.75–8.42 (9H, m)

Example 44

Preparation of 5-[4-chloro-3-(5-trifluoromethylpyridine-2-yloxy)phenyl]-3(2,6-difluorophenyl)-1-methyl-1H-1,2,4-triazole (Compound No. 377)

A mixture of N-methyl-N-(benzenesulfonyl)-2,6-difluorobenzohydrazonoyl chloride (0.90 g), 4-chloro-3-(5-trifluoromethylpyridine-2-yloxy)benzonitrile (0.90 g), anhydrous iron (III) chloride (0.50 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.30 g of desired compound.

NMR data (60 MHz, CDCl$_3$ solvent, δ value: ppm)
4.02 (3H, s)
6.64–7.98 (8H, m)
8.20–8.38 (1H, m)

Example 45

Preparation of 3-(2-chloro-6-fluorophenyl)-5-[4-chloro-3-(5-trifluoromethylpyridine 2-yloxy)phenyl]-1-methyl-1H-1,2,4-triazole (Compound No. 378)

A mixture of N-methyl-N-(p-toluenesulfonyl)-2-chloro-6-fluorobenzohydrazonoyl chloride (1.00 g), 4-chloro-3-(5-trifluoromethylpyridine-2-yloxy)benzonitrile (0.90 g), anhydrous iron (III) chloride (0.50 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.40 g of desired compound.

NMR data (60 MHz, CDCl$_3$ solvent, δ value: ppm)
4.12 (3H, s)
6.92–8.11 (8H, m)
8.33–8.50 (1H, m)

Example 46

Preparation of 3-(2-chlorophenyl)-5-[2-chloro-4-(5-trifluoromethylpyridine-2-yloxy)phenyl]1-methyl-1H-1,2,4-triazole (Compound No. 389)

A mixture of N-methyl-N-(benzenesulfonyl)-2-chlorobenzohydrazonoyl chloride (2.05 g), 2-chloro-4-(5-trifluoromethylpyridine-2-yloxy)benzonitrile (1.88 g), anhydrous iron (III) chloride (1.07 g) and o-dichlorobenzene (10 ml) is stirred at an oil bath temperature of 140° C. for 30 minutes. After cooling, it is dissolved in chloroform (300 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 1.87 g of desired compound (melting point: 104.0°–108.0° C.).

NMR data (60 MHz, CDCl$_3$ solvent, δ value: ppm)
3.88 (3H, s)
6.90–8.40 (10H, m)

Example 47

Preparation of 3-(2-chloro-6-fluorophenyl)-5-[2-chloro-4-(5-trifluoromethylpyridine 2yloxy)phenyl]-1-methyl-1H-1,2,4-triazole (Compound No. 390)

A mixture of N-methyl-N-(p-toluenesulfonyl)-2-chloro-6-fluorobenzohydrazonoyl chloride (2.25 g), 2-chloro-4-(5-trifluoromethylpyridine-2-yloxy)benzonitrile (1.88 g), anhydrous iron (III) chloride (1.07 g) and o-dichlorobenzene (5 ml) is stirred at an oil bath temperature of 140° C. for 30 minutes. After cooling, it is dissolved in chloroform (300 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 1.54 g of desired compound (melting point: 139.0°–141.0° C.).

NMR data (60 MHz, CDCl$_3$ solvent, δ value: ppm)
3.90 (3H, s)
6.90–8.40 (9H, m)

Example 48

Preparation of 3-(2-chloro-6-fluorophenyl)-5-[3,5-dichloro-4(3-chloro-5-trifluoromethylpyridine-2-yloxy)phenyl]-1-1H-1,2,4-triazole (Compound No. 401)

A mixture of N-methyl-N-(p-toluenesulfonyl)-2-chloro-6-fluorobenzohydrazonoyl chloride (1.00 g), 3,5-dichloro-4-(3-chloro-5-trifluoromethylpyridine-2yloxy)benzonitrile (1.00 g), anhydrous iron (III) chloride (0.50 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.60 g of desired compound.

NMR data (60 MHz, CDCl$_3$ solvent, δ value: ppm)
4.10 (3H, s)
6.73–7.52 (3H, m)
7.80 (2H, s)
7.97–8.10 (1H, m)
8.12–8.26 (1H, m)

Example 49

Preparation of 5-[3-chloro-4-(3-chloro-5-trifluoromethylpyridine-2-yloxy)phenyl]3-(2,6-difluorophenyl)-1-methyl-1H-1,2,4-triazole (Compound No. 409)

A mixture of N-methyl-N-(benzenesulfonyl)-2,6-difluorobenzohydrazonoyl chloride (0.90 g), 3-chloro-4-(3-chloro-5-trifluoromethylpyridine-2-yloxy)benzonitrile (0.90 g), anhydrous iron (III) chloride (0.50 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.70 g of desired compound.

NMR data ( 60 MHz, CDCl$_3$ solvent, δ value: ppm)
4.10 (3H, s)
6.72–8.06 (7H, m)
8.14–8.30 (1H, m)

Example 50

Preparation of 5-[3-chloro-4-(3-chloro-5-trifluoromethylpyridine-2-yloxy)phenyl]3-(2-chloro-6-fluorophenyl)-1-methyl-1H-1,2,4-triazole (Compound No. 410)

A mixture of N-methyl-N-(p-toluenesulfonyl)-2-chloro-6-fluorobenzohydrazonoyl chloride (0.90 g), 3-chloro-4-(3-chloro-5-trifluoromethylpyridine-2yloxy)benzonitrile (0.80 g), anhydrous iron (III) chloride (0.40 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.60 g of desired compound.

NMR data (60 MHz, CDCl$_3$ solvent, δ value: ppm)
4.16 (3H, s)
6.92–8.16 (7H, m)
8.24–8.40 (1H, m)

Example 51

Preparation of 5-[3-chloro-4-(5-trifluoromethylpyridine-2-yloxy)phenyl]-3(2,6-difluorophenyl)-1-methyl-1H-1,2,4-triazole (Compound No. 412)

A mixture of N-methyl-N-(benzenesulfonyl)-2,6-difluorobenzohydrazonoyl chloride (1.72 g), 3-chloro-4-(5-trifluoromethylpyridine-2-yloxy)benzonitrile (1.50 g), anhydrous iron (III) chloride (0.85 g) and o-dichlorobenzene (10 ml) is stirred at an oil bath temperature of 140° C. for 30 minutes. After cooling, it is dissolved in chloroform (200 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent and washed with hexane to give 1.25 g of desired compound.

NMR data (60 MHz, CDCl$_3$ solvent, δ value: ppm)
3.11 (3H, s)
6.80–8.40 (9H, m)

Example 52

Preparation of 3-(2-chloro-6-fluorophenyl)-5-[3-chloro-4-(5-trifluoromethylpyridine 2yloxy)phenyl]-1-methyl-1H-1,2,4-triazole (Compound No. 413)

To N,N-dimethylformamide (50 ml) are added 3-(2-chloro-6-fluorophenyl)-5-(3-chloro-4-hydroxyphenyl 5-(3-chloro-4-hydroxyphenyl)-1-methyl-1H-1,2,4-triazole (3.04 g), 2-chloro-5-trifluoromethyl pyridine (1.70 g) and potassium carbonate (1.40 g), which is heated at 120° C. for 2 hours with stirring. After cooling to room temperature, the reaction solution is poured into water and extracted with ethyl acetate, and the layer is washed with water and dried over anhydrous magnesium sulfate. After the concentration under reduced pressure, the crude solid is purified by silica gel column chromatography using mixed solution of hexane-ethyl acetate as eluent to give 3.30 g of desired compound (melting point: 116.0°–117.0° C.).

NMR data (60 MHz, CDCl$_3$ solvent, δ value: ppm)
4.10 (3H, s)
6.90–8.30 ( 9H, m)

Example 53

Preparation of 3-(2-chloro-6-fluorophenyl)-5-[3-perfluorobutyl-4(3-chloro-5-trifluoromethyl-pyridine-2-yloxymethyl)phenyl]-1-methyl-1H-1,2,4-triazole (Compound No. 451)

3-(2-chloro-6-fluorophenyl)-1-methyl-5-(3-perfluorobutyl-4-hydroxymethylphenyl) 1H-1,2,4-triazole (1.00 g) is dissolved in 1,2-dimethoxyethane (20 ml) and cooled to 0° C.. It is added with sodium hydride (60%, 0.08 g) and stirred for 30 minutes. A solution of 2,3-dichloro-5-trifluoromethyl pyridine (0.44 g) in 1,2-dimethoxyethane (10 ml) is added dropwise thereto and stirred for 3 hours. On completion of the reaction, the reaction solution is warmed to room temperature, poured into water and extracted with ether. The organic layer is washed with water, dried over anhydrous magnesium sulfate and concentrated under reduced pressure. The concentrate is purified by silica gel column chromatography to give 1.00 g of desired compound (melting point: 123.0°–127.0° C.).

NMR data (60 MHz, CDCl₃ solvent, δ value: ppm)
4.08 (3H, s)
5.73 (2H, s)
6.85–7.40 (4H, m)
7.75–8.27 (4H, m)

Example 54

Preparation of 3-(2-chloro-6-fluorophenyl)-5-[3-perfluorobutyl-4-(5-trifluoromethylpyridine 2-yloxymethyl)phenyl]-1-methyl-1H-1,2,4-triazole (Compound No. 453)

3-(2-chloro-6-fluorophenyl)-1-methyl-5-(3-perfluorobutyl-4-hydroxymethylphenyl) 1H-1,2,4-triazole (1.00 g) is dissolved in 1,2-dimethoxyethane (20 ml) and cooled to 0° C. It is added with sodium hydride (60%, 0.08 g) and stirred for 30 minutes. A solution of 2-chloro-5-trifluoromethyl pyridine (0.36 g) in 1,2-dimethoxyethane (10 ml) is added dropwise thereto and stirred for 5 hours. On completion of the reaction, the reaction solution is warmed to room temperature, poured into water and extracted with ether. The organic layer is washed with water, dried over anhydrous magnesium sulfate and concentrated under reduced pressure. The concentrate is purified by silica gel column chromatography to give 0.70 g of desired compound (refractive index: 1.5020).

NMR data (60 MHz, CDCl₃ solvent, δ value: ppm)
4.12 (3H, s)
5.70 (2H, s)
6.80–8.53 (9H, m)

Example 55

Preparation of 3-(2-chloro-6-fluorophenyl)-1-methyl-5-[3-methyl-4(4-trifluoromethoxyphenyl)-phenyl]-1H-1,2,4-triazole (Compound No. 457)

A mixture of N-methyl-N-(methanesulfonyl)-2-chloro-6-fluorobenzohydrazonoyl chloride (1.50 g), 3-methyl-4-(4-trifluoromethoxyphenyl)benzonitrile (1.42 g), anhydrous iron (III) chloride (0.90 g) and chlorobenzene (10 ml) is stirred at an oil bath temperature of 140° C. for 30 minutes. After cooling, it is dissolved in chloroform (300 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent and washed with hexane to give 1.64 g of desired compound (melting point: 117.0°–122.0° C.).

NMR data (60 MHz, CDCl₃ solvent, δ value: ppm)
2.23 (3H, s)
4.10 (3H, s)
6.90–7.70 (10H, m)

Example 56

Preparation of 3-(2-chlorophenyl)-1-methyl-5-[4-methyl-3-(5-trifluoromethylpyridine 2-yloxy)phenyl]-1H-1,2,4triazole (Compound No. 509)

A mixture of N-methyl-N-(p-toluenesulfonyl)-2-chlorobenzohydrazonoyl chloride (1.1 g), 4-methyl-3-(5-trifluoromethylpyridine-2-yloxy)benzonitrile (1.00 g), anhydrous iron (III) chloride (0.60 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.50 g of desired compound.

NMR data (60 MHz, CDCl₃ solvent, δ value: ppm)
2.26 (3H, s)
4.07 (3H, s)
6.95–8.16 (9H, m)
8.36–8.52 (1H, m)

Example 57

Preparation of 3-(2-chloro-6-fluorophenyl)-1-methyl-5-[4-methyl-3(5-trifluoromethylpyridine-2-yloxy)phenyl]-1H-1,2,4-triazole (Compound No. 510)

A mixture of N-methyl-N-(p-toluenesulfonyl)-2-chloro-6-fluorobenzohydrazonoyl chloride (1.10 g), 4-methyl-3-(5-trifluoromethylpyridine-2-yloxy)benzonitrile (0.90 g), anhydrous iron (III) chloride (0.60 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.60 g of desired compound.

NMR data (60 MHz, CDCl₃ solvent, δ value: ppm)
2.24 (3H, s)
4.12 (3H, s)
6.85–8.07 (8H, m)
8.36–8.52 (1H, m)

Example 58

Preparation of 3-(2-chloro-6-fluorophenyl)-5-[4-methoxy-3-(5-trifluoromethylpyridine 2-yloxy)phenyl]-1H-1,2,4-triazole (Compound No. 516)

A mixture of N-methyl-N-(p-toluenesulfonyl)-2-chloro-6-fluorobenzohydrazonoyl chloride (1.00 g), 4-methoxy-3-(5-trifluoromethylpyridine-2-yloxy)benzonitrile (0.90 g), anhydrous iron (III) chloride (0.50 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.50 g of desired compound.

NMR data (60 MHz, CDCl₃ solvent, δ value: ppm)
3.85 (3H, s)
4.14 (3H, s)
6.92–8.08 (8H, m)
8.35–8.52 (1H, m)

Example 59

Preparation of 3-(2,6-difluorophenyl)-5-[4-methoxy-3-(5-trifluoromethylpyridine 2-yloxy)phenyl]-1-methyl-1H-1,2,4-triazole (Compound No. 517)

A mixture of N-methyl-N-(benzenesulfonyl)-2,6-difluorobenzohydrazonoyl chloride (0.70 g), 4-methoxy-3-(5-trifluoromethylpyridine-2-yloxy)benzonitrile (0.80 g), anhydrous iron (III) chloride (0.50 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.30 g of desired compound.

NMR data (60 MHz, CDCl$_3$ solvent, δ value: ppm)
3.84 (3H, s)
4.10 (3H, s)
6.75–8.10 (8H, m)
8.30–8.47 (1H, m)

Example 60

Preparation of 3-(2-chloro-6-fluorophenyl)-5-[3-(3-chloro-5-trifluoromethylpyridine 2-yloxy)-5-methoxyphenyl]-1-methyl-1H-1,2,4-triazole (Compound No. 523)

A mixture of N-methyl-N-(p-toluenesulfonyl)-2-chloro-6-fluorobenzohydrazonoyl chloride (0.90 g), 3-(3-chloro-5-trifluoromethylpyridine-2-yloxy)-5-methoxybenzonitrile (0.80 g), anhydrous iron (III) chloride (0.80 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.60 g of desired compound.

NMR data (60 MHz, CDCl$_3$ solvent, δ value: ppm )
3.92 (3H, s)
4.12 (3H, s)
6.85–7.53 (6H, m)
7.96–8.06 (1H, m)
8.23–8.40 (1H, m)

Example 61

Preparation of 3-(2-chloro-6-fluorophenyl)-5-[3-methoxy-4-(5-trifluoromethylpyridine 2-yloxy)phenyl]-1-methyl-1H-1,2,4-triazole (Compound No. 524)

A mixture of N-methyl-N-(p-toluenesulfonyl)-2-chloro-6-fluorobenzohydrazonoyl chloride (3.75 g), 3-methoxy-4-(5-trifluoromethylpyridine-2-yloxy)benzonitrile (3.03 g), anhydrous iron (III) chloride (1.70 g) and o-dichlorobenzene (5 ml) is stirred at an oil bath temperature of 140° C. for 30 minutes. After cooling, it is dissolved in chloroform (300 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent and washed with hexane to give 2.80 g of desired compound.

NMR data (60 MHz, CDCl$_3$ solvent, δ value: ppm)
2.97 (3H, s)
3.07 (3H, s)
6.90–8.30 (9H, m)

Example 62

Preparation of 3-(2-chloro-6-fluorophenyl)-5-[4-(3-chloro-5-trifluoromethylpyridine 2-yloxy)-3-methoxyphenyl]-1-methyl-1H-1,2,4-triazole (Compound No. 526)

A mixture of N-methyl-N-(p-toluenesulfonyl)-2-chloro-6-fluorobenzohydrazonoyl chloride (0.90 g), 4-(3-chloro-5-trifluoromethylpyridine-2-yloxy)-3methoxybenzonitrile (0.90 g), anhydrous iron (III) chloride (0.50 g) and o-dichlorobenzene (5 ml) is stirred at an oil bath temperature of 140° C. for 30 minutes. After cooling, it is dissolved in chloroform (100 ml) and washed with dilute hydrochloric acid, dilute aqueous solution of sodium hydroxide and saline. Then, it is dried over anhydrous magnesium sulfate and concentrated under reduced pressure. The concentrate is purified by silica gel column chromatography using mixed solvent of hexane-ethyl acetate as eluent to give 0.60 g of desired compound.

NMR data (60 MHz, CDCl$_3$ solvent, δ value: ppm)
3.81 (3H, s)Z
4.13 (3H, s)
6.90–7.60 (6H, m)
7.93–8.06 (1H, m)
8.16–8.30 (1H, m)

Example 63

Preparation of 5-(2-chloro-4-hexylphenyl)-3-(2-chlorophenyl) 1-methyl-1H-1,2,4-triazole (Compound No. 40)

A mixture of N-methyl-N-phenylsulfonyl-2-chlorobenzamidrazone (3.24 g) and 2-chloro-4-hexylbenzoyl chloride (3.37 g) is stirred at an oil bath temperature of 170°–180° C. for 4 hours. After cooling to room temperature, it is added with ethyl acetate and the organic layer is washed with water. Then, it is dried over anhydrous magnesium sulfate and concentrated under reduced pressure. The concentrate is purified by silica gel column chromatography using mixed solvent of hexaneethyl acetate as eluent to give 0.85 g of desired compound (refractive index: 1.5830).

NMR data (60 MHz, CDCl$_3$ solvent, δ value: ppm)
0.90 (3H, t)
1.00–1.90 (SH, m)
2.67 (2H, t)
3.87 (3H, s)
7.10–7.60 (6H, m)
7.90–8.05 (1H, m)

Reference Example 1

Preparation of N-methyl-N-(benzenesulfonyl)-2-chlorobenzamidorazone

N-methyl-N-(benzenesulfonyl)-2-chlorobenzhydrazonoyl chloride (17.2 g) is dissolved in N,N-dimethylformamide (100 ml) and stirred at 60°–70° C. for 3 hours while introducing ammonia gas thereinto. After cooling, it is dissolved in 500 ml of ethyl acetate and washed with water. Then, it is dried over anhydrous magnesium sulfate and concentrated under reduced pressure and the crude solid is washed with hexane to give 15.4 g of desired compound (melting point: 94.0°–96.0° C.).

NMR data (60 MHz, CDCl$_3$ solvent, δ value: ppm)
2.75 (3H, s)
5.80 (2H, s)
7.10–8.00 (9H, m)

Reference Example 2

Preparation of 3-(2-chloro-6-fluorophenyl)-5-(3-chloro-4-methylphenyl) 1-methyl-1H-1,2,4-triazole A mixture of N-methyl-N-(p-toluenesulfonyl)-2-chloro-6-fluorobenzohydrazonoyl chloride (7.50 g), 3-chloro-4-methylbenzonitrile (3.33 g), anhydrous aluminum chloride (3.00 g) and o-dichlorobenzene (20 ml) is stirred at an oil bath temperature of 140° C. for 1 hour. After cooling, it is washed with saline. Then, it is dried over anhydrous magnesium sulfate and concentrated under reduced pressure. The concentrate is purified by silica gel column chromatography using mixed solvent of hexane-ethyl acetate as eluent to give 3.70 g of desired compound.

Reference Example 3

Preparation of 5-(4-bromomethyl-3-chlorophenyl)-3-(2-chloro-6-fluorophenyl) 1-methyl-1,2,4-triazole To carbon tetrachloride (50 ml) are added 3-(2-chloro-6-fluorophenyl)-5-(3-chloro-4-methylphenyl) 1-methyl-1H-1,2,4-triazole (3.37 g), N-bromosuccinicimide (2.14 g) and azobisisobutyronitrile (30 mg), which are heated under reflux for 1 hour with stirring. After cooling of the reaction mixture, insoluble matter is filtered off, and the filtrate is concentrated under reduced pressure. The concentrate is purified by silica gel column chromatography using mixed solvent of hexaneethyl acetate as eluent to give 2.51 g of desired compound (melting point 124.0°–126.0° C.).

Reference Example 4

Preparation of 5-(4-acetoxymethyl-3-chlorophenyl)-3-(2-chloro-6-fluorophenyl) 1-methyl-1H-1,2,4-triazole To N,N-dimethylformamide (200 ml) are added 5-(4-bromomethyl-3-chlorophenyl)-3(2-chloro-6-fluorophenyl)-1-methyl-1H-1,2,4-triazole (24.3 g) and potassium acetate (29.0 g), which are stirred at 130° C. for 3 hours. The reaction mixture is cooled to room temperature, poured into water and extracted with ethyl acetate. The organic layer is washed with water, dried over anhydrous magnesium sulfate and concentrated under reduced pressure. The concentrate is purified by silica gel column chromatography using mixed solvent of hexaneethyl acetate as eluent to give 11.8 g of desired compound.

NMR data (60 MHz, CDCl$_3$ solvent, δ value: ppm)
2.13 (3H, s)
4.07 (3H, s)
5.24 ( 2H, S)
6.90–7.85 (6H, m)

Reference Example 5

Preparation of 3-(2-chloro-6-fluorophenyl)-5-(3-chloro-4-hydroxymethylphenyl) 1-methyl-1H-1,2,4-triazole 5-(4-acetoxymethyl-3-chlorophenyl)-3(2-chloro-6-fluorophenyl)-1-methyl-1H-1,2,4-triazole (11.1 g) is dissolved in a mixed solvent of ethanol (50 ml) and water (20 ml), added with sodium hydroxide (2.3 g) and heated under reflux for 1 hour with stirring. After cooling to room temperature, the reaction mixture is added with ethyl acetate and washed with water. Then, it is dried over anhydrous magnesium sulfate and concentrated under reduced pressure to obtain crude solid. The crude solid is washed with mixed solvent of hexane-ethanol to give 6.7 g of desired compound (melting point: 111°–113° C.).

NMR data (60 MHz, CDCl$_3$ solvent, δ value: ppm)
3.50 (1H, t)
4.05 (3H, s)
4.75 (2H, d)
6.95–7.70 (6H, m)

Reference Example 6

Preparation of 3-(2-chloro-6-fluorophenyl)-5-(3-chloro-4-hydroxyphenyl) 1-methyl-1H-1,2,4-triazole To o-dichlorobenzene (200 ml) are added 3-chloro-4-methoxybenzonitrile (40.3 g) and anhydrous iron (III) chloride (42.2 g), which are heated at 120° C. with stirring. To this mixture is added dropwise a solution of N-methyl-N-(p-toluenesulfonyl)-2-chloro-6-fluorobenzohydrazonoyl chloride (62.2 g) in o-dichlorobenzene (300 ml) at 120° C. for 30 minutes with stirring, which are further stirred at 120° C. for 3 hours. After cooling to room temperature, the reaction mixture is poured into a large amount of water and extracted with chloroform. The organic layer is added with aqueous solution of 10% NaOH (200 ml) and aqueous solution of 25% ammonia (200 ml) and stirred at 50° C. for 1 hour. After cooling to room temperature, the organic layer is washed with water, dried over anhydrous magnesium sulfate, concentrated under reduced pressure to give 70.5 g of a crude product of 3-(2-chloro-6-fluorophenyl)-5-(3-chloro-4-methoxyphenyl) 1-methyl-1H-1,2,4-triazole.

To benzene (300 ml) are added the crude product of 3-(2-chloro-6-fluorophenyl)-5-(3-chloro-4-methoxyphenyl)-1-methyl 1H-1,2,4-triazole (70.5 g) and anhydrous aluminum chloride (80.0 g), which are heated under reflux for 3 hours with stirring. After cooling to room temperature, the reaction mixture is poured into ice water and extracted with toluene. The organic layer is washed with water, extracted with aqueous solution of 20% NaOH, and the aqueous layer is acidified by adding a concentrated sulfuric acid little by little while cooling with ice and extracted with ethyl acetate. The organic layer is washed with water, dried over anhydrous magnesium sulfate and concentrated under reduced pressure to give 64.2 g of desired compound.

NMR data (60 MHz, CDCl$_3$ solvent, δ value: ppm)

4.10 (3H, s)

7.00–7.90 (6H, m)

10.85 (1H, s)

The insecticide and acaricide according to the invention contain the triazole derivative shown by the general formula [I] as an active ingredient.

When the compounds according to the invention are used in the insecticide and acaricide, these compounds themselves may be used alone, or may be compounded with a carrier, a surfactant, a dispersing agent, an adjuvant or the like, which is usually used in the formulation, to form dust, wettable powder, emulsion, fine powder, granulate or the like. As the carrier used in the formulation, mention may be made of a solid carrier such as zeeklite, talc, bentonite, clay, kaolin, diatomaceous earth, white carbon, vermiculite, calcium hydroxide, quartz sand, ammonium sulfate, urea or the like; and a liquid carrier such as isopropyl alcohol, xylene, cyclohexane, methylnaphthalene or the like. As the surfactant and dispersing agent, mention may be made of a metal salt of alkylbenzene sulfonic acid, a metal salt of dinaphthylmethane disulfonic acid, a salt of sulfuric acid ester of alcohol, alkylarylsulfonate, lignin sulfonate, polyoxyethylene glycol ether, polyoxyethylene alkylaryl ether, polyoxyethylene sorbitan monoalkylate and the like. As the adjuvant, mention may be made of carboxymethyl cellulose, polyethylene glycol, gum arabic and the like. In use, the active ingredient is sprayed by diluting to a proper concentration or directly applied.

The insecticide and acaricide according to the invention may be used by spraying onto stem and leaves, by applying to soil, by applying to a nursery box, by spraying onto water surface or the like. The compounding ratio of the active ingredient may properly be selected, if necessary, but in case of the dust or granulate, it may properly be selected from a range of 0.05–20% (by weight), preferably 0.1%–10% (by weight). In case of the emulsion or wettable powder, it is suitable within a range of 0.5–80% (by weight). Preferably, it may properly be selected within a range of 1–60% (by weight).

The amount of the insecticide or acaricide according to the invention applied is dependent upon the kind of the compound used, injurious insect to be controlled, tendency and degree of insect injury, environmental condition, kind of formulation used and the like. When it is directly used as dust or granulate, the amount of the active ingredient is properly selected within a range of 0.05 g–5 kg, preferably 0.1 g–1 kg per 10 are. Furthermore, when it is used in form of a liquid as emulsion or wettable powder, the amount is properly selected within a range of 0.1–5,000 ppm, preferably 1–1,000 ppm. And also, the insecticide and acaricide according to the invention may be used by mixing with other insecticide, fungicide, fertilizer and plant growth regulator.

Then, the formulation will concretely be described with respect to typical examples. In this case, the kind of the compounds and additives and the compounding ratio are not limited to these examples and may be varied within wide ranges. Moreover, % is by weight otherwise specified.

Formulation Example 1

Emulsion

An emulsion is prepared by uniformly dissolving 30% of the compound (41), 20% of cyclohexanone, 11% of polyoxyethylene alkylaryl ether, 4% of calcium alkylbenzene sulfonate and 35% of methylnaphthaline.

Formulation Example 2

Wettable powder

A wettable powder is prepared by uniformly mixing and pulverizing 40% of the compound (389), 15% of diatomaceous earth, 15% of clay, 25% of white carbon, 2% of sodium dinaphthylmethane disulfonate and 3% of sodium lignin sulfonate.

Formulation Example 3

Dust

A dust is prepared by uniformly mixing and pulverizing 2% of the compound (116), 5% of diatomaceous earth and 93% of clay.

Formulation Example 4

Granulate

5% of the compound (41), 2% of sodium salt of lauryl alcohol sulfuric acid ester, 5% of sodium lignin sulfonate, 2% of carboxymethyl cellulose and 86% of clay are mixed and pulverized uniformly. Then, 100 parts by weight of this mixture is added and kneaded with 20 parts by weight of water and shaped into granulates of 14–32 mesh through an extrusion type granulating machine and dried to prepare granulates.

EFFECT OF THE INVENTION

The triazole derivatives according to the invention are effective for the control of planthoppers such as brown planthopper, white-backed planthopper, small brown planthopper and the like; leafhoppers such as green rice leafhopper, tea green leafhopper and the like; aphids such as cotton aphid, green peach aphid, cabbage aphid and the like; whiteflies such as greenhouse whitefly and the like; hemipteran injurious insects such as scales, e.g. mulberry scale or the like and bugs, e.g. corbett rice bug or the like; lepidopteran injurious insects such as diamond-back moth, beet armyworm, common cutworm and the like; dipteran injurious insects such as house fly, mosquito and the like; elytron injurious insects such as rice plant weevil, azuki bean weevil, cucurbit leaf beetle and the like; orthopteran injurious insects such as American cockroach, German cockroach and the like; and mites such as two-spotted spider mite, Kanzawa spider mite, citrus red mite and the like. Especially, they have a very excellent controlling effect against mites such as two-spotted spider mite, Kanzawa spider mite, citrus red mite and the like; and aphids such as cotton aphid, green peach aphid, cabbage aphid and the like.

The effect of the compound according to the invention will be described with respect to the following test examples. Moreover, compounds shown by chemical formula 3 in JP-A-56-154464 as comparative chemicals a–b and compounds shown in Technical Report RD278004 as comparative chemicals c–d are used in the same formulation as in the test compounds.

Comparative chemical a: 3,5-bis(2-chlorophenyl)-1-methyl-1H-1,2,4-triazole

Comparative chemical b: 3-(2-chlorophenyl)-1-methyl-5-(3-methylphenyl)-1H-1,2,4-triazole Comparative chemical c: 3-(2-chlorophenyl)-1-methyl-5-(3-chloro-2-methylphenyl) 1H-1,2,4-triazole Comparative chemical d: 3-(2-chloro-6-fluorophenyl)-1-methyl-5-(2,4-dichlorophenyl) 1H-1,2,4-triazole Test Example 1

Acaricidal test for two-spotted spider mite

The wettable powder prepared according to Formulation Example 2 is diluted with water so that the concentration of the active ingredient is 500 ppm. In the resulting diluted wettable powder are immersed soy bean seedlings previously inoculated with adults of two-spotted spider mite and then dried in air. After the treatment, the soy bean seedlings are placed in a thermostatic chamber of 25° C. for 14 days and then the number of living adults is counted to calculate the percentage of control efficiency according to a calculation formula (1). The control efficiency is evaluated according to a standard of Table 3. The results are shown in Table 4. Moreover, the test is carried out by double series.

$$\text{Control efficiency} = \left(1 - \frac{\text{number of adults before treatment at non-treated spot}}{\text{number of adults before treatment at treated spot}} \times \frac{\text{number of adults after the measured days at treated spot}}{\text{number of adults after the measured days at non-treated spot}} \times 100\right)$$

Calculation formula (1)

TABLE 3

| Control efficiency | Evaluation |
| --- | --- |
| control efficiency of not less than 90% | A |
| control efficiency of not less than 70% but less than 90% | B |
| control efficiency of not less than 50% but less than 70% | C |
| control efficiency of less than 50% | D |

TABLE 4

| Compound No. | Evaluation |
| --- | --- |
| 1 | A |
| 2 | A |
| 5 | A |
| 6 | A |
| 15 | A |
| 16 | B |
| 18 | B |
| 19 | B |
| 24 | B |
| 28 | B |
| 29 | A |
| 34 | B |
| 40 | A |
| 41 | A |
| 44 | A |
| 47 | A |
| 48 | A |
| 50 | A |
| 65 | B |
| 66 | A |
| 68 | B |
| 72 | B |
| 73 | B |
| 74 | A |
| 76 | A |
| 77 | A |
| 78 | A |
| 87 | A |
| 118 | A |

TABLE 4-continued

| Compound No. | Evaluation |
| --- | --- |
| 119 | A |
| 120 | A |
| 121 | B |
| 123 | A |
| 138 | A |
| 145 | A |
| 157 | A |
| 158 | A |
| 161 | A |
| 196 | A |
| 197 | A |
| 199 | A |
| 201 | A |
| 241 | A |
| 267 | A |
| 268 | A |
| 269 | A |
| 273 | A |
| 274 | A |
| 275 | A |
| 276 | A |
| 277 | A |
| 278 | A |
| 313 | B |
| 317 | A |
| 319 | A |
| 320 | A |
| 321 | A |
| 322 | A |
| 330 | A |
| 332 | A |
| 334 | A |
| 338 | A |
| 345 | B |
| 373 | A |
| 374 | A |
| 376 | A |
| 377 | A |
| 378 | A |
| 389 | A |
| 390 | B |
| 391 | A |
| 395 | A |
| 400 | A |
| 401 | A |
| 403 | A |
| 404 | A |
| 406 | A |
| 409 | A |
| 410 | A |
| 412 | A |
| 413 | A |
| 419 | A |
| 451 | B |
| 453 | B |
| 456 | A |
| 457 | A |
| 489 | A |
| 496 | A |
| 497 | A |
| 498 | A |
| 508 | A |
| 509 | A |
| 510 | A |
| 511 | A |
| 516 | A |
| 517 | A |
| 522 | A |
| 523 | A |
| 524 | A |
| 526 | A |
| 531 | B |
| Comparative chemical b | D |
| Comparative chemical c | D |

TABLE 4-continued

| Compound No. | Evaluation |
|---|---|
| Comparative chemical d | D |

Test Example 2

Insecticidal test for diamond-back moth

The wettable powder prepared according to Formulation Example 2 is diluted with water so that the concentration of the active ingredient is 500 ppm. Cabbage leaves are immersed in the resulting diluted solution, dried in air and then placed in a vinyl chloride cup. Ten larvae of diamond-back moth are released in the cup and thereafter a cover is placed thereon. Then, the cup is placed in a thermostatic chamber of 25° C. for 6 days, and the number of larvae died is counted to calculate the percentage of mortality according to a calculation formula (2). The mortality is evaluated according to a standard of Table 5. The results are shown in Table 6. Moreover, the test is carried out by double series.

TABLE 5

Calculation Formula (2)

$$\text{Mortality} = \frac{\text{number of larvae died in the measured days}}{\text{number of larvae before treatment}} \times 100$$

| Mortality | Evaluation |
|---|---|
| mortality of not less than 90% | A |
| mortality of not less than 70% but less than 90% | B |
| mortality of not less than 50% but less than 70% | C |
| mortality of less than 50% | D |

TABLE 6

| Compound No. | Evaluation |
|---|---|
| 51 | A |
| 78 | A |
| 116 | A |
| 118 | A |
| 157 | A |
| 158 | A |
| 161 | A |
| 196 | A |
| 197 | A |
| 199 | A |
| 276 | A |
| 317 | A |
| 319 | A |
| 320 | A |
| 321 | A |
| 322 | A |
| 330 | A |
| 332 | A |
| 334 | A |
| 338 | A |
| 376 | A |
| 391 | A |
| 409 | A |
| 413 | A |
| 419 | A |
| 456 | A |
| 457 | A |
| 496 | A |
| 497 | A |
| 498 | A |

TABLE 6-continued

| Compound No. | Evaluation |
|---|---|
| 514 | A |
| 524 | A |
| 526 | A |
| Comparative chemical a | D |
| Comparative chemical c | D |
| Comparative chemical d | D |

Test Example 3

Insecticidal test for brown planthopper

The wettable powder prepared according to Formulation Example 2 is diluted with water so that the concentration of the active ingredient is 500 ppm. In the resulting diluted wettable powder are immersed rice stems and leaves, which are then dried in air and placed in a test tube. In the test tube are released 10 larvae of brown planthopper and then the opening of the test tube is plugged with absorbent wadding. Thereafter, the test tube is placed in a thermostatic chamber of 25° C. for 6 days and then the number of larvae died is counted to calculate the percentage of mortality according to the calculation formula (2). The mortality is evaluated according to a standard of Table 5. The results are shown in Table 7. Moreover, the test is carried out by double series.

TABLE 7

| Compound No. | Evaluation |
|---|---|
| 2 | A |
| 78 | B |
| 116 | A |
| 311 | B |
| 378 | B |
| 395 | B |
| 517 | A |
| 524 | A |
| Comparative chemical a | D |
| Comparative chemical b | C |
| Comparative chemical d | D |

Test Example 4

Insecticidal test for cotton aphid

The wettable powder prepared according to Formulation Example 2 is diluted with water so that the concentration of the active ingredient is 100 ppm. In the resulting diluted wettable powder are immersed cucumber seedlings previously inoculated with larvae of cotton aphid and then dried in air. After the treatment, the cucumber seedlings are placed in a thermostatic chamber of 25° C. for 3 days and then the number of larvae died is counted to calculate the percentage of mortality according to the calculation formula (2). The mortality is evaluated according to a standard of Table 5. The results are shown in Table 8. Moreover, the test is carried out by double series.

TABLE 8

| Compound No. | Evaluation |
|---|---|
| 1 | B |
| 2 | A |
| 4 | A |
| 8 | B |
| 15 | A |
| 16 | A |
| 18 | A |
| 19 | A |
| 24 | A |
| 28 | A |
| 29 | A |
| 36 | A |
| 37 | A |
| 38 | A |
| 40 | A |
| 41 | A |
| 42 | A |
| 43 | A |
| 44 | A |
| 51 | A |
| 63 | B |
| 64 | A |
| 65 | A |
| 66 | A |
| 68 | A |
| 72 | A |
| 74 | A |
| 76 | A |
| 77 | A |
| 78 | A |
| 87 | A |
| 118 | A |
| 121 | A |
| 123 | A |
| 138 | A |
| 145 | A |
| 157 | A |
| 158 | A |
| 161 | A |
| 201 | A |
| 267 | A |
| 274 | B |
| 277 | A |
| 313 | A |
| 317 | A |
| 319 | A |
| 320 | A |
| 321 | A |
| 322 | A |
| 332 | A |
| 334 | A |
| 338 | A |
| 374 | A |
| 376 | A |
| 377 | A |
| 378 | A |
| 389 | A |
| 390 | A |
| 391 | A |
| 395 | A |
| 404 | B |
| 412 | A |
| 413 | A |
| 419 | A |
| 456 | A |
| 457 | A |
| 480 | A |
| 496 | A |
| 497 | A |
| 509 | A |
| 510 | A |
| 511 | A |
| 513 | A |
| 516 | A |
| 517 | A |
| 524 | A |
| 526 | A |
| 531 | A |

We claim:

1. A triazole derivative represented by a general formula:

wherein $R^1$ is a C1–C6 alkyl group, X is selected from the group consisting of a hydrogen atom, a halogen atom, a C1–C6 alkyl group, a C1–C6 alkoxy group, a C1–C6 alkylthio group, a nitro group and a cyano group, n is an integer of 1–5 provided that when n is 2 or more, X is the same or a different combination, Y' is selected from the group consisting of a halogen atom a C1–C6 alkyl group, a C1–C6 alkoxy group, a C1–C6 haloalkyl group, and a C1–C6 haloalkoxy group; m' is an integer of 1–4 provided that when m' is 2 or more, Y' is the same or a different combination; A is selected from the group consisting of an oxygen atom, a sulfur atom, a C1–C4 alkylene group, a C1–C4 alkyleneoxy group, a C1–C4 oxyalkylene group, a C1–C4 alkyleneoxy group, a C1–C4 alkylene group, a C1–C4 alkylenethio group, a C1–C4 thioalkylene group, a vinylerie group and an ethylene group; k is 0 or 1, $R^2$ is selected from the group consisting of a hydrogen atom, a halogen atom, a C1–C6 alkyl group, a C1–C6 alkoxy group, a trifluoromethyl group and a trifluoromethoxy group, j is an integer of 1–5 provided that when j is 2 or more, $R^2$ is the same or a different combination.

2. A triazole derivative according to claim 1 represented by the following formula:

wherein $R^1$ is an C1–C6 alkyl group, X is a hydrogen atom or a halogen atom, n is an integer of 1–5 provided that when n is 2 or more, X is the same or a different combination, Y' is selected from the group consisting of a halogen atom, a C1–C6 alkyl group, a C1–C6 alkoxy group, a C1–C6 haloalkyl group and a C1–C6 haloalkoxy group, m' is an integer of 1–4 provided that when m' is 2 or more, Y' is the same or a different combination, A is selected from the group consisting of an oxygen atom, a C1–C2 alkylene group, a C1–C2 alkyleneoxy group and a C1–C2 oxyalkylene group, k is 0 or 1, $R^2$ is a hydrogen atom, a halogen atom, a trifluoromethyl group and a trifluoromethoxy group, j is an integer of 1–5 provided that when j is 2 or more, $R^2$ is the same or a different combination.

3. A triazole derivative according to claim 2, wherein $R^1$ is a methyl group, X is a halogen atom, n is 1 or 2 provided that when n is 2, X is the same or a different combination, Y' is selected from the group consisting of a halogen atom, a C1–C6 alkyl group, a C1–C6 alkoxy group, a C1–C6 haloalkyl group and a C1–C6 haloalkoxy group, m' is an integer of 1 or 2 provided that when m' is 2, Y' is the same or a different combination, A is selected from the group consisting of an oxygen atom, a C1–C2 alkylene group, a C1–C2 alkyleneoxy group and a C1–C2 oxyalkylene group, k is 0 or 1, $R^2$ is selected from the group consisting of a hydrogen atom, a halogen atom, a trifluoromethyl group and a trifluoromethyoxy group, j is an integer of 1–3 provided that when j is 2 or 3, $R^2$ is the same or a different combination.

4. An insecticidal composition comprising an insecticidally effective amount of triazole derivative as defined in claim 1 and a carrier.

5. An acaricidal composition comprising an acaricidally effective amount of triazole derivative as defined in claim 2 and a carrier.

* * * * *